(12) United States Patent
Umeno et al.

(10) Patent No.: US 9,315,816 B2
(45) Date of Patent: Apr. 19, 2016

(54) METHOD FOR RAPIDLY DEVELOPING GENE SWITCHES AND GENE CIRCUITS

(75) Inventors: Daisuke Umeno, Chiba (JP); Hiroki Fukutomi, Chiba (JP); Kyoichi Saito, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 13/876,872

(22) PCT Filed: Nov. 2, 2011

(86) PCT No.: PCT/JP2011/075290
§ 371 (c)(1),
(2), (4) Date: Jun. 21, 2013

(87) PCT Pub. No.: WO2012/060407
PCT Pub. Date: May 10, 2012

(65) Prior Publication Data
US 2013/0267011 A1    Oct. 10, 2013

(30) Foreign Application Priority Data
Nov. 2, 2010   (JP) .................................. 2010-246271

(51) Int. Cl.
| | | |
|---|---|---|
| *C12N 1/21* | (2006.01) | |
| *C12N 15/70* | (2006.01) | |
| *C12Q 1/68* | (2006.01) | |
| *C12N 15/63* | (2006.01) | |
| C12N 1/38 | (2006.01) | |
| C12Q 1/48 | (2006.01) | |
| C12Q 1/02 | (2006.01) | |
| C07H 21/04 | (2006.01) | |

(52) U.S. Cl.
CPC ................ *C12N 15/70* (2013.01); *C12N 15/63* (2013.01); *C12N 15/635* (2013.01); *C12Q 1/6897* (2013.01)

(58) Field of Classification Search
None
See application file for complete search history.

(56) References Cited

PUBLICATIONS

Rhode, "Construction of a Genetic Switch for Inducible trans-Activation of Gene Expression in Eucaryotic Cells" 61(5) Journal of Virology 1448-1458 (1987).*
Vallur et al., "Effects of Hydrogen Bonding within a Damaged Base Pair on the Activity of Wild Type and DNA-intercalating Mutants of Human Alkyladenine DNA Glycosylase" 277(35) The Journal of Biological Chemistry 31673-31678 (2002).*
Tashirl et al., "A nucleoside kinase as a dual selector for genetic switches and circuits" Nucleic Acids Research 1-9 (Nov. 9, 2010).*
Kondo et al., "Structure and Expression of the alkB Gene of *Escherichia coli* Related to the Repair of Alkylated DNA" 261(33) The Journal of Biological Chemistry 15772-15777 (1986).*
Stavnezer et al., "Mechanism and Regulation of Class Switch Recombination" 26 Annual Review of Immunology 261-292 (2008).*
Office Action issued in corresponding Japanese Patent Application No. 2012-541895 dated Sep. 30, 2015 with partial English translation (6 pages).
Fukutomi et al., "Functional Selection of Genetic Switch and Gene Circuit," Abstract Papers of the 2010 Kanto-Branch Annual Meeting of the Japan Society for Bioscience, Biotechnology, and Agrochemistry, 2010, P-27 (2 pages).
Umeno, D., "Functional Selection Method for Gene Switch and Gene Circuit in High Speed and High-Efficiency," Hand out for the Chiba University New Technology Presentation Meeting, 2010, (32 pages).
Baldwin et al., "Human AP Endonuclease 1 Stimulates Multiple-Turnover Base Excision by Alkyladenine DNA Glycosylase," Biochemistry, vol. 48, No. 25, 2009, pp. 6022-6033.

* cited by examiner

*Primary Examiner* — Nancy J Leith
(74) *Attorney, Agent, or Firm* — Kilyk & Bowersox, P.L.L.C.

(57) ABSTRACT

Provided are: a selection method for a gene switch and a gene circuit, including using, as a selector, an expression vector containing at least a gene sequence whose expression is controlled by a transcription regulatory factor to be expressed when a genetic switch and a genetic circuit including the genetic switch operate, and a promoter sequence operably linked to the gene sequence upstream thereof; and an expression vector to be used in the selection method. This enables an effective selection method for a genetic switch and a genetic circuit, the selection method being able to be conducted within a short time period and with high selection efficiency and less leakiness.

20 Claims, 15 Drawing Sheets

Fig. 2-A
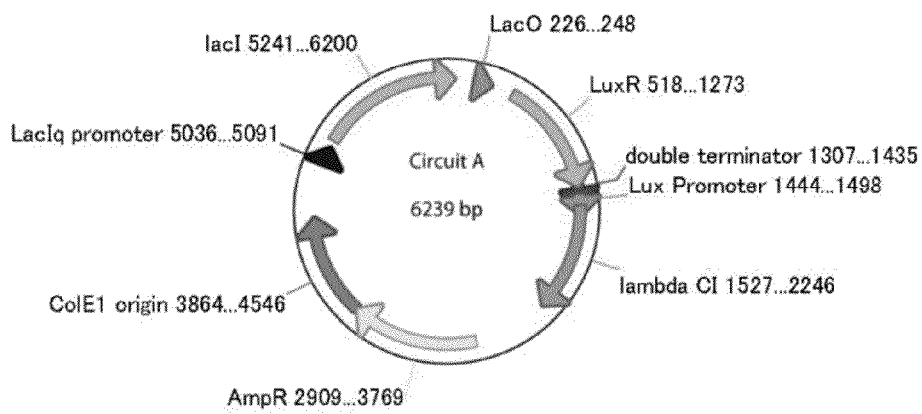
Fig. 2-B
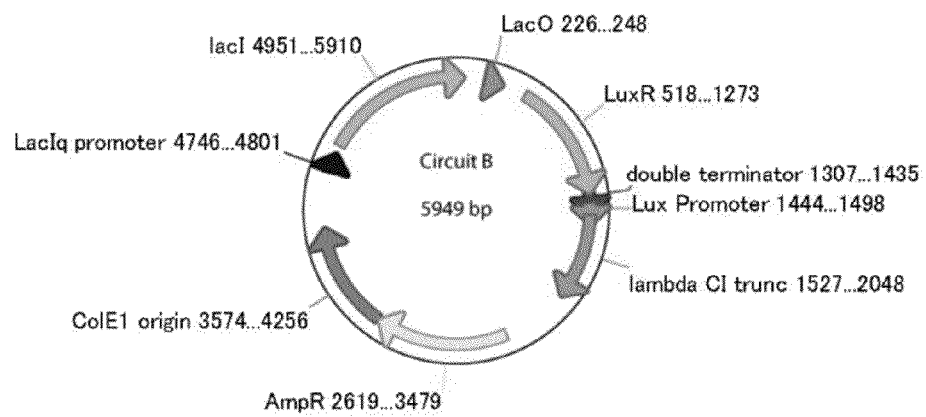

Fig. 2-C
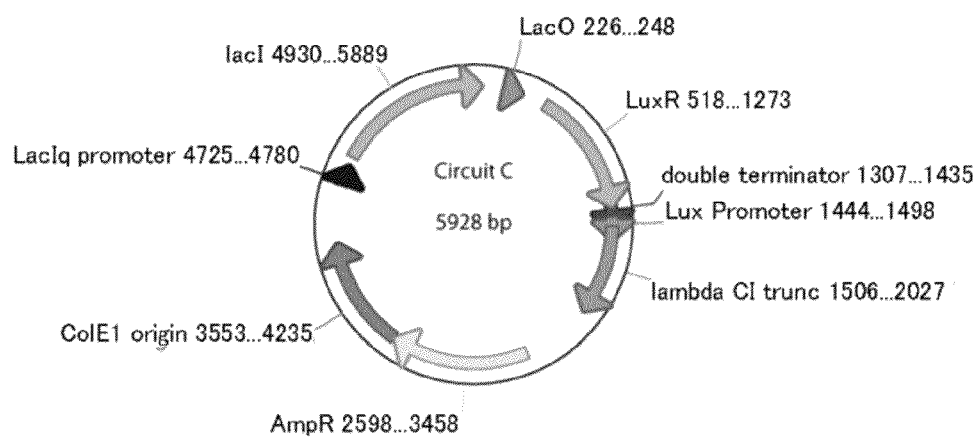
Fig. 2-D
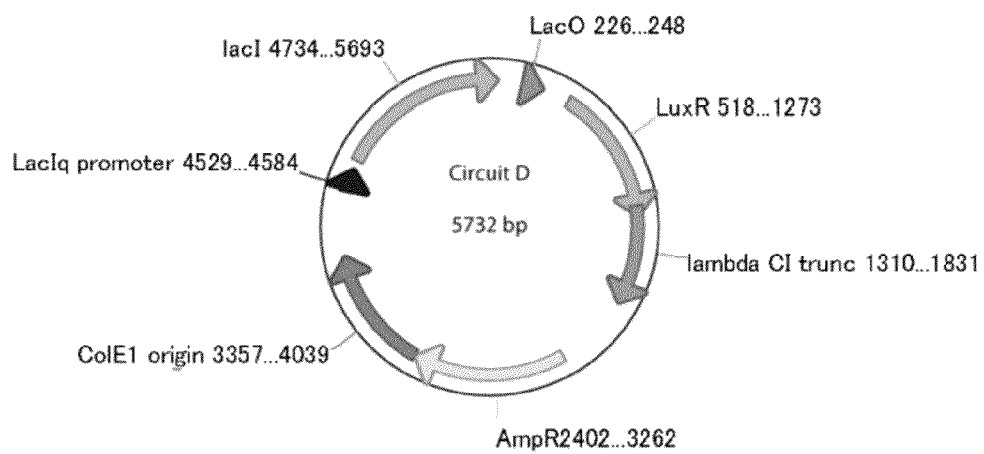

Fig. 9-A
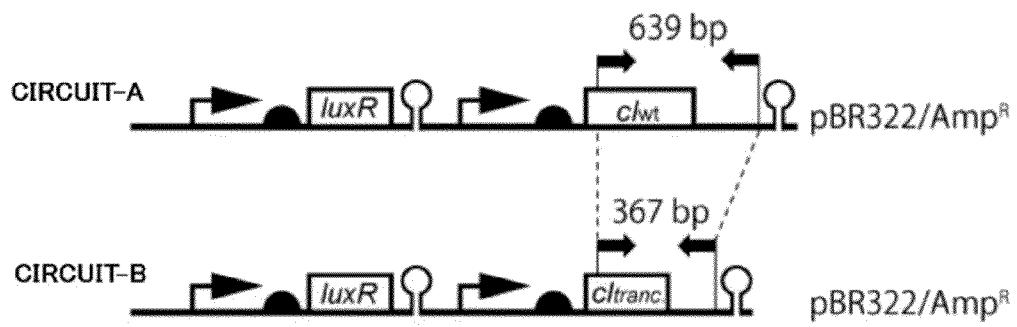
Fig. 9-B
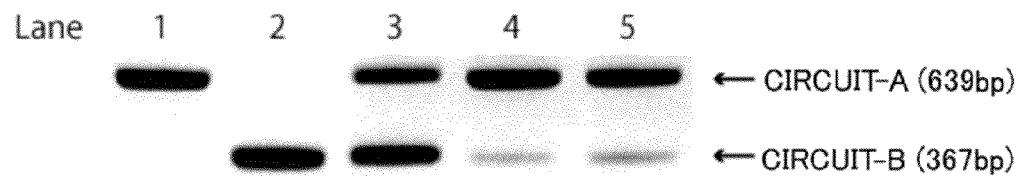
Fig. 10
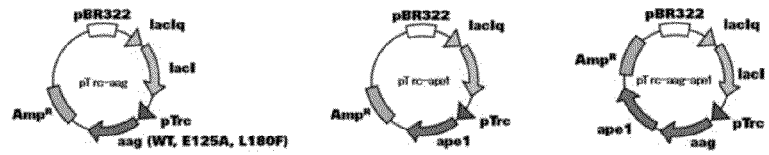
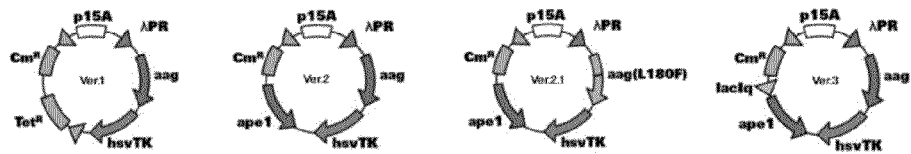

Fig. 11
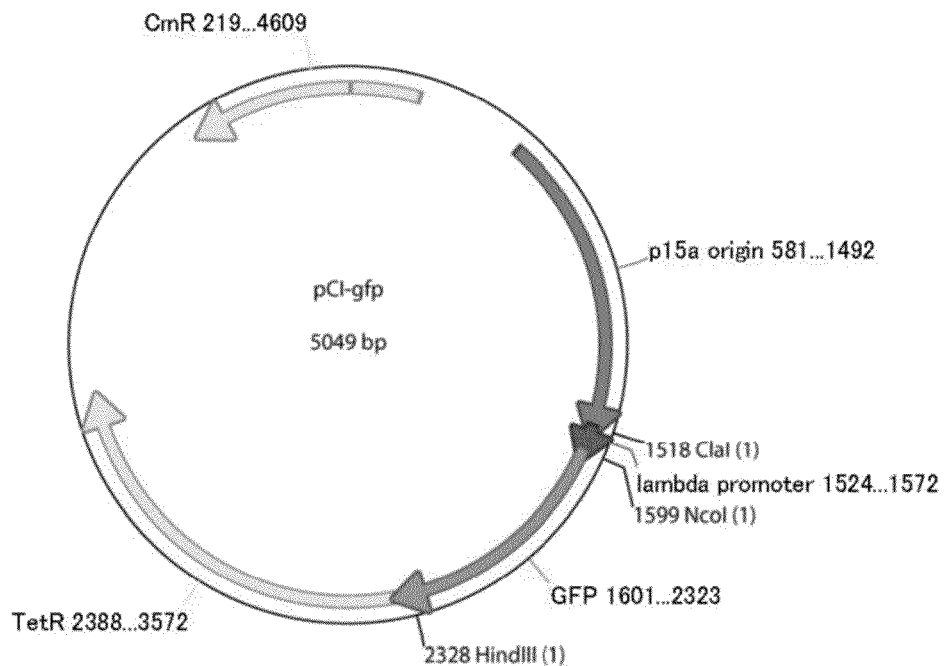
Fig. 12-A
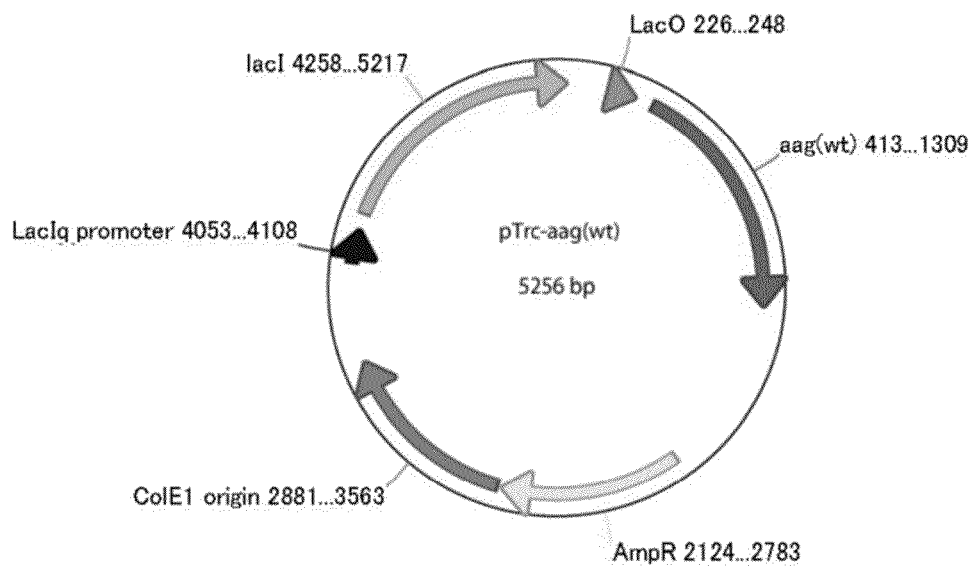

Fig. 12-B
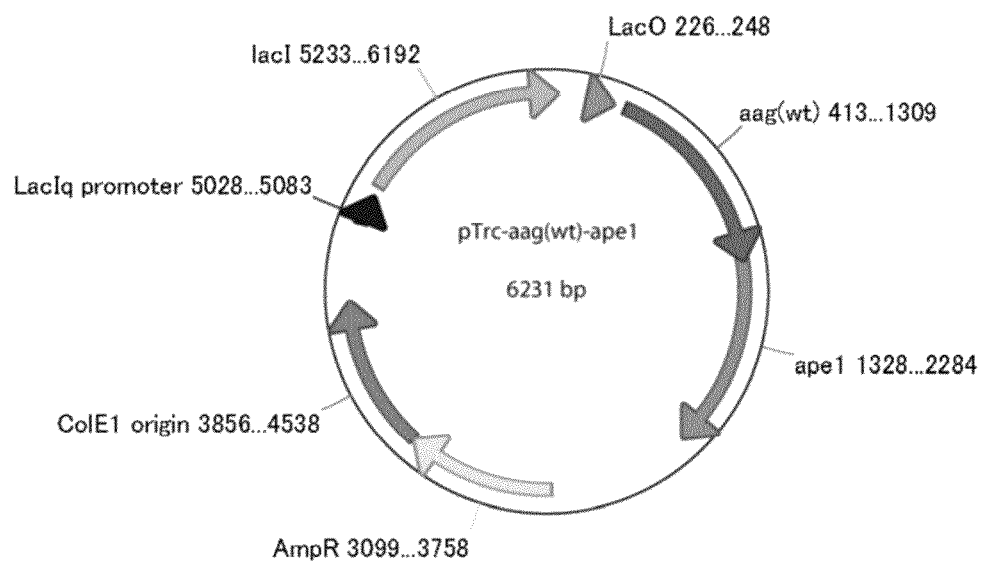
Fig. 12-C
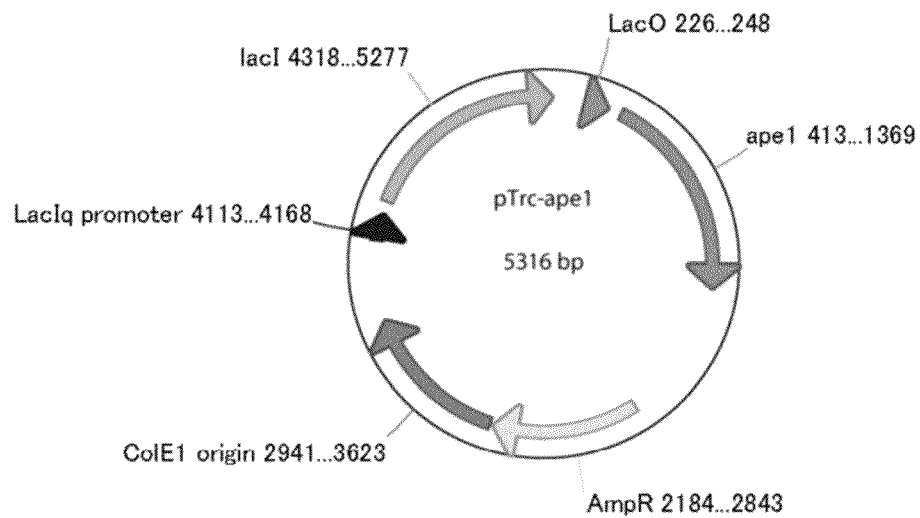

Fig. 13-A
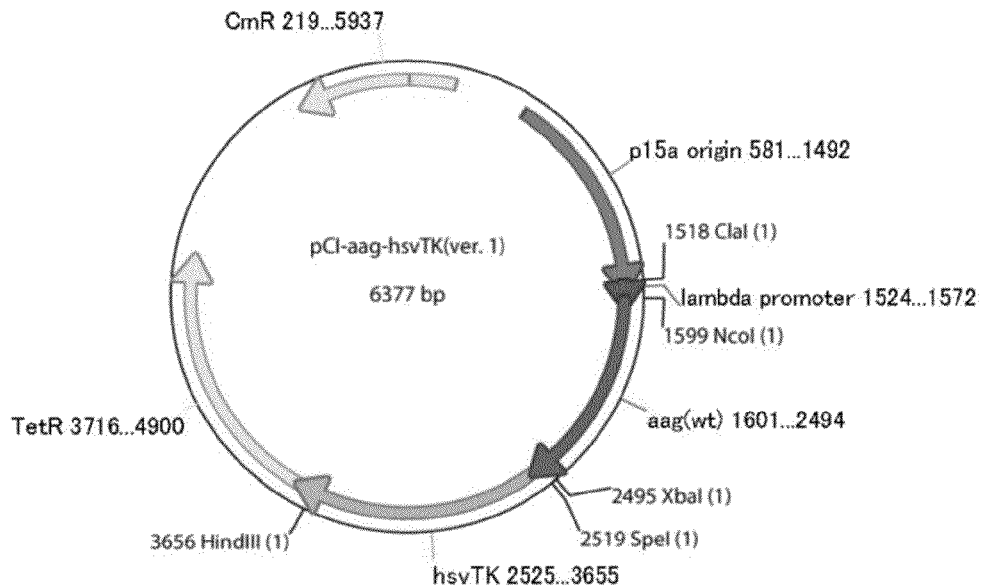
Fig. 13-B
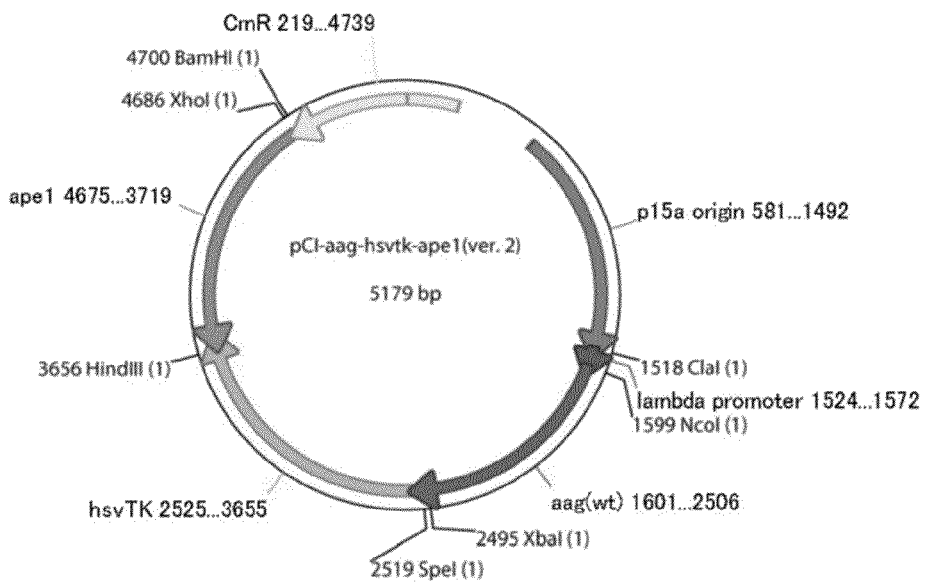

Fig. 13-C
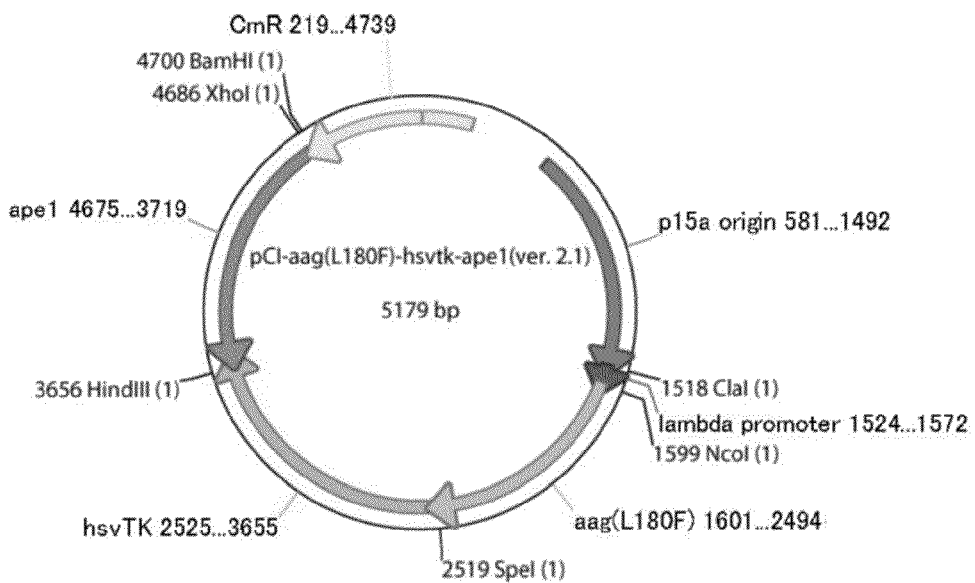
Fig. 13-D
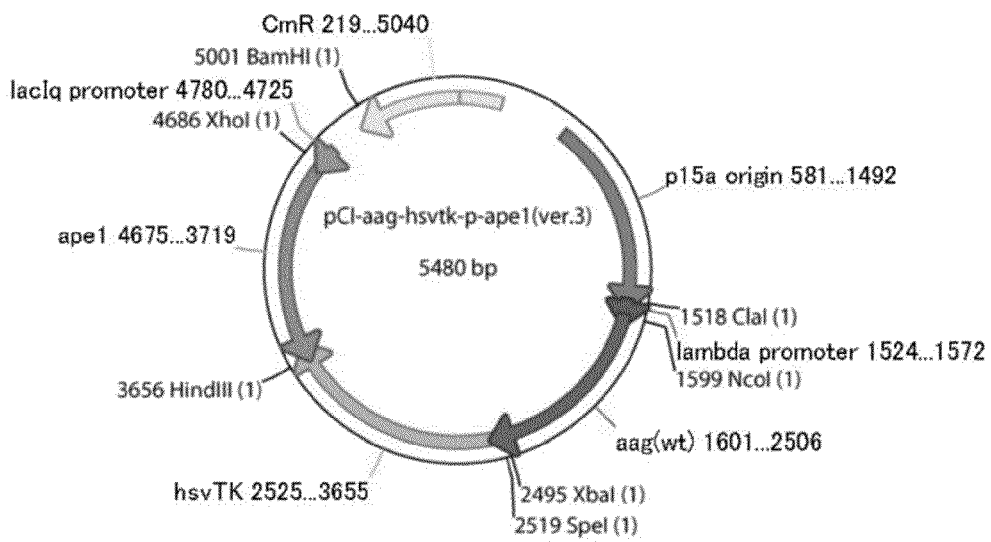

Fig. 14
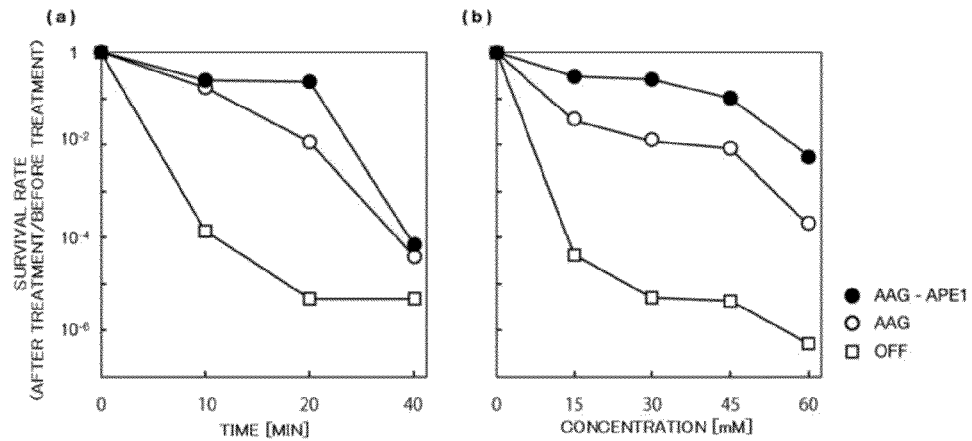
Fig. 15-A
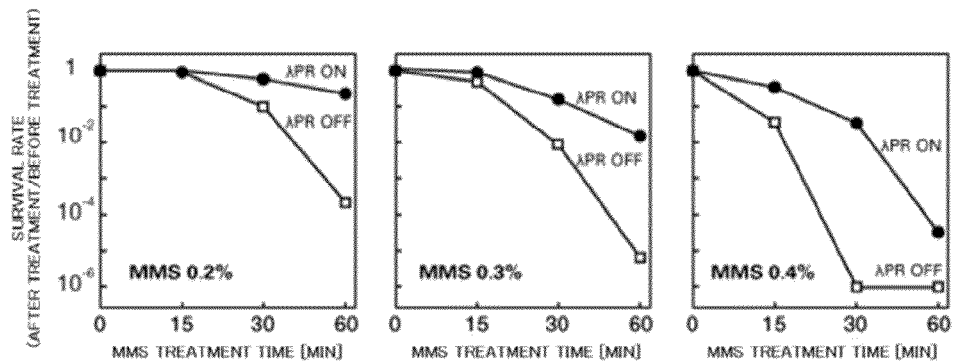
Fig. 15-B
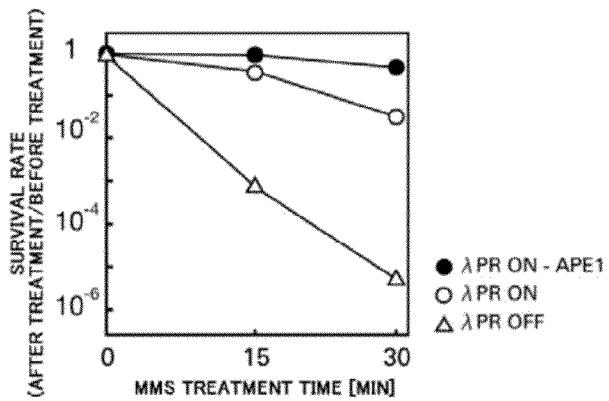

Fig. 18-A
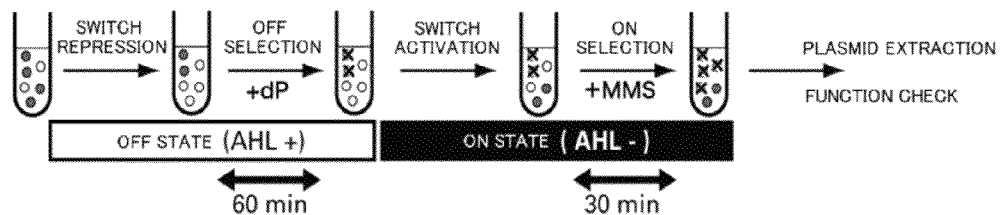
Fig. 18-B
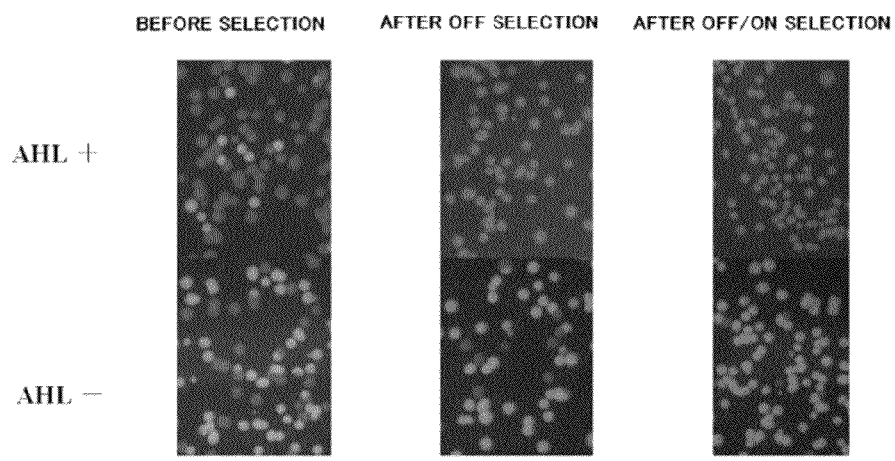
Fig. 19
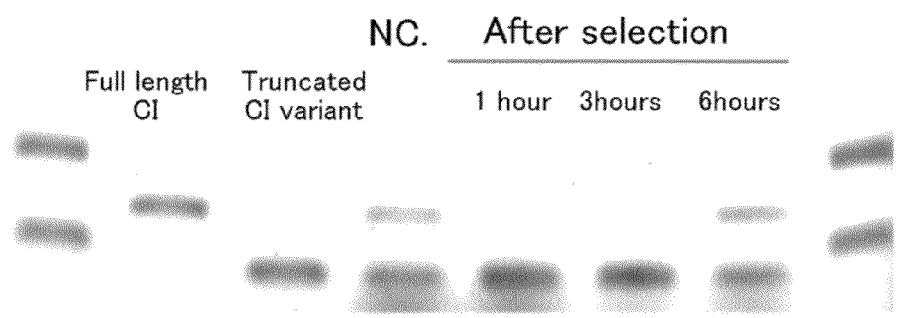

```
                             SEQUENCE LISTING

<160> NUMBER OF SEQ ID NOS: 12

<210> SEQ ID NO 1
    <211> LENGTH: 6377
    <212> TYPE: DNA
    <213> ORGANISM: artificial
    <220> FEATURE:
    <223> OTHER INFORMATION: Designed expression vector DNA named
          pCI-aag-hsvTK (Ver. 1) containing alkyladenine DNA glycosylase
          (AAG) gene and human herpes simplex virus thymidine kinase (hsvTK)
          gene

<400> SEQUENCE: 1
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
```

```
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttcaaga tttcagtgca   1440
atttatctct tcaaatgtag cacctgaagt cagccccata cgatataagt tgtaattctc   1500
atgtttgaca gcttatcatc gattaacacc gtgcgtgttg actattttac ctctggcggt   1560
gataatggtt gctactagag aaagaggaga aatactagcc atggtcaccc ccgctttgca   1620
gatgaagaaa ccaaagcagt tttgccgacg gatggggcaa agaagcagc gaccagctag   1680 agcagggcag ccacacagct cgtccgacgc agcccaggca cctgcagagc agccacacag   1740
ctcgtccgat gcagcccagg caccttgccc cagggagcgc tgcttgggac cgcccaccac   1800
tccgggccca taccgcagca tctatttctc aagcccaaag gccaccttac ccgactggg   1860 gttggagttc ttcgaccagc cggcagtccc cctggcccgg gcatttctgg gacaggtcct   1920
agtccggcga cttcctaatg gcacagaact ccgaggccgc atcgtggaga ccgaggcata   1980
cctggggcca gaggatgaag ccgcccactc aaggggtggc cggcagaccc ccgcaaccg   2040 aggcatgttc atgaagccgg ggaccctgta cgtgtacatc atttacggca tgtacttctg   2100
catgaacatc tccagccagg ggacggggc ttgcgtcttg ctgcgagcac tggagccct   2160 ggaaggtctg gagaccatgc gtcagcttcg cagcaccctc cggaaaggca ccgccagccg   2220
tgtcctcaag gaccgcgagc tctgcagtgg cccctccaag ctgtgccagg ccctggccat   2280
caacaagagc tttgaccaga gggacctggc acaggatgaa gctgtatggc tggagcgtgg   2340 tccctggag cccagtgagc cggctgtagt ggcagcagcc cgggtgggcg tcggccatgc   2400
aggggagtgg gcccggaaac ccctccgctt ctatgtccgg ggcagcccct gggtcagtgt   2460
ggtcgacaga gtggctgagc aggacacaca ggcctctaga taataacaat tcaggaggac   2520
tagtatggct tcgtaccccg gccatcaaca cgcgtctgcg ttcgaccagg ctgcgcgttc   2580
tcgcggccat agcaaccgac gtacggcgtt gcgccctcgc cggcagcaag aagccacgga   2640
agtccgcccg gagcagaaaa tgcccacgct actgcgggtt tatatagacg gtccccacgg   2700
gatggggaaa accaccacca cgcaactgct ggtggccctg gttcgcgcg acgatatcgt   2760 ctacgtaccc gagccgatga cttactggcg ggtgctgggg gcttccgaga caatcgcgaa   2820
catctacacc acacaacacc gcctcgacca gggtgagata tcggccgggg acgcggcggt   2880
ggtaatgaca agcgcccaga taacaatggg catgccttat gccgtgaccg acgccgttct   2940
ggctcctcat atcgggggg aggctgggag ctcacatgcc ccgcccccgg ccctcaccct   3000
catcttcgac cgccatccca tcgccgccct cctgtgctac ccggccgcgc ggtaccttat   3060
gggcagcatg acccccagg ccgtgctggc gttcgtggcc ctcatcccgc cgaccttgcc   3120
cggcaccaac atcgtgcttg ggcccttcc ggaggacaga cacatcgacc gcctggccaa   3180
acgccagcgc cccggcgagc ggctggacct ggctatgctg ctgcgattc gccgcgttta   3240 cgggctactt gccaatacgg tgcggtatct gcagtgcggc gggtcgtggc gggaggactg   3300
gggacagctt tcggggacgg ccgtgccgcc ccagggtgcc gagccccaga gcaacgcggg   3360
cccacgaccc catatcgggg acacgttatt taccctgttt cgggccccg agttgctggc   3420 ccccaacggc gacctgtata cgtgtttgc ctgggccttg gacgtcttgg ccaaacgcct   3480
ccgttccatg cacgtctttta tcctggatta cgaccaatcg cccgccggct gccgggacgc   3540
cctgctgcaa cttacctccg ggatggtcca gacccacgtc accaccccg gctccatacc   3600 gacgatatgc gacctggcgc gcacgtttgc ccgggagatg ggggaggcta actgaaagct   3660
```

```
ttaatgcggt agtttatcac agttaaattg ctaacgcagt caggcaccgt gtatgaaatc    3720
taacaatgcg ctcatcgtca tcctcggcac cgtcaccctg gatgctgtag cataggcttg    3780
ggttatgccg gtactgccgg gcctcttgcg ggatatcgtc cattccgaca gcatcgccag    3840
tcactatggc gtgctgctag cgctatatgc gttgatgcaa tttctatgcg cacccgttct    3900
cggagcactg tccgaccgct ttggccgccg cccagtcctg ctcgcttcgc tacttggagc    3960
cactatcgac tacgcgatca tggcgaccac acccgtcctg tggatcctct acgccggacg    4020
catcgtggcc ggcatcaccg gcgccacagg tgcggttgct ggcgcctata tcgccgacat    4080
caccgatggg gaagatcggg ctcgccactt cgggctcatg agcgcttgtt tcggcgtggg    4140
tatggtggca ggcccgtgg ccgggggact gttgggcgcc atctccttgc atgcaccatt    4200
ccttgcggcg gcgtgctca acggcctcaa cctactactg ggctgcttcc taatgcagga    4260
gtcgcataag ggagagcgtc gaccgatgcc cttgagagcc ttcaacccag tcagctcctt    4320
ccggtgggcg cggggcatga ctatcgtcgc cgcacttatg actgtcttct ttatcatgca    4380
actcgtagga caggtgccgg cagcgctctg ggtcattttc ggcgaggacc gctttcgctg    4440
gagcgcgacg atgatcggcc tgtcgcttgc ggtattcgga atcttgcacg ccctcgctca    4500
agccttcgtc actggtcccg ccaccaaacg tttcggcgag aagcaggcca ttatcgccgg    4560
catgcgggcc gacgcgctgg gctacgtctt gctggcgttc gcgacgcgag ctggatggc    4620 cttccccatt atgattcttc tcgcttccgg cggcatcggg atgcccgcgt tgcaggccat    4680
gctgtccagg caggtagatg acgaccatca gggacagctt caaggatcgc tcgcggctct    4740
taccagccta acttcgatca ctggaccgct gatcgtcacg gcgatttatg ccgcctcggc    4800
gagcacatgg aacggggttgg catggattgt aggcgccgcc ctataccttg tctgcctccc    4860
cgcgttgcgt cgcggtgcat ggagccgggc cacctcgacc tgaatggaag ccggcggcac    4920
ctcgctaacg gattcaccac tccaagaatt ggagccaatc aattcttgcg gagaactgtg    4980
aatgcgcaaa ccaacccttg gcagaacata tccatcgcgt ccgccatctc cagcagccgc    5040
acgcggcgca tctcgggcag cgttgggtcc tggccacggg tgcgcatgat cgtgctcctg    5100
tcgttgagga cccggctagg ctggcggggt tgccttactg gttagcagaa tgaatcaccg    5160
atacgcgagc gaacgtgaag cgactgctgc tgcaaaacgt ctgcgacctg agcaacaaca    5220
tgaatggtct tcgttttccg tgtttcgtaa agtctgaaa cgcggaagtc ccctacgtgc    5280
tgctgaagtt gcccgcaaca gagagtggaa ccaaccggtg ataccacgat actatgactg    5340
agagtcaacg ccatgagcgg cctcatttct tattctgagt tacaacagtc cgcaccgctg    5400
tccggtagct ccttccggtg ggcgcggggc atgactatcg tcgccgcact tatgactgtc    5460
ttctttatca tgcaactcgt aggacaggtg ccggcagcgc caacagtcc cccggccacg    5520 gggcctgcca ccatacccac gccgaaacaa gcgccctgca ccattatgtt ccggatctgc    5580
atcgcaggat gctgctggct accctgtgga acacctacat ctgtattaac gaagcgctaa    5640 ccgttttat caggctctgg gaggcagaat aaatgatcat atcgtcaatt attacctcca    5700
cggggagagc ctgagcaaac tggcctcagg catttgagaa gcacacggtc acactgcttc    5760
cggtagtcaa taaccggta aaccagcaat agacataagc ggctatttaa cgaccctgcc    5820
ctgaaccgac gaccgggtcg aatttgcttt cgaatttctg ccattcatcc gcttattatc    5880
acttattcag gcgtagcacc aggcgtttaa gggcaccaat aactgcccta aaaaaattac    5940
gccccgccct gccactcatc gcagtactgt tgtaattcat taagcattct gccgacatgg    6000
```

```
aagccatcac aaacggcatg atgaacctga atcgccagcg gcatcagcac cttgtcgcct    6060
tgcgtataat atttgcccat cgtgaaaacg ggggcgaaga agttgtccat attggccacg    6120
tttaaatcaa aactggtgaa actcacccag ggattggctg agacgaaaaa catattctca    6180 ataaacccttt tagggaaata ggccaggttt tcaccgtaac acgccacatc ttgcgaatat    6240
atgtgtagaa actgccggaa atcgtcgtgg tattcactcc agagcgatga aaacgtttca    6300
gtttgctcat ggaaaacggt gtaacaaggg tgaacactat cccatatcac cagctcaccg    6360
tctttcattg ccatacg                                                    6377
```

<210> SEQ ID NO 2
<211> LENGTH: 5179
<212> TYPE: DNA
<213> ORGANISM: artificial
<220> FEATURE:
<223> OTHER INFORMATION: Designed expression vector DNA named
      pCI-aag-hsvTK-ape1 (Ver. 2) containing alkyladenine DNA
      glycosylase (AAG) gene, human herpes simplex virus thymidine
      kinase (hsvTK) gene, and AP endonuclease (APE1) gene

<400> SEQUENCE: 2

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gccttttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttcaaga tttcagtgca    1440
atttatctct tcaaatgtag cacctgaagt cagccccata cgatataagt tgtaattctc    1500
atgtttgaca gcttatcatc gattaacacc gtgcgtgttg actattttac ctctggcggt    1560
```

```
gataatggtt gctactagag aaagaggaga aatactagcc atggtcaccc ccgctttgca   1620
gatgaagaaa ccaaagcagt tttgccgacg gatggggcaa aagaagcagc gaccagctag   1680
agcagggcag ccacacagct cgtccgacgc agcccaggca cctgcagagc agccacacag   1740
ctcgtccgat gcagcccagg caccttgccc cagggagcgc tgcttgggac cgcccaccac   1800
tccgggccca taccgcagca tctatttctc aagcccaaag ggccacctta cccgactggg   1860
gttggagttc ttcgaccagc cggcagtccc cctggcccgg gcatttctgg gacaggtcct   1920
agtccggcga cttcctaatg gcacagaact ccgaggccgc atcgtggaga ccgaggcata   1980 cctgggggcca gaggatgaag ccgcccactc aaggggtggc cggcagaccc cccgcaaccg   2040
aggcatgttc atgaagccgg ggaccctgta cgtgtacatc atttacggca tgtacttctg   2100
catgaacatc tccagccagg gggacggggc ttgcgtcttg ctgcgagcac tggagcccct   2160
ggaaggtctg gagaccatgc gtcagcttcg cagcaccctc cggaaaggca ccgccagccg   2220
tgtcctcaag gaccgcgagc tctgcagtgg cccctccaag ctgtgccagg ccctggccat   2280
caacaagagc tttgaccaga gggacctggc acaggatgaa gctgtatggc tggagcgtgg   2340 tccccctggag cccagtgagc cggctgtagt ggcagcagcc cgggtgggcg tcggccatgc   2400
aggggagtgg gcccggaaac ccctccgctt ctatgtccgg ggcagcccct gggtcagtgt   2460
ggtcgacaga gtggctgagc aggacacaca ggcctctaga taataacaat tcaggaggac   2520
tagtatggct tcgtaccccg gccatcaaca cgcgtctgcg ttcgaccagg ctgcgcgttc   2580
tcgcggccat agcaaccgac gtacggcgtt gcgccctcgc cggcagcaag aagccacgga   2640
agtccgcccg gagcagaaaa tgcccacgct actgcgggtt tatatagacg gtccccacgg   2700
gatggggaaa accaccacca cgcaactgct ggtggccctg ggttcgcgcg acgatatcgt   2760
ctacgtaccc gagccgatga cttactgcgg ggtgctgggg gcttccgaga caatcgcgaa   2820
catctacacc acacaacacc gcctcgacca gggtgagata tcggccgggg acgcggcgt   2880 ggtaatgaca agcgcccaga taacaatggg catgccttat gccgtgaccg acgccgttct   2940
ggctcctcat atcggggggg aggctgggag ctcacatgcc ccgcccccgg ccctcaccct   3000
catcttcgac cgccatccca tcgccgccct cctgtgctac ccggccgcgc ggtaccttat   3060
gggcagcatg accccccagg ccgtgctggc gttcgtggcc ctcatcccgc cgaccttgcc   3120
cggcaccaac atcgtgcttg ggccccttcc ggaggacaga cacatcgacc gcctggccaa   3180
acgccagcgc cccggcgagc ggctggacct ggctatgctg gctgcgattc gccgcgttta   3240
cgggctactt gccaatacgg tgcggtatct gcagtgcggc gggtcgtggc gggaggactg   3300
gggacagctt tcggggacgg ccgtgccgcc ccagggtgcc gagccccaga gcaacgcggg   3360
cccacgaccc catatcgggg acacgttatt taccctgttt cgggccccg agttgctggc   3420 ccccaacggc gacctgtata cgtgtttgc ctgggccttg gacgtcttgg ccaaacgcct   3480
ccgttccatg cacgtctttta tcctggatta cgaccaatcg cccgccggct gccgggacgc   3540
cctgctgcaa cttacctccg ggatggtcca gacccacgtc accaccccg gctccatacc   3600 gacgatatgc gacctggcgc gcacgtttgc ccgggagatg ggggaggcta actgaaagct   3660
ttaatgcggt agtttatcac agttaaattg ctaacgcagt caggcaccgt gtatgctttc   3720
acagtgctag gtataggtg ataggacagt gatcactgcc gagggccttg aacggatct    3780 tgctgtcaca caatgcaggt aacagagagt gggacaacaa aaagtaatca aggcgccaac   3840
caacattctt ggatcgagca ttcatcatat aagtccaaaa ggtgtaggca tagggtgtgt   3900
tggggtagag gtgcctaaag ctgtcagcca gtggcacagc ctgcagtaat tccccgaagc   3960
```

```
cttggcgctc ttgtggcgtg aagccagcat tcttttttgtt cccctttggg ttgcgaaggt   4020
caatttcttc atgtgccaca ttgaggtctc cacacagcac aaggggcttt cgggaagcca   4080
ggcccttcag gaacttgcga aaggcttcat cccagcgctg ccggtactcc agtcgtacca   4140
gacctcggcc tgcattaggt acatatgctg ttaccagcac aaacgagtca aattcagcca   4200
caatcacccg gccttcctga tcatgctcct catcgcctat gccgtaagaa actttgagtg   4260
ggcactggcg ggaaagcagg cccacgccac tgtacccttc cttgtccgaa ggagctgacc   4320
agtattgatg agagagtcca ggcagctcct gaagttcagc tggtagtttg ttctctgaac   4380
atttggtctc ttgaaggcac agtatatctg gggcttcttc ctttacccaa tctaatcctt   4440
tcttcttaat ccaggctcga agcccatcca cattccaaga gcagatcttg agtgtggcag   4500
gtttgccact gggtgaggtt ttctgatctg ggggtcctc atacagggct gggccctctc   4560
ctgctgcctc tttgtcattt ttctttgcgg ccgtcttact cttcttggcc tctggctctg   4620
tcctgagctc atccccgtct tccgccaccg ctcccttttt cccacgcttc ggcatttata   4680
tcctcctcga gggatctttg gatcccgttt aagggcacca ataactgcct taaaaaaatt   4740
acgccccgcc ctgccactca tcgcagtact gttgtaattc attaagcatt ctgccgacat   4800
ggaagccatc acaaacggca tgatgaacct gaatcgccag cggcatcagc accttgtcgc   4860
cttgcgtata atatttgccc atcgtgaaaa cgggggcgaa gaagttgtcc atattggcca   4920
cgtttaaatc aaaactggtg aaactcaccc agggattggc tgagacgaaa aacatattct   4980
caataaaccc tttagggaaa taggccaggt tttcaccgta acacgccaca tcttgcgaat   5040
atatgtgtag aaactgccgg aaatcgtcgt ggtattcact ccagagcgat gaaaacgttt   5100
cagtttgctc atggaaaacg gtgtaacaag ggtgaacact atcccatatc accagctcac   5160
cgtctttcat tgccatacg                                                 5179
```

<210> SEQ ID NO 3
<211> LENGTH: 5179
<212> TYPE: DNA
<213> ORGANISM: artificial
<220> FEATURE:
<223> OTHER INFORMATION: Designed expression vector DNA named
      pCI-aagL180F-hsvTK-ape1 (Ver. 2.1) containing alkyladenine DNA
      glycosylase mutant (AAG(L180F)) gene, human herpes simplex virus
      thymidine kinase (hsvTK) gene, and AP endonuclease (APE1) gene

<400> SEQUENCE: 3

```
gaattccgga tgagcattca tcaggcgggc aagaatgtga ataaaggccg gataaaactt    60
gtgcttattt ttctttacgg tctttaaaaa ggccgtaata tccagctgaa cggtctggtt   120
ataggtacat tgagcaactg actgaaatgc ctcaaaatgt tctttacgat gccattggga   180
tatatcaacg gtggtatatc cagtgatttt tttctccatt ttagcttcct tagctcctga   240
aaatctcgat aactcaaaaa atacgcccgg tagtgatctt atttcattat ggtgaaagtt   300
ggaacctctt acgtgccgat caacgtctca ttttcgccaa aagttggccc agggcttccc   360
ggtatcaaca gggacaccag gatttattta ttctgcgaag tgatcttccg tcacaggtat   420
ttattcggcg caaagtgcgt cgggtgatgc tgccaactta ctgatttagt gtatgatggt   480
gtttttgagg tgctccagtg gcttctgttt ctatcagctg tccctcctgt tcagctactg   540
acggggtggt gcgtaacggc aaaagcaccg ccggacatca gcgctagcgg agtgtatact   600
ggcttactat gttggcactg atgagggtgt cagtgaagtg cttcatgtgg caggagaaaa   660
aaggctgcac cggtgcgtca gcagaatatg tgatacagga tatattccgc ttcctcgctc   720
```

```
actgactcgc tacgctcggt cgttcgactg cggcgagcgg aaatggctta cgaacggggc    780
ggagatttcc tggaagatgc caggaagata cttaacaggg aagtgagagg ccgcggcaa    840 agccgttttt ccataggctc cgccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttcaaga tttcagtgca   1440
atttatctct tcaaatgtag cacctgaagt cagccccata cgatataagt tgtaattctc   1500
atgtttgaca gcttatcatc gattaacacc gtgcgtgttg actattttac ctctggcggt   1560
gataatggtt gctactagag aaagaggaga aatactagcc atggtcaccc ccgctttgca   1620
gatgaagaaa ccaaagcagt tttgccgacg gatgggcaa aagaagcagc gaccagctag   1680
agcagggcag ccacacagct cgtccgacgc agcccaggca cctgcagagc agccacacag   1740
ctcgtccgat gcagcccagg caccttgccc caggagcgc tgcttgggac cgcccaccac   1800
tccgggccca taccgcagca tctatttctc aagcccaaag ggccacctta cccgactggg   1860
gttggagttc ttcgaccagc cggcagtccc cctggcccgg gcatttctgg acaggtcct    1920 agtccggcga cttcctaatg gcacagaact ccgcggccgc atcgtggaga ccgaggcata   1980
cctggggcca gaggatgaag ccgcccactc aaggggtggc cggcagaccc cccgcaaccg   2040
aggcatgttc atgaagccgg gtaccctgta cgtgtacatc atttacggca tgtacttctg   2100
tatgaacatc tccagccagg cgacgggggc ttgcgtcttt ctgcgagctc tagagcccct   2160
ggaaggtctg gagaccatgc gtcagcttcg cagcaccctc cggaaaggca ccgccagccg   2220
tgtcctcaag gaccgcgagc tctgcagtgg cccctccaag ctgtgccagg ccctggccat   2280
caacaagagc tttgaccaga gggacctggc acaggatgaa gctgtatggc tggagcgtgg   2340
tcccctggag cccagtgagc cggctgtagt ggcagcagcc cgggtgggcg tcggccatgc   2400
aggggagtgg gcccggaaac ccctccgctt ctatgtccgg ggcagcccct gggtcagtgt   2460
ggtcgacaga gtggctgagc aggacacaca ggcctctaga taataacaat tcaggaggac   2520
tagtatggct tcgtaccccg gccatcaaca cgcgtctgcg ttcgaccagg ctgcgcgttc   2580
tcgcggccat agcaaccgac gtacggcgtt gcgcctcgc cggcagcaag aagccacgga   2640
agtccgcccg gagcagaaaa tgcccacgct actgcgggtt tatatagacg tccccacgg    2700 gatgggaaa accaccacca cgcaactgct ggtggccctg ggttcgcgcg acgatatcgt    2760
ctacgtaccc gagccgatga cttactggcg ggtgctgggg cttccgaga caatcgcgaa    2820 catctacacc acacaacacc gcctcgacca gggtgagata tcggccgggg acgcggcggt   2880
ggtaatgaca agcgcccaga taacaatggg catgccttat gccgtgaccg acgccgttct   2940
ggctcctcat atcgggggggg aggctgggag ctcacatgcc ccgcccccgg ccctcaccct   3000
catcttcgac cgccatccca tcgccgccct cctgtgctac ccggccgcgc ggtaccttat   3060
```

```
gggcagcatg accccccagg ccgtgctggc gttcgtggcc ctcatcccgc cgaccttgcc    3120
cggcaccaac atcgtgcttg gggcccttcc ggaggacaga cacatcgacc gcctggccaa    3180
acgccagcgc cccggcgagc ggctggacct ggctatgctg gctgcgattc gccgcgttta    3240
cgggctactt gccaatacgg tgcggtatct gcagtgcggc gggtcgtggc gggaggactg    3300
gggacagctt tcggggacgg ccgtgccgcc ccagggtgcc gagcccagag caacgcgggc    3360
cccacgaccc catatcgggg acacgttatt taccctgttt cgggcccccg agttgctggc    3420
ccccaacggc gacctgtata cgtgtttgc ctgggccttg gacgtcttgg ccaaacgcct    3480
ccgttccatg cacgtctttta tcctggatta cgaccaatcg cccgccggct gccgggacgc    3540
cctgctgcaa cttacctccg ggatggtcca gacccacgtc accaccccg gctccatacc    3600 gacgatatgc gacctggcgc gcacgtttgc ccggggagatg ggggaggcta actgaaagct    3660
ttaatgcggt agtttatcac agttaaattg ctaacgcagt caggcaccgt gtatgctttc    3720
acagtgctag gtatagggtg ataggacagt gatcactgcc gagggccttg gaacggatct    3780
tgctgtcaca caatgcaggt aacagagagt gggacaacaa aaagtaatca aggcgccaac    3840
caacattctt ggatcgagca ttcatcatat aagtccaaaa ggtgtaggca tagggtgtgt    3900
tggggtagag gtgcctaaag ctgtcagcca gtggcacagc ctgcagtaat ccccgaagc    3960 cttggcgctc ttgtggcgtg aagccagcat tctttttgtt ccccttgggg ttgcgaaggt    4020
caatttcttc atgtgccaca ttgaggtctc cacacagcac aaggggcttt cgggaagcca    4080
ggcccttcag gaacttgcga aaggcttcat cccagcgctg ccggtactcc agtcgtacca    4140
gacctcggcc tgcattaggt acatatgctg ttaccagcac aaacgagtca aattcagcca    4200
caatcacccg gccttcctga tcatgctcct catcgcctat gccgtaagaa actttgagtg    4260
ggcactggcg ggaaagcagg cccacgccac tgtacccttc cttgtccgaa ggagctgacc    4320
agtattgatg agagagtcca ggcagctcct gaagttcagc tggtagtttg ttctctgaac    4380
atttggtctc ttgaaggcac agtatatctg gggcttcttc ctttacccaa tctaatcctt    4440
tcttcttaat ccaggctcga agcccatcca cattccaaga gcagatcttg agtgtggcag    4500
gtttgccact gggtgaggtt ttctgatctg ggggtcctc atacagggct gggccctctc    4560
ctgctgcctc tttgtcattt ttctttgcgg ccgtcttact cttcttggcc tctggctctg    4620
tcctgagctc atccccgtct tccgccaccg ctcccttttt cccacgcttc ggcatttata    4680
tcctcctcga gggatctttg gatcccgttt aagggcacca ataactgcct taaaaaaatt    4740
acgccccgcc ctgccactca tcgcagtact gttgtaattc attaagcatt ctgccgacat    4800
ggaagccatc acaaacggca tgatgaacct gaatcgccag cggcatcagc accttgtcgc    4860
cttgcgtata atatttgccc atcgtgaaaa cgggggcgaa gaagttgtcc atattggcca    4920
cgtttaaatc aaaactggtg aaactcaccc agggattggc tgagacgaaa aacatattct    4980
caataaaccc tttagggaaa taggccaggt tttcaccgta acacgccaca tcttgcgaat    5040
atatgtgtag aaactgccgg aaatcgtcgt ggtattcact ccagagcgat gaaaacgttt    5100
cagtttgctc atggaaaacg gtgtaacaag ggtgaacact atcccatatc accagctcac    5160
cgtctttcat tgccatacg                                                 5179
```

<210> SEQ ID NO 4
<211> LENGTH: 5480
<212> TYPE: DNA
<213> ORGANISM: artificial
<220> FEATURE:
<223> OTHER INFORMATION: Designed expression vector DNA named pCI-aag-hsvTK-ape1(Ver.3) containing alkyladenine DNA glycosylase
(AAG) gene, human herpes simplex virus thymidine kinase (hsvTK)
gene, and AP endonuclease (APE1) gene

<400> SEQUENCE: 4

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttcaaga tttcagtgca    1440
atttatctct tcaaatgtag cacctgaagt cagccccata cgatataagt tgtaattctc    1500
atgtttgaca gcttatcatc gattaacacc gtgcgtgttg actatttac tctctggcggt    1560
gataatggtt gctactagag aaagaggaga atactagcc atggtcaccc ccgctttgca    1620
gatgaagaaa ccaaagcagt tttgccgacg gatggggcaa aagaagcagc gaccagctag    1680
agcagggcag ccacacagct cgtccgacgc agcccaggca cctgcagagc agccacacag    1740
ctcgtccgat gcagcccagg caccttgccc caggagcgc tgcttgggac cgcccaccac    1800
tccgggccca taccgcagca tctatttctc aagcccaaag ggccaccta cccgactggg    1860
gttggagttc ttcgaccagc cggcagtccc cctggcccgg gcatttctgg acaggtcct    1920
agtccggcga cttcctaatg gcacagaact ccgaggccgc atcgtggaga ccgaggcata    1980
cctggggcca gaggatgaag ccgcccactc aagggtggc cggcagaccc ccgcaaccg    2040
aggcatgttc atgaagccgg ggaccctgta cgtgtacatc atttacgca tgtacttctg    2100
catgaacatc tccagccagg gggacgggc ttgcgtcttg ctgcgagcac tggagcccct    2160
ggaaggtctg gagaccatgc gtcagcttcg cagcacccte cggaaaggca ccgccagccg    2220
```

```
tgtcctcaag gaccgcgagc tctgcagtgg cccctccaag ctgtgccagg ccctggccat    2280
caacaagagc tttgaccaga gggacctggc acaggatgaa gctgtatggc tggagcgtgg    2340 tccccctggag cccagtgagc cggctgtagt ggcagcagcc cgggtgggcg tcggccatgc    2400
aggggagtgg gcccggaaac ccctccgctt ctatgtccgg ggcagcccct gggtcagtgt    2460
ggtcgacaga gtggctgagc aggacacaca ggcctctaga taataacaat tcaggaggac    2520
tagtatggct tcgtacccccg gccatcaaca cgcgtctgcg ttcgaccagg ctgcgcgttc    2580
tcgcggccat agcaaccgac gtacggcgtt gcgccctcgc cggcagcaag aagccacgga    2640
agtccgcccg gagcagaaaa tgcccacgct actgcgggtt tatatagacg gtccccacgg    2700
gatggggaaa accaccacca cgcaactgct ggtggccctg ggttcgcgcg acgatatcgt    2760
ctacgtaccc gagccgatga cttactggcg ggtgctgggg gcttccgaga caatcgcgaa    2820
catctacacc acacaacacc gcctcgacca gggtgagata tcggccgggg acgcggcggt    2880
ggtaatgaca agcgcccaga taacaatggg catgccttat gccgtgaccg acgccgttct    2940
ggctcctcat atcggggggg aggctgggag ctcacatgcc ccgcccccgg ccctcaccct    3000
catcttcgac cgccatccca tcgccgccct cctgtgctac ccggccgcgc ggtaccttat    3060
gggcagcatg accccccagg ccgtgctggc gttcgtggcc ctcatcccgc cgaccttgcc    3120
cggcaccaac atcgtgcttg ggcccttcc ggaggacaga cacatcgacc gcctggccaa    3180
acgccagcgc cccggcgagc ggctggacct ggctatgctg gctgcgattc gccgcgttta    3240
cgggctactt gccaatacgg tgcggtatct gcagtgcggc gggtcgtggc gggaggactg    3300
gggacagctt tcggggacgg ccgtgccgcc ccagggtgcc gagcccccaga gcaacgcggg    3360 cccacgaccc catatcgggg acacgttatt taccctgttt cgggcccccg agttgctggc    3420
ccccaacggc gacctgtata cgtgtttgc ctgggccttg gacgtcttgg ccaaacgcct    3480
ccgttccatg cacgtctttta tcctggatta cgaccaatcg cccgccggct gccgggacgc    3540
cctgctgcaa cttacctccg ggatggtcca gacccacgtc accaccccccg gctccatacc    3600 gacgatatgc gacctggcgc gcacgttttgc ccggggagatg gggggaggcta actgaaaagct    3660 ttaatgcggt agtttatcac agttaaattg ctaacgcagt caggcaccgt gtatgctttc    3720
acagtgctag gtataggggtg ataggacagt gatcactgcc gagggccttg gaacggatct    3780
tgctgtcaca caatgcaggt aacagagagt gggacaacaa aaagtaatca aggcgccaac    3840
caacattctt ggatcgagca ttcatcatat aagtccaaaa ggtgtaggca tagggtgtgt    3900
tggggtagag gtgcctaaag ctgtcagcca gtggcacagc ctgcagtaat tccccgaagc    3960
cttggcgctc ttgtggcgtg aagccagcat tcttttttgtt ccccttgggg ttgcgaaggt    4020
caatttcttc atgtgccaca ttgaggtctc cacacagcac aagggggcttt cgggaagcca    4080 ggcccttcag gaacttgcga aaggcttcat cccagcgctg ccggtactcc agtcgtacca    4140
gacctcggcc tgcattaggt acatatgctg ttaccagcac aaacgagtca aattcagcca    4200
caatcacccg gccttcctga tcatgctcct catcgcctat gccgtaagaa actttgagtg    4260
ggcactggcg ggaaagcagg cccacgccac tgtaccccttc cttgtccgaa ggagctgacc    4320
agtattgatg agagagtcca ggcagctcct gaagttcagc tggtagtttg ttctctgaac    4380
atttggtctc ttgaaggcac agtatatctg gggcttcttc cttttacccaa tctaatcctt    4440 tcttcttaat ccaggctcga agcccatcca cattccaaga gcagatcttg agtgtggcag    4500
gtttgccact gggtgaggtt ttctgatctg gggggtcctc atacagggct gggccctctc    4560
```

| | |
|---|---|
| ctgctgcctc tttgtcattt ttctttgcgg ccgtcttact cttcttggcc tctggctctg | 4620 |
| tcctgagctc atccccgtct tccgccaccg ctccctttt cccacgcttc ggcatttata | 4680 |
| tcctcctcga ggtttcacat tcaccaccct gaattgactc tcttccgggc gctatcatgc | 4740 |
| cataccgcga aaggttttgc accattcgat ggtgtcaacg taaatgcatg ccgcttcgcc | 4800 |
| ttcgcgcgcg aattgatctg ctgcctcgcg cgtttcggtg atgacggtga aaacctctga | 4860 |
| cacatgcagc tcccggagac ggtcacagct tgtctgtaag cggatgccgg gagcagacaa | 4920 |
| gcccgtcagg gcgcgtcagc gggtgttggc gggtgtcggg gcgcagccat gacccagtca | 4980 |
| cgtagcgata gcggagtgta ggatcccgtt aagggcacc aataactgcc ttaaaaaaat | 5040 |
| tacgccccgc cctgccactc atcgcagtac tgttgtaatt cattaagcat tctgccgaca | 5100 |
| tggaagccat cacaaacggc atgatgaacc tgaatcgcca gcggcatcag caccttgtcg | 5160 |
| ccttgcgtat aatatttgcc catcgtgaaa acggggggcga agaagttgtc catattggcc | 5220 |
| acgtttaaat caaaactggt gaaactcacc cagggattgg ctgagacgaa aaacatattc | 5280 |
| tcaataaacc ctttagggaa ataggccagg ttttcaccgt aacacgccac atcttgcgaa | 5340 |
| tatatgtgta gaaactgccg gaaatcgtcg tggtattcac tccagagcga tgaaaacgtt | 5400 |
| tcagtttgct catggaaaac ggtgtaacaa gggtgaacac tatcccatat caccagctca | 5460 |
| ccgtctttca ttgccatacg | 5480 |

<210> SEQ ID NO 5
<211> LENGTH: 5256
<212> TYPE: DNA
<213> ORGANISM: artificial
<220> FEATURE:
<223> OTHER INFORMATION: Designed expression vector DNA named
    pTrc-aag(wt) containing alkyladenine DNA glycosylase (AAG) gene

<400> SEQUENCE: 5

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg caaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggtcac | 420 |
| ccccgctttg cagatgaaga aaccaaagca gttttgccga cggatggggc aaaagaagca | 480 |
| gcgaccagct agagcagggc agccacacag ctcgtccgac gcagcccagg cacctgcaga | 540 |
| gcagccacac agctcgtccg atgcagccca ggcaccttgc ccagggagc gctgcttggg | 600 |
| accgcccacc actccgggcc cataccgcag catctatttc tcaagcccaa agggccacct | 660 |
| tacccgactg gggttggagt tcttcgacca gccggcagtc ccctggccc ggcattttct | 720 |
| gggacaggtc ctagtccggc gacttcctaa tggcacagaa ctccgaggcc gcatcgtgga | 780 |
| gaccgaggca tacctggggc cagaggatga agccgcccac tcaaggggtg gccggcagac | 840 |
| ccccccgcaac cgaggcatgt tcatgaagcc ggggaccctg tacgtgtaca tcatttacgg | 900 |
| catgtacttc tgcatgaaca tctccagcca gggggacggg gcttgcgtct tgctgcgagc | 960 |
| actggagccc ctgaaggtc tggagaccat cgtcagctt cgcagcaccc tccggaaagg | 1020 |
| caccgccagc cgtgtcctca aggaccgcga gctctgcagt ggcccctcca agctgtgcca | 1080 |

```
ggccctggcc atcaacaaga gctttgacca gagggacctg gcacaggatg aagctgtatg   1140
gctggagcgt ggtcccctgg agcccagtga gccggctgta gtggcagcag cccgggtggg   1200
cgtcggccat gcaggggagt gggcccggaa acccctccgc ttctatgtcc ggggcagccc   1260
ctgggtcagt gtggtcgaca gagtggctga gcaggacaca caggcctgaa agcttacgta   1320
gaacaaaaac tcatctcaga agaggatctg aatagcgccg tcgaccatca tcatcatcat   1380
cattgagttt aaacggtctc cagcttggct gttttggcgg atgagagaag atttcagcc    1440
tgatacagat taaatcagaa cgcagaagcg gtctgataaa acagaatttg cctggcggca   1500
gtagcgcggt ggtcccacct gaccccatgc cgaactcaga agtgaaacgc cgtagcgccg   1560
atggtagtgt ggggtctccc catgcgagag tagggaactg ccaggcatca aataaaacga   1620
aaggctcagt cgaaagactg gcctttcgt tttatctgtt gtttgtcggt gaacgctctc     1680
ctgagtagga caaatccgcc gggagcggat ttgaacgttg cgaagcaacg gcccggaggg   1740
tggcgggcag gacgcccgcc ataaactgcc aggcatcaaa ttaagcagaa ggccatcctg   1800
acggatggcc ttttttgcgtt tctacaaact ctttttgttt atttttctaa atacattcaa  1860
atatgtatcc gctcatgaga caataaccct gataaatgct tcaataatat tgaaaaagga   1920
agagtatgag tattcaacat ttccgtgtcg cccttattcc cttttttgcg cattttgcc    1980
ttcctgtttt tgctcaccca gaaacgctgg tgaaagtaaa agatgctgaa gatcagttgg   2040
gtgcacgagt gggttacatc gaactggatc tcaacagcgg taagatcctt gagagttttc   2100
gccccgaaga acgttttcca atgatgagca cttttaaagt tctgctatgt ggcgcggtat   2160
tatcccgtgt tgacgccggg caagagcaac tcggtcgccg catacactat tctcagaatg   2220
acttggttga gtactcacca gtcacagaaa agcatcttac ggatggcatg acagtaagag   2280
aattatgcag tgctgccata accatgagtg ataacactgc ggccaactta cttctgacaa   2340
cgatcggagg accgaaggag ctaaccgctt ttttgcacaa catgggggat catgtaactc   2400
gccttgatcg ttgggaaccg gagctgaatg aagccatacc aaacgacgag cgtgacacca   2460
cgatgcctac agcaatggca acaacgttgc gcaaactatt aactggcgaa ctacttactc   2520
tagcttcccg gcaacaatta atagactgga tggaggcgga taaagttgca ggaccacttc   2580
tgcgctcggc ccttccggct ggctggttta ttgctgataa atctggagcc ggtgagcgtg   2640
ggtctcgcgg tatcattgca gcactggggc cagatggtaa gccctcccgt atcgtagtta   2700
tctacacgac ggggagtcag gcaactatgg atgaacgaaa tagacagatc gctgagatag   2760
gtgcctcact gattaagcat tggtaactgt cagaccaagt ttactcatat atactttaga   2820
ttgatttaaa acttcatttt taatttaaaa ggatctaggt gaagatcctt tttgataatc   2880
tcatgaccaa aatcccttaa cgtgagtttt cgttccactg agcgtcagac cccgtagaaa   2940
agatcaaagg atcttcttga gatccttttt ttctgcgcgt aatctgctgc ttgcaaacaa   3000
aaaaaccacc gctaccagcg gtggtttgtt tgccggatca agagctacca actctttttc   3060
cgaaggtaac tggcttcagc agagcgcaga taccaaatac tgtccttcta gtgtagccgt   3120
agttaggcca ccacttcaag aactctgtag caccgcctac atacctcgct ctgctaatcc   3180
tgttaccagt ggctgctgcc agtggcgata agtcgtgtct taccgggttg gactcaagac   3240
gatagttacc ggataaggcg cagcggtcgg gctgaacggg gggttcgtgc acacagccca   3300
gcttggagcg aacgacctac accgaactga gatacctaca gcgtgagcta tgagaaagcg   3360
ccacgcttcc cgaagggaga aaggcggaca ggtatccggt aagcggcagg gtcggaacag   3420
gagagcgcac gagggagctt ccaggggaa acgcctggta tctttatagt cctgtcgggt   3480
```

```
ttcgccacct ctgacttgag cgtcgatttt tgtgatgctc gtcagggggg cggagcctat    3540
ggaaaaacgc cagcaacgcg gccttttttac ggttcctggc cttttgctgg ccttttgctc    3600
acatgttctt tcctgcgtta tcccctgatt ctgtggataa ccgtattacc gcctttgagt    3660
gagctgatac cgctcgccgc agccgaacga ccgagcgcag cgagtcagtg agcgaggaag    3720
cggaagagcg cctgatgcgg tattttctcc ttacgcatct gtgcggtatt tcacaccgca    3780
tatggtgcac tctcagtaca atctgctctg atgccgcata gttaagccag tatacactcc    3840
gctatcgcta cgtgactggg tcatggctgc gccccgacac ccgccaacac ccgctgacgc    3900
gccctgacgg gcttgtctgc tcccggcatc cgcttacaga caagctgtga ccgtctccgg    3960
gagctgcatg tgtcagaggt tttcaccgtc atcaccgaaa cgcgcgaggc agcagatcaa    4020
ttcgcgcgcg aaggcgaagc ggcatgcatt tacgttgaca ccatcgaatg gtgcaaaacc    4080
tttcgcggta tggcatgata gcgcccggaa gagagtcaat tcagggtggt gaatgtgaaa    4140
ccagtaacgt tatacgatgt cgcagagtat gccggtgtct cttatcagac cgtttcccgc    4200
gtggtgaacc aggccagcca cgtttctgcg aaaacgcggg aaaaagtgga agcggcgatg    4260
gcggagctga attacattcc caaccgcgtg gcacaacaac tggcgggcaa acagtcgttg    4320
ctgattggcg ttgccacctc cagtctggcc ctgcacgcgc cgtcgcaaat tgtcgcggcg    4380
attaaatctc gcgccgatca actgggtgcc agcgtggtgg tgtcgatggt agaacgaagc    4440
ggcgtcgaag cctgtaaagc ggcggtgcac aatcttctcg cgcaacgcgt cagtgggctg    4500
atcattaact atccgctgga tgaccaggat gccattgctg tggaagctgc ctgcactaat    4560
gttccggcgt tatttcttga tgtctctgac cagacaccca tcaacagtat tattttctcc    4620
catgaagacg gtacgcgact gggcgtggag catctggtcg cattgggtca ccagcaaatc    4680
gcgctgttag cgggcccatt aagttctgtc tcggcgcgtc tgcgtctggc tggctggcat    4740
aaatatctca ctcgcaatca aattcagccg atagcggaac gggaaggcga ctggagtgcc    4800
atgtccggtt tcaacaaac catgcaaatg ctgaatgagg gcatcgttcc cactgcgatg    4860
ctggttgcca acgatcagat ggcgctgggc gcaatgcgcg ccattaccga gtccgggctg    4920
cgcgttggtg cggatatctc ggtagtggga tacgacgata ccgaagacag ctcatgttat    4980
atcccgccgt caaccaccat caaacaggat tttcgcctgc tggggcaaac cagcgtggac    5040
cgcttgctgc aactctctca gggccaggcg gtgaagggca atcagctgtt gcccgtctca    5100
ctggtgaaaa gaaaaccac cctggcgccc aatacgcaaa ccgcctctcc ccgcgcgttg    5160
gccgattcat taatgcagct ggcacgacag gtttcccgac tggaaagcgg gcagtgagcg    5220
caacgcaatt aatgtgagtt agcgcgaatt gatctg                              5256
```

<210> SEQ ID NO 6
<211> LENGTH: 6231
<212> TYPE: DNA
<213> ORGANISM: artificial
<220> FEATURE:
<223> OTHER INFORMATION: Designed expression vector DNA named
      pTrc-aag(wt)-ape1 containing alkyladenine DNA glycosylase (AAG)
      gene and AP endonuclease (APE1) gene

<400> SEQUENCE: 6

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
```

-continued

```
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatggtcac   420
ccccgctttg cagatgaaga accaaagca gttttgccga cggatggggc aaaagaagca    480
gcgaccagct agagcagggc agccacacag ctcgtccgac gcagcccagg cacctgcaga   540
gcagccacac agctcgtccg atgcagccca ggcaccttgc ccagggagc gctgcttggg    600 accgcccacc actccgggcc cataccgcag catctatttc tcaagcccaa agggccacct   660
tacccgactg gggttggagt tcttcgacca gccggcagtc cccctggccc gggcatttct   720
gggacaggtc ctagtccggc gacttcctaa tggcacagaa ctccgaggcc gcatcgtgga   780
gaccgaggca tacctggggc cagaggatga agccgcccac tcaaggggtg gccggcagac   840
cccccgcaac cgaggcatgt tcatgaagcc ggggaccctg tacgtgtaca tcatttacgg   900
catgtacttc tgcatgaaca tctccagcca gggggacggg gcttgcgtct tgctgcgagc   960
actggagccc ctggaaggtc tggagaccat gcgtcagctt cgcagcaccc tccggaaagg  1020
caccgccagc cgtgtcctca aggaccgcga gctctgcagt ggcccctcca agctgtgcca  1080
ggccctggcc atcaacaaga gctttgacca gagggacctg gcacaggatg aagctgtatg  1140
gctggagcgt ggtcccctgg agcccagtga gccggctgta gtggcagcag cccggggtggg 1200 cgtcggccat gcaggggagt gggcccggaa acccctccgc ttctatgtcc ggggcagccc  1260
ctgggtcagt gtggtcgaca gagtggctga gcaggacaca caggcctgag aattcaggag  1320
gatataaatg ccgaagcgtg ggaaaagggg agcggtggcg gaagacgggg atgagctcag  1380
gacagagcca gaggccaaga agagtaagac ggccgcaaag aaaaatgaca agaggcagc   1440 aggagagggc ccagccctgt atgaggaccc cccagatcag aaaacctcac ccagtggcaa  1500
acctgccaca ctcaagatct gctcttggaa tgtggatggg cttcgagcct ggattaagaa  1560
gaaaggatta gattgggtaa aggaagaagc cccagatata ctgtgccttc aagagaccaa  1620
atgttcagag aacaaactac cagctgaact tcaggagctg cctggactct ctcatcaata  1680
ctggtcagct ccttcggaca aggaagggta cagtggcgtg ggcctgcttt cccgccagtg  1740
cccactcaaa gtttcttacg gcataggcga tgaggagcat gatcaggaag ccgggtgat   1800 tgtggctgaa tttgactcgt tgtgctggt aacagcatat gtacctaatg caggccgagg   1860
tctggtacga ctggagtacc ggcagcgctg ggatgaagcc tttcgcaagt tcctgaaggg   1920
cctggcttcc cgaaagcccc ttgtgctgtg tggagacctc aatgtggcac atgaagaaat   1980
tgaccttcgc aaccccaagg ggaacaaaaa gaatgctggc ttcacgccac aagagcgcca   2040
aggcttcggg gaattactgc aggctgtgcc actggctgac agctttaggc acctctaccc   2100
caacacaccc tatgcctaca ccttttggac ttatatgatg aatgctcgat ccaagaatgt   2160
tggttggcgc cttgattact ttttgttgtc ccactctctg ttacctgcat tgtgtgacag   2220
caagatccgt tccaaggccc tcggcagtga tcactgtcct atcaccctat acctagcact   2280
gtgaaagctt acgtagaaca aaaactcatc tcagaagagg atctgaatag cgccgtcgac   2340
catcatcatc atcatcattg agtttaaacg gtctccagct tggctgtttt ggcggatgag   2400
agaagatttt cagcctgata cagattaaat cagaacgcag aagcggtctg ataaaacaga   2460
atttgcctgg cggcagtagc gcggtggtcc cacctgaccc catgccgaac tcagaagtga   2520
aacgccgtag cgccgatggt agtgtggggt ctccccatgc gagagtaggg aactgccagg   2580
```

```
catcaaataa aacgaaaggc tcagtcgaaa gactgggcct ttcgttttat ctgttgtttg   2640
tcggtgaacg ctctcctgag taggacaaat ccgccgggag cggatttgaa cgttgcgaag   2700
caacggcccg gagggtggcg ggcaggacgc ccgccataaa ctgccaggca tcaaattaag   2760
cagaaggcca tcctgacgga tggccttttt gcgtttctac aaactctttt tgtttatttt   2820
tctaaataca ttcaaatatg tatccgctca tgagacaata accctgataa atgcttcaat   2880
aatattgaaa aaggaagagt atgagtattc aacatttccg tgtcgccctt attccctttt   2940
ttgcggcatt ttgccttcct gttttgctc acccagaaac gctggtgaaa gtaaaagatg   3000
ctgaagatca gttgggtgca cgagtgggtt acatcgaact ggatctcaac agcggtaaga   3060
tccttgagag ttttcgcccc gaagaacgtt ttccaatgat gagcactttt aaagttctgc   3120
tatgtggcgc ggtattatcc cgtgttgacg ccgggcaaga gcaactcggt cgccgcatac   3180
actattctca gaatgacttg gttgagtact caccagtcac agaaaagcat cttacggatg   3240
gcatgacagt aagagaatta tgcagtgctg ccataaccat gagtgataac actgcggcca   3300
acttacttct gacaacgatc ggaggaccga aggagctaac cgcttttttg cacaacatgg   3360
gggatcatgt aactcgcctt gatcgttggg aaccggagct gaatgaagcc ataccaaacg   3420
acgagcgtga caccacgatg cctgtagcaa tggcaacaac gttgcgcaaa ctattaactg   3480
gcgaactact tactctagct tcccggcaac aattaataga ctggatggag gcggataaag   3540
ttgcaggacc acttctgcgc tcggcccttc cggctggctg gtttattgct gataaatctg   3600
gagccggtga gcgtgggtct cgcggtatca ttgcagcact ggggccagat ggtaagccct   3660
cccgtatcgt agttatctac acgacgggga gtcaggcaac tatggatgaa cgaaatagac   3720
agatcgctga gataggtgcc tcactgatta agcattggta actgtcagac caagtttact   3780
catatatact ttagattgat ttaaaacttc attttaatt taaaaggatc taggtgaaga   3840
tcctttttga taatctcatg accaaaatcc cttaacgtga gttttcgttc cactgagcgt   3900
cagaccccgt agaaaagatc aaaggatctt cttgagatcc ttttttctg cgcgtaatct   3960 gctgcttgca acaaaaaaa ccaccgctac cagcggtggt ttgtttgccg gatcaagagc   4020
taccaactct tttccgaag gtaactggct tcagcagagc gcagatacca atactgtcc   4080 ttctagtgta gccgtagtta ggccaccact tcaagaactc tgtagcaccg cctacatacc   4140
tcgctctgct aatcctgtta ccagtggctg ctgccagtgg cgataagtcg tgtcttaccg   4200
ggttggactc aagacgatag ttaccggata aggcgcagcg gtcgggctga acggggggtt   4260
cgtgcacaca gcccagcttg gagcgaacga cctacaccga actgagatac ctacagcgtg   4320
agctatgaga aagcgccacg cttcccgaag ggagaaaggc ggacaggtat ccggtaagcg   4380
gcagggtcgg aacaggagag cgcacagggg agcttccagg gggaaacgcc tggtatcttt   4440
atagtcctgt cgggtttcgc cacctctgac ttgagcgtcg atttttgtga tgctcgtcag   4500
gggggcggag cctatggaaa aacgccagca acgcggcctt tttacggttc ctggcctttt   4560
gctggccttt tgctcacatg ttctttcctg cgttatcccc tgattctgtg ataaccgta   4620 ttaccgcctt tgagtgagct gataccgctc gccgcagccg aacgaccgag cgcagcgagt   4680
cagtgagcga ggaagcggaa gagcgcctga tgcggtattt tctccttacg catctgtgcg   4740
gtatttcaca ccgcatatgg tgcactctca gtacaatctg ctctgatgcc gcatagttaa   4800
gccagtatac actccgctat cgctacgtga ctgggtcatg gctgcgcccc gacacccgcc   4860
aacacccgct gacgcgccct gacgggcttg tctgctcccg gcatccgctt acagacaagc   4920
```

```
tgtgaccgtc tccgggagct gcatgtgtca gaggttttca ccgtcatcac cgaaacgcgc    4980
gaggcagcag atcaattcgc gcgcgaaggc gaagcggcat gcatttacgt tgacaccatc    5040
gaatggtgca aaacctttcg cggtatggca tgatagcgcc cggaagagag tcaattcagg    5100
gtggtgaatg tgaaaccagt aacgttatac gatgtcgcag agtatgccgg tgtctcttat    5160
cagaccgttt cccgcgtggt gaaccaggcc agccacgttt ctgcgaaaac gcgggaaaaa    5220
gtggaagcgg cgatggcgga gctgaattac attcccaacc gcgtggcaca acaactggcg    5280
ggcaaacagt cgttgctgat tggcgttgcc acctccagtc tggccctgca cgcgccgtcg    5340
caaattgtcg cggcgattaa atctcgcgcc gatcaactgg gtgccagcgt ggtggtgtcg    5400
atggtagaac gaagcggcgt cgaagcctgt aaagcggcgg tgcacaatct tctcgcgcaa    5460
cgcgtcagtg ggctgatcat taactatccg ctggatgacc aggatgccat tgctgtggaa    5520
gctgcctgca ctaatgttcc ggcgttattt cttgatgtct ctgaccagac acccatcaac    5580
agtattattt tctcccatga agacggtacg cgactgggcg tggagcatct ggtcgcattg    5640
ggtcaccagc aaatcgcgct gttagcgggc ccattaagtt ctgtctcggc gcgtctgcgt    5700
ctggctggct ggcataaata tctcactcgc aatcaaattc agccgatagc ggaacgggaa    5760
ggcgactgga gtgccatgtc cggttttcaa caaaccatga aaatgctgaa tgagggcatc    5820
gttcccactg cgatgctggt tgccaacgat cagatggcgc tgggcgcaat gcgcgccatt    5880
accgagtccg ggctgcgcgt tggtgcggat atctcggtag tgggatacga cgataccgaa    5940
gacagctcat gttatatccc gccgtcaacc accatcaaac aggattttcg cctgctgggg    6000
caaaccagcg tggaccgctt gctgcaactc tctcagggcc aggcggtgaa gggcaatcag    6060
ctgttgcccg tctcactggt gaaaagaaaa accaccctgg cgcccaatac gcaaaccgcc    6120
tctccccgcg cgttggccga ttcattaatg cagctggcac gacaggtttc ccgactgaaa    6180
agcgggcagt gagcgcaacg caattaatgt gagttagcgc gaattgatct g              6231
```

<210> SEQ ID NO 7
<211> LENGTH: 5316
<212> TYPE: DNA
<213> ORGANISM: artificial
<220> FEATURE:
<223> OTHER INFORMATION: Designed expression vector DNA named pTrc-ape1 containing AP endonuclease (APE1) gene

<400> SEQUENCE: 7

```
gtttgacagc ttatcatcga ctgcacggtg caccaatgct tctggcgtca ggcagccatc      60
ggaagctgtg tgatggctgt gcaggtcgta aatcactgca taattcgtgt cgctcaaggc     120
gcactcccgt tctggataat gttttttgcg ccgacatcat aacggttctg caaatattc     180 tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggcgaa     420
gcgtgggaaa aagggagcgg tggcggaaga cggggatgag ctcaggacag agccagaggc     480
caagaagagt aagacggccg caaagaaaaa tgacaaagag gcagcaggag agggcccagc     540
cctgtatgag gacccccag atcagaaaac ctcacccagt ggcaaacctg ccacactcaa     600
gatctgctct tggaatgtgg atgggcttcg agcctggatt aagaagaaag gattagattg     660
ggtaaaggaa gaagccccag atatactgtg ccttcaagag accaaatgtt cagagaacaa     720
```

```
actaccagct gaacttcagg agctgcctgg actctctcat caatactggt cagctccttc      780
ggacaaggaa gggtacagtg gcgtgggcct gctttcccgc cagtgcccac tcaaagtttc      840
ttacggcata ggcgatgagg agcatgatca ggaaggccgg gtgattgtgg ctgaatttga      900
ctcgtttgtg ctggtaacag catatgtacc taatgcaggc cgaggtctgg tacgactgga      960
gtaccggcag cgctgggatg aagcctttcg caagttcctg aagggcctgg cttcccgaaa     1020
gccccttgtg ctgtgtggag acctcaatgt ggcacatgaa gaaattgacc ttcgcaaccc     1080 caagggggaac aaaaagaatg ctggcttcac gccacaagag cgccaaggct cggggaatt     1140 actgcaggct gtgccactgg ctgacagctt taggcacctc taccccaaca cacctatgc      1200 ctacaccttt tggacttata tgatgaatgc tcgatccaag aatgttggtt ggcgccttga     1260
ttactttttg ttgtcccact ctctgttacc tgcattgtgt gacagcaaga tccgttccaa     1320
ggccctcggc agtgatcact gtcctatcac cctataccta gcactgtgaa agcttacgta     1380
gaacaaaaac tcatctcaga agaggatctg aatagcgccg tcgaccatca tcatcatcat     1440
cattgagttt aaacggtctc cagcttggct gttttggcgg atgagagaag attttcagcc     1500
tgatacagat taaatcagaa cgcagaagcg gtctgataaa acagaatttg cctggcggca     1560
gtagcgcggt ggtcccacct gaccccatgc cgaactcaga agtgaaacgc cgtagcgccg     1620
atggtagtgt ggggtctccc catgcgagag tagggaactg ccaggcatca aataaaacga     1680
aaggctcagt cgaaagactg gcctttcgt tttatctgtt gtttgtcggt gaacgctctc      1740
ctgagtagga caaatccgcc gggagcggat ttgaacgttg cgaagcaacg gcccggaggg     1800
tggcgggcag gacgcccgcc ataaactgcc aggcatcaaa ttaagcagaa ggccatcctg     1860
acggatggcc tttttgcgtt tctacaaact cttttgtttt attttctaa atacattcaa      1920 atatgtatcc gctcatgaga caataaccct gataaatgct tcaataatat tgaaaaagga     1980
agagtatgag tattcaacat ttccgtgtcg cccttattcc cttttttgcg cattttgcc      2040 ttcctgttttt tgctcaccca gaaacgctgg tgaaagtaaa agatgctgaa gatcagttgg     2100
gtgcacgagt gggttacatc gaactggatc tcaacagcgg taagatcctt gagagtttc     2160 gccccgaaga cgttttcca atgatgagca cttttaaagt tctgctatgt ggcgcggtat     2220
tatcccgtgt tgacgccggg caagagcaac tcggtcgccg catacactat tctcagaatg     2280
acttggttga gtactcacca gtcacagaaa agcatcttac ggatggcatg acagtaagag     2340
aattatgcag tgctgccata accatgagtg ataacactgc ggccaactta cttctgacaa     2400
cgatcggagg accgaaggag ctaaccgctt ttttgcacaa catgggggat catgtaactc     2460
gccttgatcg ttgggaaccg gagctgaatg aagccatacc aaacgacgag cgtgacacca     2520
cgatgcctgt agcaatggca acaacgttgc gcaaactatt aactggcgaa ctacttactc     2580
tagcttcccg gcaacaatta atagactgga tggaggcgga taaagttgca ggaccacttc     2640
tgcgctcggc ccttccggct ggctggttta ttgctgataa atctggagcc ggtgagcgtg     2700
ggtctcgcgg tatcattgca gcactggggc cagatggtaa gccctcccgt atcgtagtta     2760
tctacacgac ggggagtcag gcaactatgg atgaacgaaa tagacagatc gctgagatag     2820
gtgcctcact gattaagcat tggtaactgt cagaccaagt ttactcatat atactttaga     2880
ttgatttaaa acttcatttt taatttaaaa ggatctaggt gaagatcctt tttgataatc     2940
tcatgaccaa aatcccttaa cgtgagtttt cgttccactg agcgtcagac cccgtagaaa     3000
agatcaaagg atcttcttga gatcctttt ttctgcgcgt aatctgctgc ttgcaaacaa     3060
aaaaaccacc gctaccagcg gtggtttgtt tgccggatca agagctacca actctttttc     3120
```

```
cgaaggtaac tggcttcagc agagcgcaga taccaaatac tgtccttcta gtgtagccgt    3180
agttaggcca ccacttcaag aactctgtag caccgcctac atacctcgct ctgctaatcc    3240
tgttaccagt ggctgctgcc agtggcgata agtcgtgtct taccggggttg gactcaagac   3300 gatagttacc ggataaggcg cagcggtcgg gctgaacggg gggttcgtgc acacagccca    3360
gcttggagcg aacgacctac accgaactga gatacctaca gcgtgagcta tgagaaagcg    3420
ccacgcttcc cgaagggaga aaggcggaca ggtatccggt aagcggcagg gtcggaacag    3480
gagagcgcac gagggagctt ccaggggaa acgcctggta tctttatagt cctgtcgggt     3540
ttcgccacct ctgacttgag cgtcgatttt tgtgatgctc gtcaggggg cggagcctat     3600 ggaaaaacgc cagcaacgcg gcctttttac ggttcctggc cttttgctgg ccttttgctc    3660
acatgttctt cctgcgtta tcccctgatt ctgtggataa ccgtattacc gcctttgagt     3720
gagctgatac cgctcgccgc agccgaacga ccgagcgcag cgagtcagtg agcgaggaag    3780
cggaagagcg cctgatgcgg tattttctcc ttacgcatct gtgcggtatt tcacaccgca    3840
tatggtgcac tctcagtaca atctgctctg atgccgcata gttaagccag tatacactcc    3900
gctatcgcta cgtgactggg tcatggctgc gccccgacac ccgccaacac ccgctgacgc    3960
gccctgacgg gcttgtctgc tcccggcatc cgcttacaga caagctgtga ccgtctccgg    4020
gagctgcatg tgtcagaggt tttcaccgtc atcaccgaaa cgcgcgaggc agcagatcaa    4080
ttcgcgcgcg aaggcgaagc ggcatgcatt tacgttgaca ccatcgaatg gtgcaaaacc    4140
tttcgcggta tggcatgata gcgcccggaa gagagtcaat tcagggtggt gaatgtgaaa    4200
ccagtaacgt tatacgatgt cgcagagtat gccggtgtct cttatcagac cgtttcccgc    4260
gtggtgaacc aggccagcca cgtttctgcg aaaacgcggg aaaaagtgga agcggcgatg    4320
gcggagctga attacattcc caaccgcgtg gcacaacaac tggcgggcaa acagtcgttg    4380
ctgattggcg ttgccacctc cagtctggcc ctgcacgcgc cgtcgcaaat tgtcgcggcg    4440
attaaatctc gcgccgatca actgggtgcc agcgtggtgg tgtcgatggt agaacgaagc    4500
ggcgtcgaag cctgtaaagc ggcggtgcac aatcttctcg cgcaacgcgt cagtgggctg    4560
atcattaact atccgctgga tgaccaggat gccattgctg tggaagctgc ctgcactaat    4620
gttccggcgt tatttcttga tgtctctgac cagacaccca tcaacagtat tattttctcc    4680
catgaagacg gtacgcgact gggcgtggag catctggtcg cattgggtca ccagcaaatc    4740
gcgctgttag cgggcccatt aagttctgtc tcggcgcgtc tgcgtctggc tggctggcat    4800
aaatatctca ctcgcaatca aattcagccg atagcggaac gggaaggcga ctggagtgcc    4860
atgtccggtt ttcaacaaac catgcaaatg ctgaatgagg gcatcgttcc cactgcgatg    4920
ctggttgcca acgatcagat ggcgctgggc gcaatgcgcg ccattaccga gtccgggctg    4980
cgcgttggtg cggatatctc ggtagtggga tacgacgata ccgaagacag ctcatgttat    5040
atcccgccgt caaccaccat caaacaggat tttcgcctgc tggggcaaac cagcgtggac    5100
cgcttgctgc aactctctca gggccaggcg gtgaagggca atcagctgtt gcccgtctca    5160
ctggtgaaaa gaaaaaccac cctggcgccc aatacgcaaa ccgcctctcc ccgcgcgttg    5220
gccgattcat taatgcagct ggcacgacag gtttcccgac tggaaagcgg gcagtgagcg    5280
caacgcaatt aatgtgagtt agcgcgaatt gatctg                             5316
```

<210> SEQ ID NO 8
<211> LENGTH: 5049
<212> TYPE: DNA

<213> ORGANISM: artificial
<220> FEATURE:
<223> OTHER INFORMATION: Designed expression vector DNA named pCI-gfp containing Green Fluorescens Protein (GFP) gene

<400> SEQUENCE: 8

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa agttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aacccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttcaaga tttcagtgca    1440
atttatctct tcaaatgtag cacctgaagt cagccccata cgatataagt tgtaattctc    1500
atgtttgaca gcttatcatc gattaacacc gtgcgtgttg actatttac ctctggcggt    1560
gataatggtt gctactagag aaagaggaga atactagcc atgggatga gtaaaggaga    1620
agaacttttc actggagttg tcccaattct tgttgaatta gatggtgatg ttaatgggca    1680
caaattttct gtcagtggag agggtgaagg tgatgcaaca tacggaaaac ttaccctttaa    1740
atttatttgc actactggaa aactacctgt tccgtggcca acacttgtca ctactttctc    1800
ttatggtgtt caatgctttt cccgttatcc ggatcatatg aaacggcatg acttttttcaa    1860
gagtgccatg cccgaaggtt atgtacagga acgcactata tctttcaaag atgacgggaa    1920
ctacaagacg cgtgctgaag tcaagtttga aggtgatacc cttgttaatc gtatcgagtt    1980
aaaaggtatt gattttaaag aagatggaaa cattctcgga cacaaactcg agtacaacta    2040
taactcacac aatgtataca tcacggcaga caaacaaaag aatggaatca aagctaactt    2100
caaaattcgc cacaacattg aagatggatc cgttcaacta gcagaccatt atcaacaaaa    2160
```

```
tactccaatt ggcgatggcc ctgtccttt  accagacaac cattacctgt cgacacaatc   2220 tgcccttttcg aaagatccca acgaaaagcg tgaccacatg gtccttcttg agtttgtaac   2280
tgctgctggg attacacatg gcatggatga gctctacaaa taactgaaag ctttaatgcg   2340
gtagtttatc acagttaaat tgctaacgca gtcaggcacc gtgtatgaaa tctaacaatg   2400
cgctcatcgt catcctcggc accgtcaccc tggatgctgt aggcataggc ttggttatgc   2460
cggtactgcc gggcctcttg cgggatatcg tccattccga cagcatcgcc agtcactatg   2520
gcgtgctgct agcgctatat gcgttgatgc aatttctatg cgcacccgtt ctcggagcac   2580
tgtccgaccg ctttggccgc cgcccagtcc tgctcgcttc gctacttgga gccactatcg   2640
actacgcgat catggcgacc acacccgtcc tgtggatcct ctacgccgga cgcatcgtgg   2700
ccggcatcac cggcgccaca ggtgcggttg ctggcgccta tcgccgac   atcaccgatg   2760 gggaagatcg ggctcgccac ttcgggctca tgagcgcttg tttcggcgtg ggtatggtgg   2820
caggccccgt ggccgggga  ctgttgggcg ccatctcctt gcatgcacca ttccttgcgg   2880
cggcggtgct caacggcctc aacctactac tgggctgctt cctaatgcag gagtcgcata   2940
agggagagcg tcgaccgatg cccttgagag ccttcaaccc agtcagctcc ttccggtggg   3000
cgcggggcat gactatcgtc gccgcactta tgactgtctt ctttatcatg caactcgtag   3060
gacaggtgcc ggcagcgctc tgggtcattt tcggcgagga ccgcttcgc  tggagcgcga   3120 cgatgatcgg cctgtcgctt gcggtattcg gaatcttgca cgccctcgct caagccttcg   3180
tcactggtcc cgccaccaaa cgtttcggcg agaagcaggc cattatcgcc ggcatggcgg   3240
ccgacgcgct gggctacgtc ttgctggcgt tcgcgacgcg aggctggatg gccttcccca   3300
ttatgattct tctcgcttcc ggcggcatcg ggatgcccgc gttgcaggcc atgctgtcca   3360
ggcaggtaga tgacgaccat cagggacagc ttcaaggatc gctcgcggct cttaccagcc   3420
taacttcgat cactggaccg ctgatcgtca cggcgattta tgccgcctcg gcgagcacat   3480
ggaacgggtt ggcatggatt gtaggcgccg ccctatacct tgtctgcctc cccgcgttgc   3540
gtcgcggtgc atggagccgg gccacctcga cctgaatgga agccggcggc acctcgctaa   3600
cggattcacc actccaagaa ttggagccaa tcaattcttg cggagaactg tgaatgcgca   3660
aaccaaccct tggcagaaca tatccatcgc gtccgccatc tccagcagcc gcacgcggcg   3720
catctcgggc agcgttgggt cctggccacg ggtgcgcatg atcgtgctcc tgtcgttgag   3780
gacccggcta ggctggcggg gttgccttac tggttagcag aatgaatcac cgatacgcga   3840
gcgaacgtga agcgactgct gctgcaaaac gtctgcgacc tgagcaacaa catgaatggt   3900
cttcggtttc cgtgtttcgt aaagtctgga aacgcggaag tccctacgt  gctgctgaag   3960 ttgcccgcaa cagagagtgg aaccaaccgg tgataccacg atactatgac tgagagtcaa   4020
cgccatgagc ggcctcattt cttattctga gttacaacag tccgcaccgc tgtccggtag   4080
ctccttccgg tgggcgcggg gcatgactat cgtcgccgca cttatgactg tcttctttat   4140
catgcaactc gtaggacagg tgccggcagc gcccaacagt ccccggcca  cggggcctgc   4200 caccatatccc acgccgaaac aagcgccctg caccattatg ttccggatct gcatcgcagg   4260
atgctgctgg ctaccctgtg gaacacctac atctgtatta acgaagcgct aaccgttttt   4320
atcaggctct gggaggcaga ataaatgatc atatcgtcaa ttattacctc cacggggaga   4380
gcctgagcaa actggcctca ggcatttgag aagcacacgg tcacactgct tccggtagtc   4440
aataaaccgg taaccagca  atagacataa gcggctattt aacgaccctg ccctgaaccg   4500
acgaccgggt cgaatttgct ttcgaatttc tgccattcat ccgcttatta tcacttattc   4560
```

```
aggcgtagca ccaggcgttt aagggcacca ataactgcct taaaaaaatt acgccccgcc    4620
ctgccactca tcgcagtact gttgtaattc attaagcatt ctgccgacat ggaagccatc    4680
acaaacggca tgatgaacct gaatcgccag cggcatcagc accttgtcgc cttgcgtata    4740
atatttgccc atcgtgaaaa cggggcgaa gaagttgtcc atattggcca cgtttaaatc    4800
aaaactggtg aaactcaccc agggattggc tgagacgaaa acatattct caataaaccc     4860 tttagggaaa taggccaggt tttcaccgta acacgccaca tcttgcgaat atatgtgtag    4920
aaactgccgg aaatcgtcgt ggtattcact ccagagcgat gaaaacgttt cagtttgctc    4980
atggaaaacg gtgtaacaag ggtgaacact atcccatatc accagctcac cgtctttcat    5040
tgccatacg                                                            5049
```

<210> SEQ ID NO 9
<211> LENGTH: 6239
<212> TYPE: DNA
<213> ORGANISM: artificial
<220> FEATURE:
<223> OTHER INFORMATION: Designed expression vector DNA having genetic
      circuit A

<400> SEQUENCE: 9

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgagcgg    420
atacatattt gaatgtattt agaaaaataa acaataggg gttccgcgca catttccccg    480
aaaagtgcca cctgacgtct aagaaaccat tattatcatg aaaaacataa atgccgacga    540
cacatacaga ataattaata aaattaaggc ttgtagaagc aataatgata ttaatcaatg    600
cttatctgat atgactaaaa tggtacattg tgaatattat ttactcgcga tcatttatcc    660
tcattctatg gttaaatctg atatttcaat cctagataat tacccctaaaa aatgggaggca    720 atattatgat gacgctaatt taataaaata tgatcctata gtagattatt ctaactccaa    780
tcattcacca attaattgga atatatttga aaacaatgct gtaaataaaa aatctccaaa    840
tgtaattaaa gaagcgaaaa catcaggtct tatcactggg tttagtttcc ctattcatac    900
ggctaacaat ggcttcggaa tgcttagttt tgcacattca gaaaagaca actatataga    960 tagtttattt ttacatgcgt gtatgaacat accattaatt gttccttctc tagttgataa    1020
ttatcgaaaa ataaatatag caaataataa atcaaacaac gatttaacca aaagagaaaa    1080
agaatgttta gcgtgggcat gcgaaggaaa aagctcttgg gatatttcaa aaatattagg    1140
ttgcagtgag cgtactgtca ctttccattt aaccaatgcg caaatgaaac tcaatacaac    1200
aaaccgctgc caaagtattt ctaaagcaat tttaacagga gcaattgatt gcccatactt    1260
taaaaattaa taacactgat agtgctagtg tagatcacta ctagagccag gcatcaaata    1320
aaacgaaagg ctcagtcgaa agactgggcc tttcgtttta tctgttgttt gtcggtgaac    1380
gctctctact agagtcacac tggctcacct tcggtgggc ctttctgcgt ttatatacta    1440
gagacctgta ggatcgtaca ggtttacgca agaaaatggt ttgttatagt cgaataaata    1500
```

```
ctagagaaag aggagaaata ctagccatga gcacaaaaaa gaaaccatta acacaagagc   1560
agcttgagga cgcacgtcgc cttaaagcaa tttatgaaaa aaagaaaaat gaacttggct   1620
tatcccagga atctgtcgca gacaagatgg ggatggggca gtcaggcgtt ggtgctttat   1680
ttaatggcat caatgcatta aatgcttata acgccgcatt gcttgcaaaa attctcaaag   1740
ttagcgttga agaatttagc ccttcaatcg ccagagaaat ctacgagatg tatgaagcgg   1800
ttagtatgca gccgtcactt agaagtgagt atgagtaccc tgttttttct catgttcagg   1860
cagggatgtt ctcacctgag cttagaacct ttaccaaagg tgatgcggag agatgggtaa   1920
gcacaaccaa aaaagccagt gattctgcat tctggcttga ggttgaaggt aattccatga   1980
ccgcaccaac aggctccaag ccaagctttc ctgacggaat gttaattctc gttgaccctg   2040
agcaggctgt tgagccaggt gatttctgca tagccagact tgggggtgat gagtttacct   2100
tcaagaaact gatcagggat agcggtcagg tgttttttaca accactaaac ccacagtacc   2160
caatgatccc atgcaatgag agttgttccg ttgtggggaa agttatcgct agtcagtggc   2220
ctgaagagac gtttggcgct gcataataat ctagacccca ttacacatgg catggatgag   2280
ctctacaaat aaaagcttac gtagaacaaa aactcatctc agaagaggat ctgaatagcg   2340
ccgtcgacca tcatcatcat catcattgag tttaaacggt ctccagcttg gctgttttgg   2400
cggatgagag aagattttca gcctgataca gattaaatca gaacgcagaa gcggtctgat   2460
aaaacagaat ttgcctggcg gcagtagcgc ggtggtccca cctgacccca tgccgaactc   2520
agaagtgaaa cgccgtagcg ccgatggtag tgtgggtct ccccatgcga gagtagggaa   2580
ctgccaggca tcaaataaaa cgaaaggctc agtcgaaaga ctgggccttt cgttttatct   2640
gttgtttgtc ggtgaacgct ctcctgagta ggacaaatcc gccgggagcg atttgaacg   2700 ttgcgaagca acggcccgga gggtggcggg caggacgccc gccataaact gccaggcatc   2760
aaattaagca gaaggccatc ctgacggatg ccttttttgc gtttctacaa actctttttg   2820 tttattttc taaatacatt caaatatgta tccgctcatg agacaataac cctgataaat   2880
gcttcaataa tattgaaaaa ggaagagtat gagtattcaa catttccgtg tcgcccttat   2940 tcccttttt gcggcatttt gccttcctgt ttttgctcac ccagaaacgc tggtgaaagt   3000
aaaagatgct gaagatcagt tgggtgcacg agtgggttac atcgaactgg atctcaacag   3060
cggtaagatc cttgagagtt ttcgccccga agaacgtttt ccaatgatga gcacttttaa   3120
agttctgcta tgtggcgcgg tattatcccg tgttgacgcc gggcaagagc aactcggtcg   3180
ccgcatacac tattctcaga atgacttggt tgagtactca ccagtcacag aaaagcatct   3240
tacggatggc atgacagtaa gagaattatg cagtgctgcc ataaccatga gtgataacac   3300
tgcggccaac ttacttctga caacgatcgg aggaccgaag gagctaaccg cttttttgca   3360
caacatgggg gatcatgtaa ctcgccttga tcgttgggaa ccggagctga atgaagccat   3420
accaaacgac gagcgtgaca ccacgatgcc tacagcaatg gcaacaacgt tgcgcaaact   3480
attaactggc gaactactta ctctagcttc ccggcaacaa ttaatagact ggatggaggc   3540
ggataaagtt gcaggaccac ttctgcgctc ggcccttccg gctggctggt ttattgctga   3600
taaatctgga gccggtgagc gtgggtctcg cggtatcatt gcagcactgg ggccagatgg   3660
taagccctcc cgtatcgtag ttatctacac gacgggagt caggcaacta tggatgaacg   3720
aaatagacag atcgctgaga taggtgcctc actgattaag cattggtaac tgtcagacca   3780
agtttactca tatatacttt agattgattt aaaacttcat ttttaattta aaaggatcta   3840
```

```
ggtgaagatc cttttttgata atctcatgac caaaatccct taacgtgagt tttcgttcca    3900
ctgagcgtca gaccccgtag aaaagatcaa aggatcttct tgagatcctt tttttctgcg    3960
cgtaatctgc tgcttgcaaa caaaaaaacc accgctacca gcggtggttt gtttgccgga    4020
tcaagagcta ccaactcttt ttccgaaggt aactggcttc agcagagcgc agataccaaa    4080
tactgtcctt ctagtgtagc cgtagttagg ccaccacttc aagaactctg tagcaccgcc    4140
tacataccte gctctgctaa tcctgttacc agtggctgct gccagtggcg ataagtcgtg    4200
tcttaccggg ttggactcaa gacgatagtt accggataag gcgcagcggt cgggctgaac    4260
ggggggttcg tgcacacagc ccagcttgga gcgaacgacc tacaccgaac tgagatacct    4320
acagcgtgag ctatgagaaa gcgccacgct tcccgaaggg agaaaggcgg acaggtatcc    4380
ggtaagcggc agggtcggaa caggagagcg cacgagggag cttccagggg gaaacgcctg    4440
gtatctttat agtcctgtcg ggtttcgcca cctctgactt gagcgtcgat ttttgtgatg    4500
ctcgtcaggg gggcggagcc tatggaaaaa cgccagcaac gcggcctttt tacggttcct    4560
ggccttttgc tggccttttg ctcacatgtt ctttcctgcg ttatcccctg attctgtgga    4620
taaccgtatt accgcctttg agtgagctga taccgctcgc cgcagccgaa cgaccgagcg    4680
cagcgagtca gtgagcgagg aagcggaaga gcgcctgatg cggtattttc tccttacgca    4740
tctgtgcggt atttcacacc gcatatggtg cactctcagt acaatctgct ctgatgccgc    4800
atagttaagc cagtatacac tccgctatcg ctacgtgact gggtcatggc tgcgccccga    4860
cacccgccaa cacccgctga cgcgccctga cgggcttgtc tgctcccggc atccgcttac    4920
agacaagctg tgaccgtctc cgggagctgc atgtgtcaga ggttttcacc gtcatcaccg    4980
aaacgcgcga ggcagcagat caattcgcgc gcgaaggcga agcggcatgc atttacgttg    5040
acaccatcga atggtgcaaa acctttcgcg gtatggcatg atagcgcccg gaagagagtc    5100
aattcagggt ggtgaatgtg aaaccagtaa cgttatacga tgtcgcagag tatgccggtg    5160
tctcttatca gaccgtttcc cgcgtggtga accaggccag ccacgtttct gcgaaaacgc    5220
gggaaaaagt ggaagcggcg atggcggagc tgaattacat tcccaaccgc gtggcacaac    5280
aactggcggg caaacagtcg ttgctgattg gcgttgccac ctccagtctg gccctgcacg    5340
cgccgtcgca aattgtcgcg gcgattaaat ctcgcgccga tcaactgggt gccagcgtgg    5400
tggtgtcgat ggtagaacga agcggcgtcg aagcctgtaa agcggcggtg cacaatcttc    5460
tcgcgcaacg cgtcagtggg ctgatcatta actatccgct ggatgaccag gatgccattg    5520
ctgtggaagc tgcctgcact aatgttccgg cgttatttct tgatgtctct gaccagacac    5580
ccatcaacag tattatttc tcccatgaag acggtacgcg actgggcgtg gagcatctgg    5640
tcgcattggg tcaccagcaa atcgcgctgt tagcgggccc attaagttct gtctcggcgc    5700
gtctgcgtct ggctggctgg cataaatatc tcactcgcaa tcaaattcag ccgatagcgg    5760
aacgggaagg cgactggagt gccatgtccg gttttcaaca aaccatgcaa atgctgaatg    5820
agggcatcgt tcccactgcg atgctggttg ccaacgatca gatggcgctg ggcgcaatgc    5880
gcgccattac cgagtccggg ctgcgcgttg gtgcggatat ctcggtagtg ggatacgacg    5940
ataccgaaga cagctcatgt tatatcccgc cgtcaaccac catcaaacag gattttcgcc    6000
tgctggggca aaccagcgtg gaccgcttgc tgcaactctc tcagggccag gcggtgaagg    6060
gcaatcagct gttgccegtc tcactggtga aagaaaaaac cacccetggcg cccaatacgc    6120
aaaccgcctc tccccgcgcg ttggccgatt cattaatgca gctggcacga caggtttccc    6180
gactggaaag cgggcagtga gcgcaacgca attaatgtga gttagcgcga attgatctg    6239
```

<210> SEQ ID NO 10
<211> LENGTH: 5949
<212> TYPE: DNA
<213> ORGANISM: artificial
<220> FEATURE:
<223> OTHER INFORMATION: Designed expression vector DNA having genetic circuit B

<400> SEQUENCE: 10

```
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc       120
gcactcccgt tctggataat gttttttgcg ccgacatcat aacggttctg gcaaatattc       180
tgaaatgagc tgttgacaat taatcatccg gctcgtataa tgtgtggaat tgtgagcgga       240
taacaatttc acacaggaaa cagcgccgct gagaaaaagc gaagcggcac tgctctttaa       300
caatttatca gacaatctgt gtgggcactc gaccggaatt atcgattaac tttattatta       360
aaaattaaag aggtatatat taatgtatcg attaaataag gaggaataaa ccatgagcgg       420
atacatattt gaatgtattt agaaaaataa acaataggg gttccgcgca catttccccg        480
aaaagtgcca cctgacgtct aagaaaccat tattatcatg aaaaacataa atgccgacga       540
cacatacaga ataattaata aaattaaggc ttgtagaagc aataatgata ttaatcaatg       600
cttatctgat atgactaaaa tggtacattg tgaatattat ttactcgcga tcatttatcc       660
tcattctatg gttaaatctg atatttcaat cctagataat taccctaaaa atggaggca        720
atattatgat gacgctaatt taataaaata tgatcctata gtagattatt ctaactccaa       780
tcattcacca attaattgga atatatttga aaacaatgct gtaaataaaa atctccaaa        840
tgtaattaaa gaagcgaaaa catcaggtct tatcactggg tttagtttcc ctattcatac       900
ggctaacaat ggcttcggaa tgcttagttt tgcacattca gaaaaagaca actatataga       960
tagtttattt ttcatgcgt gtatgaacat accattaatt gttccttctc tagttgataa      1020
ttatcgaaaa ataaatatag caaataataa atcaaacaac gatttaacca aaagagaaaa      1080
agaatgttta gcgtgggcat gcgaaggaaa aagctcttgg gatatttcaa aaatattagg      1140
ttgcagtgag cgtactgtca ctttccattt aaccaatgcg caaatgaaac tcaatacaac      1200
aaaccgctgc caaagtattt ctaaagcaat tttaacagga gcaattgatt gcccatactt      1260
taaaaattaa taacactgat agtgctagtg tagatcacta ctagagccag gcatcaaata      1320
aaacgaaagg ctcagtcgaa agactgggcc tttcgtttta tctgttgttt gtcggtgaac      1380
gctctctact agagtcacac tggctcacct tcgggtgggc ctttctgcgt ttatatacta      1440
gagacctgta ggatcgtaca ggtttacgca agaaaatggt ttgttatagt cgaataaata      1500
ctagagaaag aggagaaata ctagccatga gcacaaaaaa gaaaccatta acacaagagc      1560
agcttgagga cgcacgtcgc cttaaagcaa tttatgaaaa aagaaaaat gaacttggct      1620
tatcccagga atctgtcgca gacaagatgg ggatggggca gtcaggcgtt ggtgctttat      1680
ttaatggcat caatgcatta aatgcttata cgccgcatt gcttgcaaaa attctcaaag      1740
ttagcgttga agaatttagc ccttcaatcg ccagagaaat ctacgagatg tatgaagcgg      1800
ttagtatgca gccgtcactt agaagtgagt atgagtaccc tgttttttct catgttcagg      1860
cagggatgtt ctcacctgag cttagaacct ttaccaaagg tgatgcggag agatgggtaa      1920
gcacaaccaa aaaagccagt gattctgcat tctggcttga ggttgaaggt aattccatga      1980
ccgcaccaac aggctccaag ccaagcttac gtagaacaaa aactcatctc agaagaggat      2040
```

```
ctgaatagcg ccgtcgacca tcatcatcat catcattgag tttaaacggt ctccagcttg    2100
gctgttttgg cggatgagag aagattttca gcctgataca gattaaatca gaacgcagaa    2160
gcggtctgat aaaacagaat ttgcctggcg gcagtagcgc ggtggtccca cctgacccca    2220
tgccgaactc agaagtgaaa cgccgtagcg ccgatggtag tgtggggtct ccccatgcga    2280
gagtagggaa ctgccaggca tcaaataaaa cgaaaggctc agtcgaaaga ctgggccttt    2340
cgttttatct gttgtttgtc ggtgaacgct ctcctgagta ggacaaatcc gccgggagcg    2400
gatttgaacg ttgcgaagca acggcccgga gggtggcggg caggacgccc gccataaact    2460
gccaggcatc aaattaagca gaaggccatc ctgacggatg gcctttttgc gtttctacaa    2520 actcttttg tttatttttc taaatacatt caaatatgta tccgctcatg agacaataac    2580
cctgataaat gcttcaataa tattgaaaaa ggaagagtat gagtattcaa catttccgtg    2640
tcgcccttat ccctttttt gcggcatttt gccttcctgt ttttgctcac ccagaaacgc    2700
tggtgaaagt aaaagatgct gaagatcagt tgggtgcacg agtgggttac atcgaactgg    2760
atctcaacag cggtaagatc cttgagagtt ttcgccccga gaacgttttt ccaatgatga    2820
gcacttttaa agttctgcta tgtggcgcgg tattatcccg tgttgacgcc gggcaagagc    2880
aactcggtcg ccgcatacac tattctcaga atgacttggt tgagtactca ccagtcacag    2940
aaaagcatct tacggatggc atgacagtaa gagaattatg cagtgctgcc ataaccatga    3000
gtgataacac tgcggccaac ttacttctga caacgatcgg aggaccgaag gagctaaccg    3060
cttttttgca caacatgggg gatcatgtaa ctcgccttga tcgttgggaa ccggagctga    3120
atgaagccat accaaacgac gagcgtgaca ccacgatgcc tacagcaatg gcaacaacgt    3180
tgcgcaaact attaactggc gaactactta ctctagcttc ccggcaacaa ttaatagact    3240
ggatggaggc ggataaagtt gcaggaccac ttctgcgctc ggcccttccg gctggctggt    3300
ttattgctga taaatctgga gccggtgagc gtgggtctcg cggtatcatt gcagcactgg    3360
ggccagatgg taagccctcc cgtatcgtag ttatctacac gacggggagt caggcaacta    3420
tggatgaacg aaatagacag atcgctgaga taggtgcctc actgattaag cattggtaac    3480
tgtcagacca agtttactca tatatacttt agattgattt aaaacttcat ttttaattta    3540
aaaggatcta ggtgaagatc ctttttgata atctcatgac caaaatccct taacgtgagt    3600
tttcgttcca ctgagcgtca gacccgtag aaaagatcaa aggatcttct tgagatcctt    3660
tttttctgcg cgtaatctgc tgcttgcaaa caaaaaaacc accgctacca gcggtggttt    3720
gtttgccgga tcaagagcta ccaactcttt ttccgaaggt aactggcttc agcagagcgc    3780
agataccaaa tactgtcctt ctagtgtagc cgtagttagg ccaccacttc aagaactctg    3840
tagcaccgcc tacatacctc gctctgctaa tcctgttacc agtggctgct gccagtggcg    3900
ataagtcgtg tcttaccggg ttggactcaa gacgatagtt accggataag gcgcagcggt    3960
cgggctgaac ggggggttcg tgcacacagc ccagcttgga gcgaacgacc tacaccgaac    4020
tgagatacct acagcgtgag ctatgagaaa gcgccacgct tcccgaaggg agaaaggcgg    4080
acaggtatcc ggtaagcggc agggtcggaa caggagagcg cacgagggag cttccagggg    4140
gaaacgcctg gtatctttat agtcctgtcg ggtttcgcca cctctgactt gagcgtcgat    4200
ttttgtgatg ctcgtcaggg gggcggagcc tatggaaaaa cgccagcaac gcggcctttt    4260
tacggttcct ggccttttgc tggccttttg ctcacatgtt ctttcctgcg ttatcccctg    4320
attctgtgga taaccgtatt accgcctttg agtgagctga taccgctcgc cgcagccgaa    4380
```

| | |
|---|---:|
| cgaccgagcg cagcgagtca gtgagcgagg aagcggaaga gcgcctgatg cggtattttc | 4440 |
| tccttacgca tctgtgcggt atttcacacc gcatatggtg cactctcagt acaatctgct | 4500 |
| ctgatgccgc atagttaagc cagtatacac tccgctatcg ctacgtgact gggtcatggc | 4560 |
| tgcgccccga cacccgccaa cacccgctga cgcgccctga cgggcttgtc tgctcccggc | 4620 |
| atccgcttac agacaagctg tgaccgtctc cgggagctgc atgtgtcaga ggttttcacc | 4680 |
| gtcatcaccg aaacgcgcga ggcagcagat caattcgcgc gcgaaggcga agcggcatgc | 4740 |
| atttacgttg acaccatcga atggtgcaaa acctttcgcg gtatggcatg atagcgcccg | 4800 |
| gaagagagtc aattcagggt ggtgaatgtg aaaccagtaa cgttatacga tgtcgcagag | 4860 |
| tatgccggtg tctcttatca gaccgtttcc cgcgtggtga accaggccag ccacgtttct | 4920 |
| gcgaaaacgc gggaaaaagt ggaagcggcg atggcggagc tgaattacat tcccaaccgc | 4980 |
| gtggcacaac aactggcggg caaacagtcg ttgctgattg gcgttgccac ctccagtctg | 5040 |
| gccctgcacg cgccgtcgca aattgtcgcg gcgattaaat ctcgcgccga tcaactgggt | 5100 |
| gccagcgtgg tggtgtcgat ggtagaacga agcggcgtcg aagcctgtaa agcggcggtg | 5160 |
| cacaatcttc tcgcgcaacg cgtcagtggg ctgatcatta actatccgct ggatgaccag | 5220 |
| gatgccattg ctgtggaagc tgcctgcact aatgttccgg cgttatttct tgatgtctct | 5280 |
| gaccagacac ccatcaacag tattatttc tcccatgaag acggtacgcg actgggcgtg | 5340 |
| gagcatctgg tcgcattggg tcaccagcaa atcgcgctgt tagcgggccc attaagttct | 5400 |
| gtctcggcgc gtctgcgtct ggctggctgg cataaatatc tcactcgcaa tcaaattcag | 5460 |
| ccgatagcgc aacgggaagg cgactggagt gccatgtccg ttttcaaca aaccatgcaa | 5520 |
| atgctgaatg agggcatcgt tcccactgcg atgctggttg ccaacgatca gatggcgctg | 5580 |
| ggcgcaatgc gcgccattac cgagtccggg ctgcgcgttg gtgcggatat ctcggtagtg | 5640 |
| ggatacgacg ataccgaaga cagctcatgt tatatcccgc cgtcaaccac catcaaacag | 5700 |
| gattttcgcc tgctggggca aaccagcgtg gaccgcttgc tgcaactctc tcagggccag | 5760 |
| gcggtgaagg gcaatcagct gttgcccgtc tcactggtga aaagaaaaac caccctggcg | 5820 |
| cccaatacgc aaaccgcctc tccccgcgcg ttggccgatt cattaatgca gctggcacga | 5880 |
| caggtttccc gactggaaag cgggcagtga gcgcaacgca attaatgtga gttagcgcga | 5940 |
| attgatctg | 5949 |

<210> SEQ ID NO 11
<211> LENGTH: 5928
<212> TYPE: DNA
<213> ORGANISM: artificial
<220> FEATURE:
<223> OTHER INFORMATION: Designed expression vector DNA having genetic
      circuit C

<400> SEQUENCE: 11

| | |
|---|---:|
| gtttgacagc ttatcatcga ctgcacggtg caccaatgct tctggcgtca ggcagccatc | 60 |
| ggaagctgtg gtatggctgt gcaggtcgta atcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgagcgg | 420 |

```
atacatattt gaatgtattt agaaaaataa acaaataggg gttccgcgca catttccccg    480
aaaagtgcca cctgacgtct aagaaaccat tattatcatg aaaaacataa atgccgacga    540
cacatacaga ataattaata aaattaaggc ttgtagaagc aataatgata ttaatcaatg    600
cttatctgat atgactaaaa tggtacattg tgaatattat ttactcgcga tcatttatcc    660
tcattctatg gttaaatctg atatttcaat cctagataat taccctaaaa aatggaggca    720
atattatgat gacgctaatt taataaaata tgatcctata gtagattatt ctaactccaa    780
tcattcacca attaattgga atatatttga aaacaatgct gtaaataaaa aatctccaaa    840
tgtaattaaa gaagcgaaaa catcaggtct tatcactggg tttagttttcc ctattcatac    900 ggctaacaat ggcttcggaa tgcttagttt tgcacattca gaaaaagaca actatataga    960
tagtttattt ttacatgcgt gtatgaacat accattaatt gttccttctc tagttgataa   1020
ttatcgaaaa ataaatatag caaataataa atcaaacaac gatttaacca aaagagaaaa   1080
agaatgttta gcgtgggcat gcgaaggaaa aagctcttgg gatatttcaa aaatattagg   1140
ttgcagtgag cgtactgtca ctttccattt aaccaatgcg caaatgaaac tcaatacaac   1200
aaaccgctgc caaagtattt ctaaagcaat tttaacagga gcaattgatt gcccatactt   1260
taaaaattaa taacactgat agtgctagtg tagatcacta ctagagccag gcatcaaata   1320
aaacgaaagg ctcagtcgaa agactgggcc tttcgtttta tctgttgttt gtcggtgaac   1380
gctctctact agagtcacac tggctcacct tcgggtgggc ctttctgcgt ttatatacta   1440
gagacctgta ggatcgtaca ggtttacgca agaaaatggt ttgttatagt cgaataaatc   1500 catgatgag cacaaaaaag aaaccattaa cacaagagca gcttgaggac gcacgtcgcc   1560
ttaaagcaat ttatgaaaaa agaaaaatg aacttggctt atcccaggaa tctgtcgcag   1620
acaagatggg gatggggcag tcaggcgttg gtgctttatt taatggcatc aatgcattaa   1680
atgcttataa cgccgcattg cttgcaaaaa ttctcaaagt tagcgttgaa gaatttagcc   1740
cttcaatcgc cagagaaatc tacgagatgt atgaagcggt tagtatgcag ccgtcactta   1800
gaagtgagta tgagtaccct gttttttctc atgttcaggc agggatgttc tcacctgagc   1860
ttagaacctt taccaaaggt gatgcggaga gatgggtaag cacaaccaaa aaagccagtg   1920
attctgcatt ctggcttgag gttgaaggta attccatgac cgcaccaaca ggctccaagc   1980
caagcttacg tagaacaaaa actcatctca gaagaggatc tgaatagcgc cgtcgaccat   2040
catcatcatc atcattgagt ttaaacggtc tccagcttgg ctgttttggc ggatgagaga   2100
agattttcag cctgatacag attaaatcag aacgcagaag cggtctgata aaacagaatt   2160
tgcctggcgg cagtagcgcg gtggtcccac ctgaccccat gccgaactca gaagtgaaac   2220
gccgtagcgc cgatggtagt gtggggtctc cccatgcgag agtagggaac tgccaggcat   2280
caaataaaac gaaaggctca gtcgaaagac tgggcctttc gttttatctg ttgtttgtcg   2340
gtgaacgctc tcctgagtag acaaatccgc cgggagcgg atttgaacgt tgcgaagcaa   2400
cggcccggag ggtggcgggc aggacgcccg ccataaactg ccaggcatca aattaagcag   2460
aaggccatcc tgacggatgg cctttttgcg tttctacaaa ctcttttttgt ttatttttct   2520 aaatacattc aaatatgtat ccgctcatga gacaataacc ctgataaatg cttcaataat   2580
attgaaaaag gaagagtatg agtattcaac atttccgtgt cgcccttatt ccctttttttg   2640 cggcattttg ccttcctgtt tttgctcacc cagaaacgct ggtgaaagta aaagatgctg   2700
aagatcagtt gggtgcacga gtgggttaca tcgaactgga tctcaacagc ggtaagatcc   2760
ttgagagttt tcgccccgaa gaacgttttc caatgatgag cacttttaaa gttctgctat   2820
```

```
gtggcgcggt attatcccgt gttgacgccg ggcaagagca actcggtcgc cgcatacact  2880
attctcagaa tgacttggtt gagtactcac cagtcacaga aaagcatctt acggatggca  2940
tgacagtaag agaattatgc agtgctgcca taaccatgag tgataacact gcggccaact  3000
tacttctgac aacgatcgga ggaccgaagg agctaaccgc ttttttgcac aacatggggg  3060
atcatgtaac tcgccttgat cgttgggaac cggagctgaa tgaagccata ccaaacgacg  3120
agcgtgacac cacgatgcct acagcaatgg caacaacgtt gcgcaaacta ttaactggcg  3180
aactacttac tctagcttcc cggcaacaat taatagactg gatggaggcg gataaagttg  3240
caggaccact tctgcgctcg gcccttccgg ctggctggtt tattgctgat aaatctggag  3300
ccggtgagcg tgggtctcgc ggtatcattg cagcactggg gccagatggt aagccctccc  3360
gtatcgtagt tatctacacg acggggagtc aggcaactat ggatgaacga atagacagat  3420
cgctgagat aggtgcctca ctgattaagc attggtaact gtcagaccaa gtttactcat  3480
atatacttta gattgattta aaacttcatt tttaatttaa aaggatctag gtgaagatcc  3540
tttttgataa tctcatgacc aaaatccctt aacgtgagtt ttcgttccac tgagcgtcag  3600
accccgtaga aaagatcaaa ggatcttctt gagatccttt ttttctgcgc gtaatctgct  3660
gcttgcaaac aaaaaaacca ccgctaccag cggtggtttg tttgccggat caagagctac  3720
caactctttt tccgaaggta actggcttca gcagagcgca gataccaaat actgtccttc  3780
tagtgtagcc gtagttaggc caccacttca agaactctgt agcaccgcct acatacctcg  3840
ctctgctaat cctgttacca gtggctgctg ccagtggcga taagtcgtgt cttaccgggt  3900
tggactcaag acgatagtta ccggataagg cgcagcggtc gggctgaacg gggggttcgt  3960
gcacacagcc cagcttggag cgaacgacct acaccgaact gagataccta cagcgtgagc  4020
tatgagaaag cgccacgctt cccgaaggga gaaaggcgga caggtatccg gtaagcggca  4080
gggtcggaac aggagagcgc acgagggagc ttccaggggg aaacgcctgg tatctttata  4140
gtcctgtcgg gtttcgccac ctctgacttg agcgtcgatt tttgtgatgc tcgtcagggg  4200
ggcggagcct atggaaaaac gccagcaacg cggccttttt acggttcctg gccttttgct  4260
ggccttttgc tcacatgttc tttcctgcgt tatcccctga ttctgtggat aaccgtatta  4320
ccgcctttga gtgagctgat accgctcgcc gcagccgaac gaccgagcgc agcgagtcag  4380
tgagcgagga agcggaagag cgcctgatgc ggtattttct ccttacgcat ctgtgcggta  4440
tttcacaccg catatggtgc actctcagta caatctgctc tgatgccgca tagttaagcc  4500
agtatacact ccgctatcgc tacgtgactg ggtcatggct gcgccccgac acccgccaac  4560
acccgctgac gcgccctgac gggcttgtct gctcccggca tccgcttaca gacaagctgt  4620
gaccgtctcc gggagctgca tgtgtcagag gttttcaccg tcatcaccga aacgcgcgag  4680
gcagcagatc aattcgcgcg cgaaggcgaa gcggcatgca tttacgttga caccatcgaa  4740
tggtgcaaaa cctttcgcgg tatggcatga tagcgcccgg aagagagtca attcagggtg  4800
gtgaatgtga accagtaac gttatacgat gtcgcagagt atgccggtgt ctcttatcag  4860
accgtttccc gcgtggtgaa ccaggccagc cacgtttctg cgaaaacgcg ggaaaaagtg  4920
gaagcggcga tggcggagct gaattacatt cccaaccgcg tggcacaaca actggcgggc  4980
aaacagtcgt tgctgattgg cgttgccacc tccagtctgg ccctgcacgc gccgtcgcaa  5040
attgtcgcgg cgattaaatc tcgcgccgat caactgggtg ccagcgtggt ggtgtcgatg  5100
gtagaacgaa gcggcgtcga agcctgtaaa gcggcggtgc acaatcttct cgcgcaacgc  5160
```

```
gtcagtgggc tgatcattaa ctatccgctg gatgaccagg atgccattgc tgtggaagct    5220
gcctgcacta atgttccggc gttatttctt gatgtctctg accagacacc catcaacagt    5280
attattttct cccatgaaga cggtacgcga ctgggcgtgg agcatctggt cgcattgggt    5340
caccagcaaa tcgcgctgtt agcgggccca ttaagttctg tctcggcgcg tctgcgtctg    5400
gctggctggc ataaatatct cactcgcaat caaattcagc cgatagcgga acgggaaggc    5460
gactggagtg ccatgtccgg ttttcaacaa accatgcaaa tgctgaatga gggcatcgtt    5520
cccactgcga tgctggttgc caacgatcag atggcgctgg cgcaatgcg cgccattacc     5580 gagtccgggc tgcgcgttgg tgcggatatc tcggtagtgg atacgacga taccgaagac     5640 agctcatgtt atatcccgcc gtcaaccacc atcaaacagg attttcgcct gctggggcaa    5700
accagcgtgg accgcttgct gcaactctct cagggccagg cggtgaaggg caatcagctg    5760
ttgcccgtct cactggtgaa agaaaaaacc accctggcgc ccaatacgca aaccgcctct    5820
ccccgcgcgt tggccgattc attaatgcag ctggcacgac aggtttcccg actggaaagc    5880
gggcagtgag cgcaacgcaa ttaatgtgag ttagcgcgaa ttgatctg                 5928

<210> SEQ ID NO 12
<211> LENGTH: 5732
<212> TYPE: DNA
<213> ORGANISM: artificial
<220> FEATURE:
<223> OTHER INFORMATION: Designed expression vector DNA having genetic
      circuit D

<400> SEQUENCE: 12
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgagcgg    420
atacatattt gaatgtattt agaaaaataa acaataggg gttccgcgca catttccccg     480
aaaagtgcca cctgacgtct aagaaaccat tattatcatg aaaacataa atgccgacga    540 cacatacaga ataattaata aaattaaggc ttgtagaagc aataatgata ttaatcaatg    600
cttatctgat atgactaaaa tggtacattg tgaatattat ttactcgcga tcatttatcc    660
tcattctatg gttaaatctg atatttcaat cctagataat taccctaaaa aatggaggca    720
atattatgat gacgctaatt taataaaata tgatccctata gtagattatt ctaactccaa    780
tcattcacca attaattgga atatatttga aaacaatgct gtaaataaaa aatctccaaa    840
tgtaattaaa gaagcgaaaa catcaggtct tatcactggg tttagtttcc ctattcatac    900
ggctaacaat ggcttcggaa tgcttagttt tgcacattca gaaaaagaca actatataga    960 tagtttatttt ttacatgcgt gtatgaacat accattaatt gttccttctc tagttgataa    1020
ttatcgaaaa ataaatatag caaataataa atcaaacaac gatttaacca aaagagaaaa    1080
agaatgttta gcgtgggcat gcgaaggaaa aagctcttgg gatatttcaa aaatattagg    1140
```

| | |
|---|---|
| ttgcagtgag cgtactgtca ctttccattt aaccaatgcg caaatgaaac tcaatacaac | 1200 |
| aaaccgctgc caaagtattt ctaaagcaat tttaacagga gcaattgatt gcccatactt | 1260 |
| taaaaattaa taacactgat agtgaattca agaggagaaa atactagcca tgagcacaaa | 1320 |
| aaagaaacca ttaacacaag agcagcttga ggacgcacgt cgccttaaag caatttatga | 1380 |
| aaaaaagaaa aatgaacttg gcttatccca ggaatctgtc gcagacaaga tggggatggg | 1440 |
| gcagtcaggc gttggtgctt tatttaatgg catcaatgca ttaaatgctt ataacgccgc | 1500 |
| attgcttgca aaaattctca agttagcgt tgaagaattt agcccttcaa tcgccagaga | 1560 |
| aatctacgag atgtatgaag cggttagtat gcagccgtca cttagaagtg agtatgagta | 1620 |
| ccctgttttt tctcatgttc aggcagggat gttctcacct gagcttagaa cctttaccaa | 1680 |
| aggtgatgcg gagagatggg taagcacaac caaaaaagcc agtgattctg cattctggct | 1740 |
| tgaggttgaa ggtaattcca tgaccgcacc aacaggctcc aagccaagct acgtagaaac | 1800 |
| aaaaactcat ctcagaagag gatctgaata gcgccgtcga ccatcatcat catcatcatt | 1860 |
| gagtttaaac ggtctccagc ttggctgttt tggcggatga gaagatttt tcagcctgat | 1920 |
| acagattaaa tcagaacgca gaagcggtct gataaaacag aatttgcctg gcggcagtag | 1980 |
| cgcggtggtc ccacctgacc ccatgccgaa ctcagaagtg aaacgccgta gcgccgatgg | 2040 |
| tagtgtgggg tctccccatg cgagagtagg gaactgccag gcatcaaata aaacgaaagg | 2100 |
| ctcagtcgaa agactgggcc tttcgtttta tctgttgttt gtcggtgaac gctctcctga | 2160 |
| gtaggacaaa tccgccggga gcggatttga acgttgcgaa gcaacggccc ggagggtggc | 2220 |
| gggcaggacg cccgccataa actgccaggc atcaaattaa gcagaaggcc atcctgacgg | 2280 |
| atggccttt tgcgtttcta caaactcttt ttgtttattt ttctaaatac attcaaatat | 2340 |
| gtatccgctc atgagacaat aaccctgata aatgcttcaa taatattgaa aaaggaagag | 2400 |
| tatgagtatt caacatttcc gtgtcgccct tattccctt tttgcggcat tttgccttcc | 2460 |
| tgttttgct cacccagaaa cgctggtgaa agtaaaagat gctgaagatc agttgggtgc | 2520 |
| acgagtgggg tacatcgaac tggatctcaa cagcggtaag atccttgaga gttttcgccc | 2580 |
| cgaagaacgt tttccaatga tgagcacttt taaagttctg ctatgtggcg cggtattatc | 2640 |
| ccgtgttgac gccgggcaag agcaactcgg tcgccgcata cactattctc agaatgactt | 2700 |
| ggttgagtac tcaccagtca cagaaaagca tcttacggat ggcatgacag taagagaatt | 2760 |
| atgcagtgct gccataacca tgagtgataa cactgcggcc aacttacttc tgacaacgat | 2820 |
| cggaggaccg aaggagctaa ccgcttttt gcacaacatg ggggatcatg taactcgcct | 2880 |
| tgatcgttgg gaaccggagc tgaatgaagc cataccaaac gacgagcgtg acaccacgat | 2940 |
| gcctacagca atggcaacaa cgttgcgcaa actattaact ggcgaactac ttactctagc | 3000 |
| ttcccggcaa caattaatag actggatgga ggcggataaa gttgcaggac cacttctgcg | 3060 |
| ctcggccctt ccggctggct ggtttattgc tgataaatct ggagccggtg agcgtgggtc | 3120 |
| tcgcggtatc attgcagcac tggggccaga tggtaagccc tcccgtatcg tagttatcta | 3180 |
| cacgacgggg agtcaggcaa ctatggatga acgaaataga cagatcgctg agataggtgc | 3240 |
| ctcactgatt aagcattggt aactgtcaga ccaagtttac tcatatatac tttagattga | 3300 |
| tttaaaactt catttttaat ttaaaaggat ctaggtgaag atccttttg ataatctcat | 3360 |
| gaccaaaatc ccttaacgtg agttttcgtt ccactgagcg tcagacccg tagaaaagat | 3420 |

-continued

```
caaaggatct tcttgagatc cttttttttct gcgcgtaatc tgctgcttgc aaacaaaaaa    3480
accaccgcta ccagcggtgg tttgtttgcc ggatcaagag ctaccaactc ttttttccgaa    3540 ggtaactggc ttcagcagag cgcagatacc aaatactgtc cttctagtgt agccgtagtt    3600
aggccaccac ttcaagaact ctgtagcacc gcctacatac ctcgctctgc taatcctgtt    3660
accagtggct gctgccagtg gcgataagtc gtgtcttacc gggttggact caagacgata    3720
gttaccggat aaggcgcagc ggtcgggctg aacgggggt tcgtgcacac agcccagctt     3780
ggagcgaacg acctacaccg aactgagata cctacagcgt gagctatgag aaagcgccac    3840
gcttcccgaa gggagaaagg cggacaggta tccggtaagc ggcagggtcg aacaggaga     3900 gcgcacgagg gagcttccag ggggaaacgc ctggtatctt tatagtcctg tcgggtttcg    3960
ccacctctga cttgagcgtc gatttttgtg atgctcgtca gggggcgga gcctatggaa     4020 aaacgccagc aacgcggcct ttttacggtt cctggccttt tgctggcctt ttgctcacat    4080
gttctttcct gcgttatccc ctgattctgt ggataaccgt attaccgcct ttgagtgagc    4140
tgataccgct cgccgcagcc gaacgaccga gcgcagcgag tcagtgagcg aggaagcgga    4200
agagcgcctg atgcggtatt ttctccttac gcatctgtgc ggtatttcac accgcatatg    4260
gtgcactctc agtacaatct gctctgatgc cgcatagtta agccagtata cactccgcta    4320
tcgctacgtg actgggtcat ggctgcgccc cgacacccgc caacacccgc tgacgcgccc    4380
tgacgggctt gtctgctccc ggcatccgct tacagacaag ctgtgaccgt ctccgggagc    4440
tgcatgtgtc agaggttttc accgtcatca ccgaaacgcg cgaggcagca gatcaattcg    4500
cgcgcgaagg cgaagcggca tgcatttacg ttgacaccat cgaatggtgc aaaacctttc    4560
gcggtatggc atgatagcgc ccggaagaga gtcaattcag ggtggtgaat gtgaaaccag    4620
taacgttata cgatgtcgca gagtatgccg gtgtctctta tcagaccgtt tcccgcgtgg    4680
tgaaccaggc cagccacgtt tctgcgaaaa cgcgggaaaa agtggaagcg gcgatggcgg    4740
agctgaatta cattcccaac cgcgtggcac aacaactggc gggcaaacag tcgttgctga    4800
ttggcgttgc cacctccagt ctggccctgc acgcgccgtc gcaaattgtc gcggcgatta    4860
aatctcgcgc cgatcaactg ggtgccagcg tggtggtgtc gatggtagaa cgaagcggcg    4920
tcgaagcctg taaagcggcg gtgcacaatc ttctcgcgca acgcgtcagt gggctgatca    4980
ttaactatcc gctggatgac caggatgcca ttgctgtgga agctgcctgc actaatgttc    5040
cggcgttatt tcttgatgtc tctgaccaga cacccatcaa cagtattatt ttctcccatg    5100
aagacggtac gcgactgggc gtggagcatc tggtcgcatt gggtcaccag caaatcgcgc    5160
tgttagcggg cccattaagt tctgtctcgg cgcgtctgcg tctggctggc tggcataaat    5220
atctcactcg caatcaaatt cagccgatag cggaacggga aggcgactgg agtgccatgt    5280
ccggttttca acaaaccatg caaatgctga atgagggcat cgttcccact gcgatgctgg    5340
ttgccaacga tcagatggcg ctgggcgcaa tgcgcgccat taccgagtcc gggctgcgcg    5400
ttggtgcgga tatctcggta gtgggatacg acgataccga agacagctca tgttatatcc    5460
cgccgtcaac caccatcaaa caggattttc gcctgctggg gcaaaccagc gtggaccgct    5520
tgctgcaact ctctcagggc caggcggtga agggcaatca gctgttgccc gtctcactgg    5580
tgaaaagaaa aaccaccctg gcgcccaata cgcaaaccgc ctctccccgc gcgttggccg    5640
attcattaat gcagctggca cgacaggttt cccgactgga aagcgggcag tgagcgcaac    5700
gcaattaatg tgagttagcg cgaattgatc tg                                 5732
```

US 9,315,816 B2

METHOD FOR RAPIDLY DEVELOPING GENE SWITCHES AND GENE CIRCUITS

This application is a National Stage Application of PCT/JP2011/075290, filed Nov. 2, 2011, which claims priority from Japanese Patent Application No. 2010-246271, filed Nov. 2, 2010.

TECHNICAL FIELD

The present invention relates to a developing method for a genetic switch and a genetic circuit. In more particular, the present invention relates to a developing method for a genetic switch and a genetic circuit, including selecting a genetic switch and a genetic circuit by using, as an indicator, cell death or cell death avoidance caused by expression or non-expression of a gene whose expression is controlled by an action of each of the genetic switch and the genetic circuit having the genetic switch. Specifically, the present invention relates to a selection method for a genetic switch and a genetic circuit, including using, as a selector, an expression vector containing at least: a gene sequence whose expression is controlled by a transcription regulatory factor to be expressed when a genetic switch and a genetic circuit including the genetic switch operate; and a promoter sequence operably linked to the gene sequence upstream thereof. The present invention also relates to an expression vector to be used in the selection method.

BACKGROUND ART

A control system for gene expression is extremely important as basic means for each of protein production, metabolic engineering, and synthetic biology. Biotechnology that uses the control system for gene expression is employed in various fields such as mass production of a useful protein, metabolic engineering, and a whole cell biosensor. There is a demand for a technology for producing a control system for gene expression with desired properties, which may be naturally derived or may be artificially created, as required and rapidly.

In the natural world, there are various transcription and/or translation control mechanisms and sensor mechanisms. In recent years, a genetic switch has been reported as a control system for gene expression (Non Patent Literatures 1 to 5). The genetic switch is a molecular device for switching expression and non-expression (ON/OFF) of a specific gene with the use of any of various pieces of information as input. Through construction of a genetic circuit by integrating various genetic switches, it is becoming possible to construct an oscillator, a counter, a logic circuit, and the like in cells. In the genetic circuit to be constructed in cells, a plurality of genetic switch mechanisms have to work in cooperation to finally establish an integrated function. To that end, all the switches forming the circuit are required to work with certain respective properties. In order that an arbitrary genetic circuit can be freely designed, a tremendous number of genetic switches with different functions/properties are required.

For example, the genetic switch can be applied to mass production of a useful protein. The production of a useful protein frequently employs an approach involving forcing host cells such as *Escherichia coli* (hereinafter sometimes abbreviated as "*E. coli*") to express a target protein obtained from an organism of a different species. However, there are many proteins showing toxicity to the host cells. In case of producing any such protein, the host cells are made to proliferate to a sufficient number, and then the forced expression is caused by "inducing" expression at appropriate timing. In this case, the following two conditions are required: (1) a basal expression level in an uninduced state is sufficiently low (i.e., stringency, less "leakiness"); and (2) sufficient gene expression is achieved when the expression is induced (ON) (i.e., a ratio between expression levels in ON/OFF states is large). In order to achieve the conditions, there have been developed various promoter systems such as the pET system (manufactured by Novagen). However, the search for an optimum genetic switch is still in progress.

The genetic switch can also be used as means for metabolic engineering. In metabolic engineering, a biosynthetic pathway of a given substance of interest is constructed by simultaneously expressing a plurality of enzyme genes in one host cell. In pursuing the best results in the constructed artificial biosynthetic pathway, such as a maximized yield of a final product per biomass and a minimized amount of a by-product, it is vital to regulate and investigate expression levels of individual genes meticulously, and if possible, independently. For this purpose, a large number of genetic switches with desired ON/OFF switching properties are required. Particularly in the case of simultaneously regulating expression of a plurality of genes in one cell, functions required of genetic switches include, for example the following: (1) genetic switches are mutually orthogonal, i.e., an inducer for one genetic switch does not cause improper operation of another genetic switch; and (2) an level of expression by each genetic switch can be continuously regulated.

The genetic switch can also be used as a biosensor. Cells detect large amounts of chemical information and/or physical information, and express an appropriate group of genes in response thereto. There has been developed a cell sensor (whole cell sensor) having a reporter gene such as a green fluorescent protein (GFP) ligated downstream of the "substance detection" system. A demand exists for development of a sensor for an arbitrary substance (or physical stimulation) through, for example, proper modification of the already developed sensor.

When the genetic switches and sensor systems as described above can be created in large numbers, complex genetic circuits provided with information integration and/or processing (assessment) functions can be created by combining the genetic switches and the sensor systems. However, the genetic switches included in the genetic circuit have problems of leakiness and cross-talk of switches, which correspond to leakage of electricity in an electronic circuit. Hence, when a plurality of genetic switches are simultaneously used, the genetic switches do not properly work. Regarding switching properties of genetic switches, such as an ON/OFF threshold and a dynamic range, when complex genetic circuits are designed by combining the genetic switches, it is strongly required to: (1) arbitrarily change a response threshold to cause an expression trigger; (2) repress "leakiness" of expression under an uninduced state; and (3) secure orthogonality to other factors in cells. The de novo design of those requirements into a complex genetic circuit is an extremely difficult task. Therefore, the limit of integration of a circuit in cell engineering is extremely low at present. In order to overcome those problems, improvement of the genetic switch has been demanded.

On the other hand, even a complex circuit, when seen as a whole, can be regarded as one genetic switch that stipulates a triggered state of a gene depending on input conditions. That is, the genetic circuit triggers expression of a downstream gene (set) under certain conditions, and represses the expression under other conditions.

Therefore, in construction of genetic circuits, through selection of those in a triggered state when gene expression should be ON and/or those in a repressed state in a situation where gene expression should be OFF (ON selection/OFF selection), it is possible to select and/or obtain genetic circuits having arbitrary output properties. When the ON selection/OFF selection can be easily and successively conducted, various genetic switches (or genetic circuits) can be rapidly developed. In functional selection of genetic switches, it is necessary to select genetic switches in both the ON state and the OFF state under various input conditions (Non Patent Literatures 6 to 12). That is, ligation of two selectors, i.e., an ON-selector and an OFF-selector to an output side, i.e., downstream of a genetic circuit enables the functional selection of a genetic switch or an integrated circuit thereof, i.e., a genetic circuit. In molecular genetics, various ON-selectors and OFF-selectors are known.

Recently, an attempt has been made to cause one gene to conduct the functions of the ON-selector and the OFF-selector (Non Patent Literatures 10 to 13). A selector having both the functions of the ON-selector and the OFF-selector is called a dual selector. An "operon-type" selection method involving using an independent ON-selector and OFF-selector has a problem in that genetic mutations frequently occur in one of the selector genes, resulting in the frequent emergence of false positives. However, the dual selector does not have such problem. Although there are few reports of dual selectors for the functional selection of genetic switches, there have been reported systems each using a gene that imparts antibiotic resistance to cells, such as a system using a tetracycline resistance gene tetA (Non Patent Literatures 10 and 11) and a system using a chloramphenicol resistance gene CAT (Non Patent Literature 12), and a system using a chemotaxis gene cheZ of E. coli (Non Patent Literature 13). The system using tetA conducts dual selection by utilizing a bactericidal mechanism of cells through control of the transcription of tetA and measuring the survival or death of cells. The system using cheZ conducts dual selection based on the presence or absence of mobility of cells through control of the translation of cheZ.

Hitherto, various selection systems for use in ON selection/OFF selection have been developed. However, each of the systems achieves selection by the so-called selective proliferation, in which cells can proliferate when a genetic circuit transfected into the cells is properly output. Such selection system includes a cell proliferation process in each selection operation, and hence requires about 12 hours to 24 hours for each selection operation. Therefore, selection of a genetic circuit, in particular, selection of a complex genetic circuit, requires a large number of days. As described above, the conventional approaches have the problem of requiring a long time period for a selection operation, or such problem that selection efficiency is affected by the selection conditions.

CITATION LIST

Non Patent Literature

[NPL 1] Galvao, T C and de Lorenzo, V, Transcriptional regulators à la carte: engineering new effector specificities in bacterial regulatory proteins. Curr Opin Biotechnol, 17, 34-42 (2006)

[NPL 2] Lutz, R and Bujard, H, Independent and tight regulation of transcriptional units in *Escherichia coli* via the LacR/O, the TetR/O and AraC/I1-I2 regulatory elements. Nucleic Acids Res, 25, 1203-10 (1997)

[NPL 3] Cox, R S 3rd, et al., Programming gene expression with combinatorial promoters. Mol Syst Biol, 3, 145 (2007)

[NPL 4] Eddy, S R, Noncoding RNA genes., Curr Opin Genet Dev., 9, 695-9 (1999)

[NPL 5] Garst, A D, Batey R T., A switch in time: Detailing the life of a riboswitch., Biochim Biophys Acta. 1789, 584-91 (2009)

[NPL 6] Yokobayashi, Y, et al., Directed evolution of a genetic circuit. Proc Natl Acad Sci USA, 99, 16587-91 (2002)

[NPL 7] Yokobayashi, Y, et al., A dual selection module for directed evolution of genetic circuits. Nat. Computing, 4, 245-54 (2005)

[NPL 8] Tang, S Y, et al., AraC regulatory protein mutants with altered effector specificity. J Am Chem Soc, 130, 5267-71 (2008)

[NPL 9] Lynch, S A and Gallivan, J P, A flow cytometry-based screen for synthetic riboswitches. Nucleic Acids Res, 37, 184-92 (2009)

[NPL 10] Nomura, Y and Yokobayashi, Y, Dual selection of a genetic switch by a single selection marker. Biosystems, 90, 115-20 (2007)

[NPL 11] Muranaka, N, et al., An efficient platform for genetic selection and screening of gene switches in *Escherichia coli*. Nucleic Acids Res, 37, e39 (2009)

[NPL 12] Rackham, O and Chin, J W, A network of orthogonal ribosome mRNA pairs. Nat. Chem. Biol., 1, 159-66 (2005)

[NPL 13] Topp, S and Gallivan, J P, Random walks to synthetic riboswitches—a high-throughput selection based on cell motility. Chembiochem, 9, 210-3 (2008)

SUMMARY OF INVENTION

Technical Problem

The functions of genetic switches or biosensors are higher order molecular functions exerted by a plurality of elements co-operating in a complex manner, and hence it is extremely difficult to rationally design genetic switches with desired functions/properties. In addition, the rational design of a genetic circuit, which is constructed by combining the genetic switches, involves greater difficulty. Therefore, it is necessary to prepare a library by producing a large number of genetic switch variants, and select and obtain a variant with a desired function from the library.

By focusing attention on a human herpes virus derived thymidine kinase (hsvTK) and causing hsvTK to operate on the output side, i.e., downstream of a genetic circuit to conduct ON selection and/or OFF selection, the inventors of the present invention have already completed a method of obtaining a genetic switch and genetic circuit with desired properties and/or functions rapidly, simply, and reliably, and have filed a patent application (Japanese Patent Application No. 2009-262909). This approach has shown extremely high selection efficiency for the selection of genetic switches and genetic circuits in both ON selection and OFF selection. In particular, the OFF selection by this approach is highly useful because the selection can be conducted within a short time period of about 30 minutes. However, the ON selection by this approach still requires a time period of about 24 hours, and hence has a room for improvement.

An object of the present invention is to provide an effective method by which the selection of a genetic switch and a genetic circuit can be conducted within a short time period and with high selection efficiency.

Solution to Problem

The inventors of the present invention have made extensive studies in order to achieve the object, and have found that ON selection can be conducted within a short time period by: using, as a selector, an expression vector designed so that alkyladenine DNA glycosidase (AAG) as an alkylated DNA repair enzyme can be operated on the output side, i.e., downstream of a genetic circuit; operating the genetic switch in cells transfected with the expression vector and an expression vector expressing the genetic circuit under such conditions that cell death due to DNA alkylation is induced, and collecting viable cells. In addition, by employing the ON selection method in combination with the OFF selection method previously developed by the inventors of the present invention, i.e., the OFF selection method involving using, as a selector, an expression vector designed so that hsvTK can be operated on the output side of a genetic circuit, the inventors of the present invention have found a selection method for a genetic switch and a genetic circuit by which ON selection and OFF selection can both be conducted within short time periods of about 5 to 30 minutes. The present invention has been completed based on those research outcomes.

That is, the present invention relates to the following:

1. A selection method for a genetic switch and a genetic circuit, the selection method including: using cells transfected with an expression vector harboring a genetic circuit having a genetic switch expression sequence, and a gene sequence encoding a transcription regulatory factor whose expression is induced by a genetic switch encoded by the genetic switch expression sequence, and an expression vector having a gene sequence whose expression is controlled by the transcription regulatory factor; and in the presence or absence of a compound that activates the genetic switch, incubating the cells with the addition of a compound that can induce cell death under expression of the gene sequence whose expression is controlled, and collecting viable cells, and/or in the presence or absence of a compound that activates the genetic switch, incubating the cells with the addition of a compound that can induce cell death under non-expression of the gene sequence whose expression is controlled, and collecting viable cells;

2. A selection method for a genetic switch and a genetic circuit according to the above-mentioned item 1., in which the expression vector having a gene sequence whose expression is controlled by the transcription regulatory factor is an expression vector having the following two gene sequences: a first gene sequence and a second gene sequence, expression of each of which is controlled by the transcription regulatory factor, the first gene sequence being a gene sequence encoding a protein different from that of the second gene sequence;

3. A selection method for a genetic switch and a genetic circuit according to the above-mentioned item 1., in which the expression vector having a gene sequence whose expression is controlled by the transcription regulatory factor is: an expression vector having a first gene sequence whose expression is controlled by the transcription regulatory factor; and an expression vector having a second gene sequence whose expression is controlled by the transcription regulatory factor, the first gene sequence being a gene sequence encoding a protein different from that of the second gene sequence;

4. A selection method for a genetic switch and a genetic circuit according to the above-mentioned item 1., the selection method including: using cells transfected with an expression vector harboring at least sequences according to the following items (a) and (b):
(a) a gene sequence encoding an alkylated DNA repair enzyme; and (b) a promoter sequence operably linked to the gene sequence according to the item (a) upstream of the gene sequence, and an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription regulatory factor that operates on the promoter sequence according to the item (b); and
(1) when the gene sequence encoding a transcription regulatory factor according to the item (f) is a transcription repression factor, in the absence of a compound that activates the genetic switch, incubating the cells with the addition of an alkylating agent, and collecting viable cells, or
(2) when the gene sequence encoding a transcription regulatory factor according to the item (f) is a transcription activation factor, in the presence of a compound that activates the genetic switch, incubating the cells with the addition of an alkylating agent, and collecting viable cells;

5. A selection method for a genetic switch and a genetic circuit according to the above-mentioned item 4., in which the alkylated DNA repair enzyme is alkyladenine DNA glycosidase (AAG);

6. A selection method for a genetic switch and a genetic circuit according to the above-mentioned item 4. or 5., in which the cells are an alkylating agent-hypersensitive *Escherichia coli* strain;

7. A selection method for a genetic switch and a genetic circuit according to any one of the above-mentioned items 4. to 6., in which the compound that causes alkylation of a gene is methanesulfonic acid (MMS);

8. A selection method for a genetic switch and a genetic circuit, the selection method including: using an alkylating agent-hypersensitive *Escherichia coli* strain transfected with an expression vector harboring at least sequences according to the following items (a) and (b):
(a) a gene sequence encoding alkyladenine DNA glycosidase (AAG); and
(b) a promoter sequence operably linked to the gene sequence according to the item (a) upstream of the gene sequence, and an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a CI protein that operates on the promoter sequence according to the item (b); and in the absence of a compound that activates the genetic switch, incubating the *Escherichia coli* strain with the addition of methanesulfonic acid (MMS) for 15 minutes to 60 minutes, and collecting viable cells;

9. A selection method for a genetic switch and a genetic circuit, the selection method including: using an alkylating agent-hypersensitive *Escherichia coli* strain transfected with an expression vector harboring at least sequences according to the following items (a) and (b):

(a) a gene sequence encoding alkyladenine DNA glycosidase (AAG) and a gene sequence encoding AP endonuclease (APE1); and
(b) a promoter sequence operably linked to the two gene sequences according to the item (a) upstream of the two gene sequences, and an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a CI protein that operates on the promoter sequence according to the item (b); and in the absence of a compound that activates the genetic switch, incubating the *Escherichia coli* strain with the addition of methanesulfonic acid (MMS) for 15 minutes to 60 minutes, and collecting viable cells;

10. A selection method for a genetic switch and a genetic circuit according to the above-mentioned item 1., the selection method including: using cells transfected with an expression vector harboring at least sequences according to the following items (a) and (b):
(a) a gene sequence encoding an alkylated DNA repair enzyme and a gene sequence encoding a thymidine kinase; and
(b) a promoter sequence operably linked to the two gene sequences according to the item (a) upstream of the two gene sequences, and an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription regulatory factor that operates on the promoter sequence according to the item (b); and
(1) when the gene sequence encoding a transcription regulatory factor according to the item (f) is a transcription repression factor, in the presence of a compound that activates the genetic switch, incubating the cells with the addition of a mutagenic nucleoside, and collecting viable cells, and in the absence of the compound, adding an alkylating agent to the recovered cells, followed by incubation, and collecting viable cells, or
(2) when the gene sequence encoding a transcription regulatory factor according to the item (f) is a transcription activation factor, in the presence of a compound that activates the genetic switch, incubating the cells with the addition of an alkylating agent, and collecting viable cells, and in the absence of the compound, adding a mutagenic nucleoside to the recovered cells, followed by incubation, and collecting viable cells;

11. A selection method for a genetic switch and a genetic circuit according to the above-mentioned item 1., the selection method including: using cells transfected with an expression vector harboring at least sequences according to the following items (a-1) and (b-1):
(a-1) a gene sequence encoding an alkylated DNA repair enzyme; and
(b-1) a promoter sequence operably linked to the gene sequence according to the item (a-1) upstream of the gene sequence, an expression vector harboring at least sequences according to the following items (a-2) and (b-2):
(a-2) a gene sequence encoding a thymidine kinase; and
(b-2) a promoter sequence operably linked to the gene sequence according to the item (a-2) upstream of the gene sequence, and an expression vector harboring at least sequences according to the following items (c) to (f):
(c) another promoter sequence different from the promoter sequences, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription regulatory factor that operates on the promoter sequence according to the item (b); and (1) when the gene sequence encoding a transcription regulatory factor according to the item (f) is a transcription repression factor, in the presence of a compound that activates the genetic switch, incubating the cells with the addition of a mutagenic nucleoside, and collecting viable cells, and in the absence of the compound, adding an alkylating agent to the recovered cells, followed by incubation, and collecting viable cells, or
(2) when the gene sequence encoding a transcription regulatory factor according to the item (f) is a transcription activation factor, in the presence of a compound that activates the genetic switch, incubating the cells with the addition of an alkylating agent, and collecting viable cells, and in the absence of the compound, adding a mutagenic nucleoside to the recovered cells, followed by incubation, and collecting viable cells;

12. A selection method for a genetic switch and a genetic circuit according to the above-mentioned item 10. or 11., in which the alkylated DNA repair enzyme is alkyladenine DNA glycosidase (AAG), and the thymidine kinase is a human herpes virus derived thymidine kinase;

13. A selection method for a genetic switch and a genetic circuit according to any one of the above-mentioned items 10. to 12., in which the cells are an alkylating agent-hypersensitive *Escherichia coli* strain;

14. A selection method for a genetic switch and a genetic circuit according to any one of the above-mentioned items 10 to 13, in which the compound that causes alkylation of a gene is methanesulfonic acid (MMS), and the mutagenic nucleoside is 6-($\beta$-D-2-deoxyribo-furanosyl)-3, 4-dihydro-8H-pyrimido[4,5-c][1,2]oxazin-7-one (dP);

15. A selection method for a genetic switch and a genetic circuit, the selection method including: using an alkylating agent-hypersensitive *Escherichia coli* strain transfected with an expression vector harboring at least sequences according to the following items (a) and (b):
(a) a gene sequence encoding alkyladenine DNA glycosidase (AAG) and a gene sequence encoding a human herpes virus derived thymidine kinase; and
(b) a promoter sequence operably linked to the two gene sequences according to the item (a) upstream of the two gene sequences, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a CI protein that operates on the promoter sequence according to the item (b); and in the presence of a compound that activates the genetic switch, incubating the *Escherichia coli* strain for 5 minutes to 60 minutes with the addition of 6-(β-D-2-deoxyribo-furanosyl)-3, 4-dihydro-8H-pyrimido[4,5-c][1,2]oxazin-7-one (dP), and collecting viable cells, and then, in the absence of the compound, incubating the cells for 15 minutes to 60 minutes with the addition of methanesulfonic acid (MMS), and collecting viable cells;

16. A selection method for a genetic switch and a genetic circuit, the selection method including: using an alkylating agent-hypersensitive *Escherichia coli* strain transfected with an expression vector harboring at least sequences according to the following items (a) and (b):

(a) a gene sequence encoding alkyladenine DNA glycosidase (AAG), a gene sequence encoding a human herpes virus derived thymidine kinase, and a gene sequence encoding AP endonuclease (APE1); and (b) a promoter sequence operably linked to the three gene sequences according to the item (a) upstream of the three gene sequences, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a CI protein that operates on the promoter sequence according to the item (b); and in the presence of a compound that activates the genetic switch, incubating the *Escherichia coli* strain for 5 minutes to 60 minutes with the addition of 6-(β-D-2-deoxyribo-furanosyl)-3, 4-dihydro-8H-pyrimido[4,5-c][1,2]oxazin-7-one (dP), and collecting viable cells, and then, in the absence of the compound, incubating the cells for 15 minutes to 60 minutes with the addition of methanesulfonic acid (MMS), and collecting viable cells;

17. A use of an expression vector including at least: a gene sequence encoding an alkylated DNA repair enzyme and a gene sequence encoding a thymidine kinase; and a promoter sequence operably linked to the two gene sequences upstream of the two gene sequences, in the selection method for a genetic switch and a genetic circuit according to the above-mentioned item 10.;

18. A use according to the above-mentioned item 17., in which, in the expression vector, the alkylated DNA repair enzyme is alkyladenine DNA glycosidase (AAG), and the thymidine kinase is a human herpes virus derived thymidine kinase.

19. A use according to the above-mentioned item 18., in which the expression vector further includes a gene sequence encoding AP endonuclease (APE1); and 20. An expression vector to be used in the selection of a genetic switch and a genetic circuit, the expression vector including a polynucleotide having a base sequence set forth in any one of SEQ ID NOS: 1 to 6 of the sequence listing.

Advantageous Effect of Invention

According to the present invention, it is possible to provide the selection method for a genetic switch and a genetic circuit, the selection method including: using cells transfected with an expression vector harboring a genetic circuit having a genetic switch expression sequence, and a gene sequence encoding a transcription regulatory factor whose expression is induced by a genetic switch encoded by the genetic switch expression sequence, and an expression vector having a gene sequence whose expression is controlled by the transcription regulatory factor; and in the presence of a compound that can induce cell death under expression of the gene sequence whose expression is controlled, incubating the cells, and collecting viable cells, and/or in the presence of a compound that can induce cell death under non-expression of the gene sequence whose expression is controlled, incubating the cells, and collecting viable cells. Specifically, it is possible to provide the selection method for a genetic switch and a genetic circuit, in which the gene sequence whose expression is controlled is a gene sequence encoding an alkylated DNA repair enzyme, such as a gene sequence encoding alkyladenine DNA glycosidase (AAG). Or, it is possible to provide the selection method for a genetic switch and a genetic circuit, in which the gene sequences, whose expression is controlled, are a gene sequence encoding an alkylated DNA repair enzyme and a gene sequence encoding a thymidine kinase, such as AAG and hsvTK. According to the present invention, it is also possible to provide the expression vector to be used in the selection method for a genetic switch and a genetic circuit according to the present invention, the expression vector containing at least a gene sequence encoding a thymidine kinase and a gene sequence encoding an alkylated DNA repair enzyme, and a promoter sequence operably linked to the two gene sequences upstream of the two gene sequences.

The method according to the present invention, unlike a conventional method, includes using a selection system having such properties that a genetic circuit transfected into cells causes cell death within a short time period when not properly outputted, and allows the cells to survive when properly outputted. Such selection system can conduct a selection operation within a short time period, specifically about 10 minutes to 60 minutes, and hence can conduct the selection of a genetic circuit, and the selection of a particularly complex genetic circuit as well, within a short time period as compared to the conventional method.

Therefore, according to the present invention, a genetic switch and genetic circuit with desired properties and/or functions can be selected and obtained within a short time period as compared to the conventional method. The method according to the present invention can be conducted rapidly with extremely high efficiency, and hence can serve as a platform for rapidly developing a genetic circuit with higher stringency, thereby being able to be employed as good means for synthetic biology.

BRIEF DESCRIPTION OF DRAWINGS

[FIG. 2-A] A plasmid map of Circuit-A, which is a model genetic circuit.

[FIG. 2-B] A plasmid map of Circuit-B, which is a model genetic circuit.

[FIG. 2-C] A plasmid map of Circuit-C, which is a model genetic circuit.

[FIG. 2-D] A plasmid map of Circuit-D, which is a model genetic circuit.

[FIG. 9-A] A schematic diagram illustrating a method of distinguishing Circuit-A and Circuit-B as model genetic circuits illustrated in FIG. 1 by PCR. In each of Circuit-A and Circuit-B, a certain region of the circuit containing part of a CI structural gene is amplified by PCR with the same primer set. Circuit-A contains the wild-type of the CI structural gene, while Circuit-B contains a truncated variant of the CI structural gene. Thus, a PCR product (367 bp) using Circuit-B as a template is shorter in length than a PCR product (639 bp) using Circuit-A as a template. Accordingly, PCR analysis of a mixture of both the circuits provides two bands corresponding to the different lengths. An abundance ratio between both the circuits is determined based on an intensity ratio between the bands.

[FIG. 9-B] An image showing results obtained by mixing a TK-deficient $E.$ $coli$ strain transfected with Circuit-A as one of the model genetic circuits illustrated in FIG. 1 (Switch-1) and a TK-deficient $E.$ $coli$ strain transfected with Circuit-B as one of the model genetic circuits illustrated in FIG. 1 (Switch-2), and subjecting the mixture to OFF selection, followed by ON selection. After each selection step, Switch-1 and Switch-2 were detected by PCR. In the figure, Lane 1 represents the result of Switch-1, Lane 2 represents the result of Switch-2, Lane 3 represents the result of the mixed cells, Lane 4 represents the result of the mixed cells subjected to OFF selection, and Lane 5 represents the results of the cells subjected to ON selection after the OFF selection (Experimental Example 7).

[FIG. 10] Schematic diagrams of various selector plasmids.

[FIG. 11] A plasmid map of plasmid pCI-gfp.

[FIG. 12-A] A plasmid map of ON-selector plasmid pTrc-aag (WT) containing a wild-type AAG gene.

[FIG. 12-B] A plasmid map of ON-selector plasmid pTrc-aag-ape1 containing a wild-type AAG gene and an Ape1 gene.

[FIG. 12-C] A plasmid map of plasmid pTrc-ape1 containing an Ape1 gene.

[FIG. 13-A] A plasmid map of dual selector plasmid pCI-aag-hsvTK (selector plasmid Ver. 1) containing a wild-type AAG gene and a human herpes virus gene.

[FIG. 13-B] A plasmid map of dual selector plasmid pCI-aag-hsvTK-ape1 (selector plasmid Ver. 2) containing a wild-type AAG gene, a human herpes virus gene, and an Ape1 gene.

[FIG. 13-C] A plasmid map of dual selector plasmid pCI-aag-hsvTK-ape1 (selector plasmid Ver. 2.1) containing an AAG (L180F) variant gene, a human herpes virus gene, and an Ape1 gene.

[FIG. 13-D] A plasmid map of dual selector plasmid pCI-aag-hsvTK-ape1 (selector plasmid Ver. 3) containing a wild-type AAG gene, a human herpes virus gene, and an Ape1 gene.

[FIG. 14] Graphs showing that an AAG gene functions as an ON-selector. When an alkylating agent-sensitive E. coli strain MV2157 transfected with a plasmid containing a gene for an AAG (E125A) variant in which the alkylated DNA repair enzyme activity of AAG was lost (□) was treated with MMS, the survival rate of the E. coli strain remarkably reduced in an MMS concentration-dependent manner (the panel (a)). Further, the decrease in the survival rate was already observed 15 minutes after the MMS treatment (the panel (b)). On the other hand, MV2157 transfected with a plasmid containing an AAG gene (○), as compared to the one transfected with a plasmid containing a gene for an AAG (E125A) variant, showed an up to $10^3$-fold viable cell count. The survival rate of the E. coli strain further increased through transfection with a plasmid containing APE1 in addition to the plasmid containing an AAG gene (●) (Example 2).

[FIG. 15-A] Graphs showing that through ON selection using AAG as an ON-selector, the selection of a genetic circuit was able to be conducted by MMS treatment for a short time period. In the figures, "λPR ON (●)" represents an MV2157 E. coli strain transfected with selector plasmid Ver. 2 (pCI-aag-hsvTK-ape1) and Circuit-C, and "λPR ON (□)" represents an MV2157 E. coli strain transfected with selector plasmid Ver. 2 (pCI-aag-hsvTK-ape1) and Circuit-D (Example 3).

[FIG. 15-B] A graph showing that when the MV2157 E. coli strain transfected with selector plasmid Ver. 2 (pCI-aag-hsvTK-ape1) and Circuit-C was further transfected with plasmid pCI-ape1 to increase the expression level of Ape1, the survival rate of the E. coli increased (Example 3).

[FIG. 18-A] A schematic diagram illustrating the steps of dual selection as a combination of OFF selection using an hsvTK gene as an OFF-selector and ON selection using an AGG gene as an ON-selector (Example 5).

[FIG. 18-B] Images showing output patterns of each fluorescence protein of a cell population under conditions of the presence and absence of AHL at each stage in the steps of the dual selection illustrated in FIG. 18-A. After the OFF selection had been conducted, colonies showing fluorescence with the addition of AHL, i.e., a switch strain having Circuit-C and expressing hsvTK was substantially absent, while in contrast, colonies showing no fluorescence with the addition of no AHL, i.e., those of a switch strain having Circuit-D and not expressing hsvTK were present in a large number. After the ON selection had been conducted following the OFF selection, in the switch strain having Circuit-D, which did not express AAG irrespective of the presence or absence of the addition of AHL, cell death was induced, and the switch strain having Circuit-B, which expressed AAG in the absence of AHL, evaded cell death due to MMS and survived (Example 5).

[FIG. 19] An image showing that when the switching time of the group of genes contained in a selector plasmid from a non-expression state (OFF) to an expression state (ON) was short, i.e., when culture in medium containing no AHL was 1 hour, cells containing Circuit-A and expressing full-length CI were mostly eliminated by selection, whereas only cells containing Circuit-B and expressing a truncated CI variant were picked out. This "picking" was not observed when a time interval between selection operations was sufficiently long, i.e., when culture in medium containing no AHL was for 6 hours. In the figure, NC represents a negative control, i.e., in this case, a sample not subjected to MMS treatment (Example 6).

DESCRIPTION OF EMBODIMENTS

Figure 1:
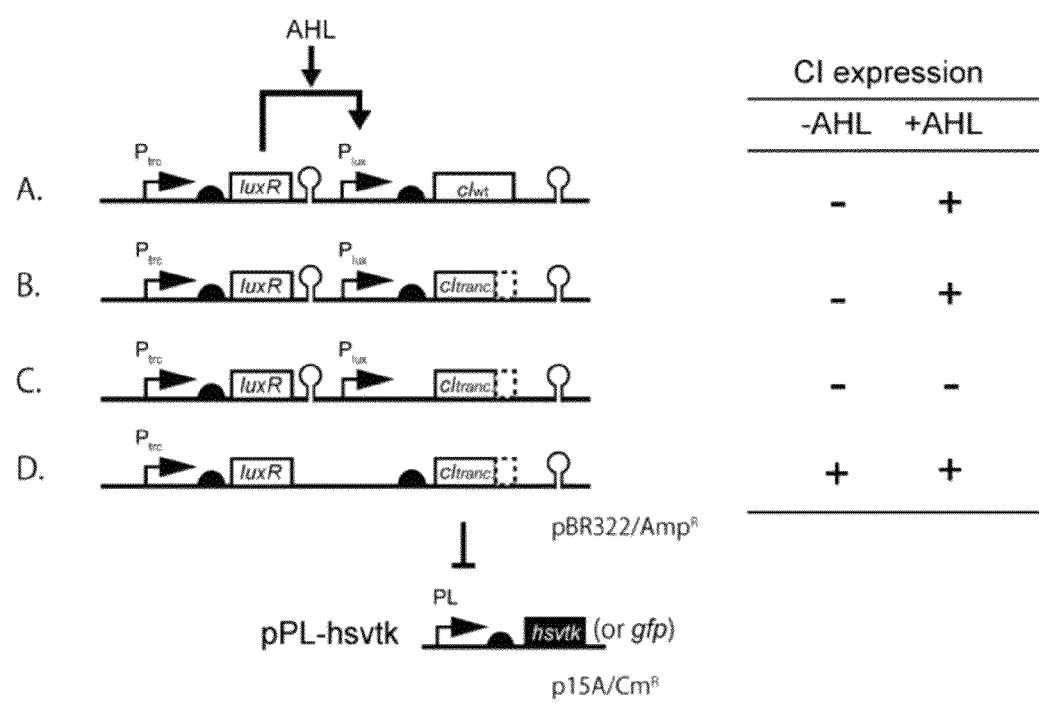
[FIG. 1] Schematic diagrams of four kinds of model genetic circuits and a diagram showing their functions. The left panel illustrates the schematic diagrams of the genetic circuits. The right panel shows the presence or absence of CI protein expression (CI expression) by each model genetic circuit depending on the presence or absence of an activating substance N-acyl-L-homoserine lactone (AHL).

The present invention relates to a developing method for a genetic switch and a genetic circuit, including selecting a desired genetic switch and genetic circuit from a library of a large number of genetic switches with different properties by using, as an indicator, cell death or cell death avoidance caused by the expression or non-expression of a gene whose expression is controlled by the action of each of the genetic switch and the genetic circuit having the genetic switch.

The term "genetic switch" refers to a molecule containing a transcription-activating domain, the molecule having a site to which a substance that can activate the molecule (activating substance) binds, preferably a protein of such kind. Such molecule is activated by the binding of the activating substance to change its function. That is, the binding of the activating substance affects the binding of the genetic switch to a target sequence, and as a result, the expression of a gene of interest is inhibited or induced. In other words, the "genetic switch" refers to a molecule containing a transcription-activating domain, the molecule having a site to which a substance that can activate the molecule binds and whose binding to a target sequence is caused or released by the binding of the substance. The term "genetic switch expression sequence" refers to a nucleic acid sequence encoding a genetic switch.

The term "activating substance for the genetic switch" refers to a substance that binds to the genetic switch to change the function of the genetic switch, consequently inducing direct or indirect expression regulation of a gene or a large number of genes, such as a compound of such kind. The "activating substance for the genetic switch" can also be called a "compound that activates the genetic switch." The activating substance differs for each genetic switch. A combination of the genetic switch and the activating substance may be exemplified by: LuxR, which is a vibrio-derived homoserine-lactone sensor and is an N-acyl-L-homoserine lactone (AHL) receptor protein, and AHL; an AraC protein and arabinose; or the like.

The term "target sequence of the genetic switch" refers to a nucleic acid sequence located 5' upstream of a gene encoding a target gene or the translation start of an active site thereof, the nucleic acid sequence controlling the transcription of the target gene. The target sequence of the genetic switch has a promoter activity. That is, the "target sequence of the genetic switch" may be a promoter sequence. It is preferred that a regulatory nucleic acid sequence having an enhancer activity be indirectly or directly bound to the target sequence of the genetic switch. When the genetic switch does not act on the target sequence of the genetic switch, the target gene is not expressed. That is, the action of the genetic switch on the target sequence of the genetic switch is regulated by the addition of the activating substance for the genetic switch, and the expression of the target gene is thus controlled.

The term "promoter" refers to a region on DNA that determines the site of transcription initiation of a gene and directly regulates the frequency of the transcription initiation, the region being a nucleic acid sequence that starts transcription upon the binding of an RNA polymerase. The promoter is appropriately selected and used depending on the kind of host cells to be used. When bacteria are used as the hosts, any promoter may be used without any particular limitation as long as it allows expression in the host cells such as E. coli. Examples thereof may include promoters derived from E. coli and phage, such as a λPR promoter, a PL promoter, a trp promoter, and a lac promoter. An artificially designed and modified promoter such as a tac promoter may be used. When yeast is used as the host, any promoter may be used without any particular limitation as long as it enables expression in yeast. Examples thereof may include a gal1 promoter, a gal10 promoter, a heat shock protein promoter, an MFα1 promoter, a PHOS promoter, a PGK promoter, a GAP promoter, an ADH promoter, and an AOX1 promoter. When animal cells are used as the hosts, it is preferred that a recombinant vector be autonomously replicable in the cells, and at the same time, be constituted of the promoter, an RNA splice site, a gene of interest, a polyadenylation site, and a transcription termination sequence. Further, an origin of replication may be contained as desired. As the promoter, there may be used an SRα promoter, an SV40 promoter, an LTR promoter, a CMV promoter, and the like. Further, an early gene promoter of cytomegalovirus or the like may be used.

The term "genetic circuit" refers to a controllable gene expression system containing a combination of a nucleic acid sequence encoding a genetic switch and a target sequence of the genetic switch, and enabling gene expression. More specifically, the term refers to a nucleic acid containing a nucleic acid sequence encoding a genetic switch, and a transcription/translation regulatory region having a regulatory DNA element such as a promoter which the genetic switch acts on.

In the construction of genetic circuits, through the selection of those in a triggered state when gene expression should be ON(ON selection) and/or the selection of those in a repressed state in a situation where gene expression should be OFF (OFF selection), it is possible to select/obtain genetic circuits with arbitrary output properties. Successive conduction of the ON selection/OFF selection allows various genetic switches (or genetic circuits) to be rapidly developed.

The term "ON selection" refers to the selection of those in a triggered state when gene expression should be ON. In other words, the term "ON selection" refers to selection by selective removal of a genetic switch in OFF (repressed state) under such conditions that the genetic switch should be ON (triggered state). In order to conduct the ON selection, a gene "whose expression is essential for the survival of host cells" (ON-selector) is placed under control of a library of genetic switches and genetic circuits to be subjected to the selection. Genetic switches and genetic circuits that are not triggered under such conditions that the genetic switches should be ON (triggered state) and thus cannot express the ON-selector downstream thereof are selectively removed together with cells transfected therewith. That is, in the ON selection, when the expression of a gene whose expression is controlled by the action of each of a genetic switch and a genetic circuit is ON, cell death is avoided. As a substance that causes cell death within a short time period, there are known an alkylating agent, an organic solvent, ultraviolet light/radiation, heat, an acid/alkali, an oxidizing agent, and the like. When a gene that imparts resistance against any such substance is used as the selector, a system in which "only those whose output is ON during the selection survive" can be constructed.

The term "OFF selection" refers to the selection of those in a repressed state in a situation where gene expression should be OFF. In other words, the term "OFF selection" refers to selection by removal a genetic switch that allows gene expression under such conditions that the genetic switch should be OFF (repressed state), i.e., a leaky genetic switch. In order to conduct the OFF selection, a gene "whose expression causes cell death of host cells" (OFF-selector) is placed under control of a library of genetic switches and genetic circuits to be subjected to the selection. A genetic switch that mistakenly expresses the OFF-selector downstream thereof under such conditions that the genetic switch should be OFF (repressed state) and a leaky genetic circuit are selectively removed together with the host. That is, in the OFF selection, when the expression of a gene whose expression is controlled by the action of each of a genetic switch and a genetic circuit is OFF, cell death is avoided. As a substance that causes cell death within a short time period, there are known a gene modifier, an alkylating agent, an organic solvent, ultraviolet light/radiation, heat, an acid/alkali, an oxidizing agent, and the like. When a gene involved in cell death due to any such substance or a gene that enhances sensitivity to any such substance is used as the selector, a system in which "only those whose output is OFF during the selection survive" can be constructed.

The term "dual selection" refers to ON selection and OFF selection conducted in combination. In the dual selection, any one of the ON selection and the OFF selection may be conducted first. The dual selection may be conducted only once, or may be conducted a plurality of times. It is suitable that the dual selection be preferably conducted a plurality of times successively. When the dual selection is conducted a plurality of times, a desired genetic switch and genetic circuit can be obtained from the library of genetic switches and genetic circuits at a high enrichment factor.

The term "selector" refers to means to be employed for the selection of a genetic switch and a genetic circuit having the genetic switch, and refers to, for example, a gene sequence whose expression is controlled by the action of each of the genetic switch and the genetic circuit or an expression vector having the gene sequence.

The term "ON-selector" refers to means to be employed for ON selection, and refers to, for example, a gene "whose expression is essential for the survival of host cells" or an expression vector containing the gene.

The term "OFF-selector" refers to means to be employed for OFF selection, and refers to, for example, a gene "whose expression causes cell death of host cells" or an expression vector containing the gene.

The term "dual selector" refers to a selector having both the function of an ON-selector and the function of an OFF-selector. Therefore, the dual selector is used for both of ON selection and OFF selection. The dual selector may be exemplified by an expression vector containing both of a gene "whose expression is essential for the survival of host cells" and a gene "whose expression causes cell death of host cells."

The term "expression vector" refers to DNA that transfers an exogenous gene to host cells, in other words, vector DNA, the DNA allowing a gene of interest to be expressed in the host cells. The vector DNA is not particularly limited as long as it is replicable in the host, and is appropriately selected depending on the kind of the host and intended use. The vector DNA may be vector DNA lacking a part of DNA except a part necessary for replication as well as vector DNA obtained by extracting naturally occurring DNA. Representative examples of the vector DNA may include vector DNAs derived from a plasmid, a bacteriophage, and a virus.

Examples of the plasmid DNA may include an *E. coli*-derived plasmid, a *Bacillus subtilis*-derived plasmid, and a yeast-derived plasmid. Examples of the bacteriophage DNA may include λ phage. Examples of the virus derived vector DNA may include vectors derived from animal viruses such as a retrovirus, a vaccinia virus, an adenovirus, a papovavirus, SV40, a fowlpox virus, and a pseudorabies virus, or vectors derived from insect viruses such as a baculovirus. Other examples of the vector DNA may include transposon-derived, insertion element-derived, yeast chromosome element-derived vector DNAs. Alternatively, for example, there may be given vector DNA produced by combining the above-mentioned materials, such as vector DNA prepared by combining genetic elements of a plasmid and a bacteriophage (e.g., a cosmid or a phagemid). It is necessary to incorporate a gene of interest into the vector DNA so that the gene of interest may be expressed, and at least the gene of interest and a regulatory DNA element such as a promoter are included as the constituent elements of the vector DNA. In addition to those elements, if desired, gene sequences carrying information on replication and control may be incorporated in combination into the vector DNA by a method known per se. Examples of such gene sequences may include: cis-elements such as a ribosome binding sequence, a terminator, a signal sequence, and an enhancer; a splicing signal; and selection markers (e.g., a dihydrofolate reductase gene, an ampicillin resistance gene, and a neomycin resistance gene). One or more kinds of gene sequences selected therefrom may be incorporated into the vector DNA.

A genetic engineering technology known per se may be applied as a method of incorporating the gene of interest into the vector DNA. For example, there may be employed a method involving treating the gene of interest with an appropriate restriction enzyme to cleave the gene at a specific site, mixing the resultant with vector DNA treated in the same manner, and recombining them with a ligase. Alternatively, desired vector DNA may be obtained by ligating the gene of interest with an appropriate linker, and inserting the resultant into a multiple cloning site of a vector suited for the purpose.

A method of transfecting the expression vector into host cells is not particularly limited as long as it is a transfection method by which the vector DNA can be transfected into the host cells and the gene of interest can be expressed in the host cells. Any known method appropriately selected depending on the kind of the host cells may be employed. Examples thereof may include an electroporation method, a calcium phosphate method, and a lipofection method.

More specifically, the present invention relates to a selection method for a genetic switch and a genetic circuit, including, through the use of cells transfected with: an expression vector harboring a genetic circuit having a genetic switch expression sequence, and a gene sequence encoding a transcription regulatory factor whose expression is induced by a genetic switch encoded by the genetic switch expression sequence; and an expression vector having a gene sequence whose expression is controlled by the transcription regulatory factor, in the presence or absence of a compound that activates the genetic switch, incubating the cells with the addition of a compound that can induce cell death under expression of the gene sequence whose expression is controlled; and collecting viable cells, and/or in the presence or absence of a compound that activates the genetic switch, incubating the cells with the addition of a compound that can induce cell death under non-expression of the gene sequence whose expression is controlled; and collecting viable cells.

The term "transcription regulatory factor" as used herein refers to a protein type factor that works by acting on a regulatory DNA element, more specifically, a promoter. The transcription regulatory factors can be broadly classified into a transcription repression factor (also referred to as "repressor") and a transcription activation factor (also referred to as "activator"). The transcription repression factor acts on a regulatory DNA element to repress the transcription of a gene, thereby reducing the expression level of the gene. The transcription activation factor acts on a regulatory DNA element to promote the transcription of a gene, thereby increasing the expression level of the gene. The transcription repression factor and the transcription activation factor may each be used in the present invention. Any known respective factors may be used as the transcription repression factor and the transcription activation factor. A CI protein may be given as a preferred example of the transcription repression factor. The CI protein binds to each of the promoter regions, promoter PL and promoter PR (i.e., OL and OR), to strongly blocks the start of transcription from each of the promoters. Other preferred transcription regulatory factors that may be used include LacI, TetR, AraC, CAP, LacI, and LuxR, and the like.

In the present invention, the expression vector having a gene sequence whose expression is controlled by the transcription regulatory factor may be an expression vector having the following two gene sequences: a first gene sequence whose expression is controlled by the transcription regulatory factor; and a second gene sequence whose expression is controlled by the transcription regulatory factor. Alternatively, the expression vector having a gene sequence whose expression is controlled by the transcription regulatory factor may be a combination of the following two expression vectors: an expression vector having the first gene sequence whose expression is controlled by the transcription regulatory factor; and an expression vector having the second gene sequence whose expression is controlled by the transcription regulatory factor. In this context, the first gene sequence is a gene sequence encoding a protein different from that of the second gene sequence does. When one of the first gene sequence and the second gene sequence is a gene sequence for ON selection, the other is preferably a gene sequence for OFF selection. That is, the selection method for a genetic switch and a genetic circuit according to the present invention can be efficiently conducted through selection involving using, as indicators, cell death avoidance by the expression of one of the gene sequences, and cell death avoidance by the non-expression of the other gene sequence.

The term "gene sequence whose expression is controlled by the transcription regulatory factor" refers to a gene sequence downstream of a regulatory DNA element on which the transcription regulatory factor acts, the expression of the gene sequence being promoted or repressed by the action of the transcription regulatory factor. The expression of the gene sequence refers to the following series of processes: the information of the gene is transcribed into mRNA, which is further translated into the amino acid sequence of a protein encoded by the gene. When the expression is promoted, the protein encoded by the gene is produced, resulting in an increased amount thereof, whereas when the expression is repressed, the protein encoded by the gene is not produced, resulting in a reduced amount thereof.

Any sequence may be used as the "gene sequence whose expression is controlled by the transcription regulatory factor" to be used in the present invention as long as it is the sequence of a gene that imparts resistance against a substance that causes cell death within a short time period, such as a gene modifier, an alkylating agent, an organic solvent, ultraviolet light/radiation, heat, an acid/alkali, an oxidizing agent, or the like, or the sequence of a gene involved in cell death due to the substance or of a gene that enhances sensitivity to the substance. Specifically, the sequence may be preferably exemplified by a gene sequence encoding an alkylated DNA repair enzyme or a gene sequence encoding a thymidine kinase (hereinafter sometimes abbreviated as "TK"). Such gene sequence to be used in the present invention is not limited to those examples, and any gene sequence may be used as long as it is the sequence of a gene involved, in cells, in cell death or cell death avoidance thereof.

The term "gene sequence encoding an alkylated DNA correction enzyme" as used in the present invention refers to a nucleic acid sequence encoding an enzyme that acts on an alkylated nucleotide in alkylated DNA to cause cleavage. A deoxyribose chain after the cleavage by the alkylated DNA correction enzyme is further cleaved by AP endonuclease (APE1). Next, DNA at the cleaved site is repaired by a DNA polymerase and a ligase on the basis of the information of the complementary strand.

When alkylation occurs in genomic DNA, the alkylated nucleotide causes the inhibition of DNA replication or a genetic mutation, consequently causing cell death. For example, when cells are treated with methanesulfonic acid (MMS) as an alkylating agent, MMS passes through the cell membrane to methylate the 3-position of adenine in the genomic DNA. Adenine that remains methylated causes the inhibition of DNA replication or a genetic mutation, thus causing cell death.

The gene sequence encoding an alkylated DNA correction enzyme may be exemplified by a gene sequence encoding alkyladenine DNA glycosidase (AAG) or a gene sequence encoding O6-methylguanine-DNA transferase (MGMT), more preferably a gene sequence encoding AAG. Other examples thereof may include gene sequences each encoding a repair enzyme for 3-alkyladenine, such as E. coli-derived ones including a gene sequence encoding AlkA (glycosylase) or AlkB (alkyltransferase). In addition, there may be preferably used a gene sequence encoding an alkylated DNA repair enzyme having an enhanced enzymatic activity or a gene sequence encoding an alkylated DNA repair enzyme having resistance against an alkylating agent, both of which are variants of the above-mentioned genes. As a preferred example thereof, there may be given a gene sequence encoding a variant in which leucine at position 180 in the amino acid sequence of AAG is substituted by phenylalanine (AAG (L180F)). This variant is an AAG variant obtained as a variant having resistance against methylsulfonic acid (MMS) as an alkylating agent (Chen, et al., DNA Repair, 7, 1731 (2008)).

When the gene sequence encoding an alkylated DNA correction enzyme is used as the "gene sequence whose expression is controlled by the transcription regulatory factor," it is preferred to place, downstream of the gene sequence, a gene sequence encoding AP endonuclease (APE1). The reason is as follows. In the process of alkylated DNA repair, the alkylated DNA correction enzyme acts and then APE1 acts, and thus the DNA repair proceeds. Accordingly, when the gene sequence encoding an alkylated DNA correction enzyme is used in combination with the gene sequence encoding APE1, the avoidance of cell death due to DNA alkylation can be more certainly conducted.

A promoter sequence to be operably linked to the gene sequence encoding an alkylated DNA correction enzyme upstream of the gene sequence is not particularly limited as long as it can express the gene sequence encoding an alkylated DNA correction enzyme with the action of the gene product of a genetic switch or a genetic circuit, and a known promoter sequence may be used.

The term "gene sequence encoding a thymidine kinase" refers to a gene sequence encoding an enzyme that catalyzes phosphorylation of deoxythymidine. TK plays an important role as a regulatory factor for DNA synthesis. The supply of deoxythymidine triphosphate (dTTP) as a direct precursor substance for DNA synthesis in cells relies on a de novo pathway and a salvage pathway. The de novo pathway, which synthesizes dTTP via deoxythymidine monophosphate (dTMP) synthesis, is known to be stopped by the addition of 5-fluorouracil to the pathway (Cohen, S S, et al., The Mode of Action of 5-Fluorouracil and Its Derivatives. Proc Natl Acad Sci USA, 44, 1004-12 (1958); Yagil, E, et al., Phosphorolysis of 5-fluoro-2'-deoxyuridine in *Escherichia coli* and its inhibition by nucleosides. J Bacteriol, 108, 760-4 (1971)). 5-Fluorouracil and derivatives thereof are metabolized in cells to 5-fluoro-2'-deoxyuridine monophosphate (5FdUMP). 5FdUMP is an inhibitor of dTMP synthase (ThyA), and its presence inhibits intracellular synthesis of dTMP. Under such circumstances, the proliferation of cells depends on the salvage pathway, which synthesizes dTTP through the use of exogenous deoxythymidine (dT). If the cells have TK, dTMP can be synthesized from dT by the salvage pathway, which allows their survival. On the other hand, when TK is absent, their proliferation is completely abolished. The transfection of TK into TK-deficient strain cells restores the salvage pathway. Through the utilization of such mechanism, researches have been conducted on an activity/function-based selection method with the thymidine kinase and its related enzymatic activities (Black, M E, et al., Creation of drug-specific herpes simplex virus type1 thymidine kinase mutants for gene therapy. Proc Natl Acad Sci USA, 93, 3525-9 (1996)).

Meanwhile, it is known that various nucleoside analogs are activated in cells by nucleotide metabolism enzymes such as the thymidine kinase to cause cell death, and the thymidine kinase has long been studied as a suicide gene for gene therapy as well (Black, M E, et al., Identification of important residues within the putative nucleoside binding site of HSV-1 thymidine kinase by random sequence selection: analysis of selected mutants in vitro. Biochemistry, 32, 11618-26 (1993); Dube, D K, et al., Selection of new biologically active molecules from random nucleotide sequences. Gene, 137, 41-7 (1993)).

The gene sequence encoding a thymidine kinase is not particularly limited, and examples thereof may include gene sequences encoding mammalian cell-derived and virus derived thymidine kinases, preferably a gene sequence encoding a human herpes virus derived thymidine kinase.

A promoter sequence operably linked to the gene sequence encoding a thymidine kinase upstream of the gene sequence is not particularly limited as long as it is a promoter sequence which has a function of expressing a gene encoding a thymidine kinase, and on which the gene product of a genetic switch or genetic circuit to be tested acts, and a known promoter sequence may be used.

In the present invention, the "gene sequence whose expression is controlled by the transcription regulatory factor" is used in combination with a substance, preferably a compound, that can induce cell death under expression of the gene sequence, or a substance, preferably a compound, that can induce cell death under non-expression of the gene sequence.

The term "compound that can induce cell death under expression of the gene sequence whose expression is controlled" refers to a compound that can cause cell death upon production of a protein encoded by the gene sequence.

For example, a mutagenic nucleoside may be given as a compound that can induce cell death under expression of the gene sequence encoding a thymidine kinase. The mutagenic nucleoside is incorporated into the genome via the salvage pathway of thymidine to cause a genetic mutation, thereby inducing cell death. The mutagenic nucleoside is not particularly limited as long as it causes a mutation in a gene upon incorporation into the gene to induce cell death, and may be a naturally occurring mutagenic nucleoside, or may be an artificially produced mutagenic nucleoside. Specifically, the mutagenic nucleoside may be preferably exemplified by an artificial nucleoside 6-(β-D-2-deoxyribo-furanosyl)-3,4-dihydro-8H-pyrimido[4,5-c][1,2]oxazin-7-one (dP). Like other nucleosides, dP is incorporated into the genome via the salvage pathway of thymidine. While many other toxic nucleosides are chain terminators of chromosomal DNA synthesis, dP is a mutagenic nucleoside that is incorporated into the genome to frequently cause genetic mutations (Negishi, K, et al., Binding specificities of the mismatch binding protein, MutS, to oligonucleotides containing modified bases. Nucleic Acids Res Suppl, 221-2 (2001)). Therefore, in cells expressing a thymidine kinase, the addition of dP induces cell death, but in cells deficient in thymidine kinase, the addition of dP does not induce cell death. The genotoxicity of dP is low, and is such that the addition of 37 μM dP only kills 80% of an E. coli cell population (Negishi, K, et al., Saturation of DNA mismatch repair and error catastrophe by a base analogue in Escherichia coli. Genetics, 161, 1363-71 (2002)). In the cells expressing a thymidine kinase, although the addition of dP does not physically destroy chromosomes, genetic information is irreversibly deteriorated and hence their proliferation capacity is lost within a short time period of 5 minutes to 15 minutes.

The concentration of the mutagenic nucleoside is not particularly limited as long as it is a concentration at which the mutagenic nucleoside causes a mutation in a gene to induce cell death upon incorporation into the gene, and the concentration may be determined by simple repeated experiments. For example, dP is used at a concentration of 50 nM to 1 μM, more preferably 100 nM. A cell concentration at the time of treatment with the mutagenic nucleoside is not particularly limited, and may be determined by simple repeated experiments. For example, an appropriate cell concentration is $10^5$ cells/mL to $10^9$ cells/mL, more preferably $10^6$ cells/mL to $10^8$ cells/mL, even more preferably approximately $10^7$ cells/mL. Further, cells have higher sensitivity to a drug when in a logarithmic growth phase, and hence cells in a logarithmic growth phase are preferably used. An incubation time of the mutagenic nucleoside and the cells is not particularly limited, and may be determined by simple repeated experiments. Cell death due to mutations by the mutagenic nucleoside is caused within an extremely short time period, and hence, for example, when dP is used, the incubation of dP and the cells has only to be conducted for 5 minutes to 12 hours, preferably 5 minutes to 60 minutes, more preferably 5 minutes to 30 minutes, even more preferably 30 minutes. Medium to be used at the time of the treatment of the cells with the mutagenic nucleoside may be exemplified by typically used medium such as LB medium or M9-glucose medium.

The term "compound that can induce cell death under non-expression of the gene sequence whose expression is controlled" refers to a compound that can cause cell death when the protein encoded by the gene sequence is not produced, in other words, a compound that induces cell death, the induction being inhibited by such protein.

For example, an alkylating agent may be given as a compound that can induce cell death under non-expression of the gene sequence encoding an alkylated DNA repair enzyme. The alkylating agent refers to a drug that contains a compound having a molecular structure called an alkyl group such as a methyl group, an ethyl group, or a propyl group, and that has a function of alkylating DNA, i.e., a function of acting on DNA to change it into a polymer having an alkyl group. The alkylation, such as methylation, of DNA destroys the genetic information carried by the DNA, causing cell death. When the gene sequence encoding an alkylated DNA repair enzyme is expressed, the DNA alkylated by the alkylating agent is repaired and hence cell death is avoided.

The alkylating agent is not particularly limited as long as it has an action of alkylating DNA, and any known alkylating agent may be used. Specifically, the alkylating agent may be preferably exemplified by methanesulfonic acid (MMS). MMS passes through the cell membrane to methylate the 3-position of adenine in genomic DNA. Adenine that remains methylated causes the inhibition of DNA replication or a genetic mutation, thus causing cell death. Other preferred examples of the alkylating agent which may be used may include methyl iodide, ethyl methanesulfonate (EMS), and N-methyl-N'-nitro-nitrosoguanidine (MNNG).

The concentration of the alkylating agent is not particularly limited as long as it is a concentration at which the alkylating agent exhibits an action of alkylating DNA, and the concentration may be determined by simple repeated experiments. For example, MMS is used at a concentration of 0.1% to 0.4%, preferably 0.2% to 0.3%, more preferably 0.2%, in an another expression, 10 mM to 50 mM, preferably 20 mM to 40 mM, more preferably 20 mM. When a cell concentration at the time of treatment with the alkylating agent is excessively low, cell death due to the alkylating agent is caused irrespective of the presence or absence of an alkylated DNA repair enzyme, and hence an appropriate concentration is, for example, $10^6$ cells/mL to $10^8$ cells/mL, more preferably $10^6$ cells/mL to $10^7$ cells/mL, even more preferably approximately $10^7$ cells/mL. Further, cells have higher sensitivity to a drug when in a logarithmic growth phase, and hence cells in a logarithmic growth phase are preferably used. An incubation time of the alkylating agent and the cells is not particularly limited, and may be determined by simple repeated experiments. Cell death due to the alkylation of DNA by the alkylating agent is caused within a short time period, and hence, for example, when MMS is used, the incubation of MMS and the cells has only to be conducted for 15 minutes to 45 minutes, preferably 15 minutes to 30 minutes, more preferably 30 minutes. Conditions under which DNA in the cells is subjected to treatment for alkylation with the alkylating agent are determined depending on the combination of the concentration of the alkylating agent, the cell concentration, and the incubation time. Specifically, when MMS is used as the alkylating agent and the concentration of MMS is about 0.2%, an appropriate number of cells is $10^6$ cells/mL to $10^7$ cells/mL. In addition, when the concentration of MMS is about 0.2% and the number of cells is $10^7$ cells/mL, an appropriate incubation time is 5 minutes to 45 minutes, e.g., 30 minutes. In order to sufficiently obtain the action of the alkylating agent, it is preferred to use, as medium to be used at the time of the treatment of the cells with the alkylating agent, minimal medium constituted of only essential substances, such as M9 medium for E. coli.

In the present invention, the term "cell" refers to a unit of life that is a basic structural/functional unit of an organism, has nucleic acid molecules for carrying genetic information, and is formed of a membrane structure for isolation from the outside world and cytoplasm thereinside. The cells to be used in the present invention may be any of prokaryotic cells and isolated eukaryotic cells, but are preferably prokaryotic cells having short cell cycles and high proliferation rates. Cells having such nature are useful for a rapid selection method for a genetic switch and a genetic circuit. E. coli is more preferably used. Even more preferably used are cells modified so as to show high sensitivity to the compound that induces cell death to be used in the present invention. Preferred examples of the modified cells may include thymidine kinase-deficient cells, alkylating agent-sensitive cells, and alkylating agent-hypersensitive and thymidine kinase-deficient cells. Specific examples thereof may include a thymidine kinase-deficient E. coli strain, an alkylating agent-sensitive E. coli strain, and an alkylating agent-hypersensitive and thymidine kinase-deficient E. coli strain. Any known ones may be used as such modified cells. The thymidine kinase-deficient cells, such as the thymidine kinase-deficient E. coli strain, are deficient in thymidine kinase and hence can avoid cell death due to the addition of dP. However, when a thymidine kinase is expressed in such cells, the addition of dP causes cell death. Therefore, when the selection of a genetic switch and a genetic circuit is conducted by using, as a selector, an expression vector containing a gene encoding a thymidine kinase and using, as an indicator, cell death to be caused by the addition of dP, the thymidine kinase-deficient cells are preferably used as cells to be transfected with the expression vector. The alkylation-sensitive cells, such as the alkylating agent-sensitive E. coli strain, have high sensitivity to the action of an alkylating agent and hence cell death is easily caused by the addition of the alkylating agent. However, when a methylated DNA repair enzyme is expressed in such cells, cell death due to the addition of the alkylating agent is avoided. Therefore, when the selection of a genetic switch and a genetic circuit is conducted by using, as a selector, an expression vector containing a gene encoding a methylated DNA repair enzyme and using, as an indicator, cell death to be caused by the addition of the alkylating agent, the alkylating agent-sensitive cells are preferably used as cells to be transfected with the expression vector. The alkylating agent-hypersensitive and thymidine kinase-deficient cells, such as the alkylating agent-hypersensitive and thymidine kinase-deficient E. coli strain, are deficient in thymidine kinase and hence can avoid cell death due to the addition of dP. However, when a thymidine kinase is expressed in such cells, the addition of dP causes cell death. Further, those cells have high sensitivity to the action of the alkylating agent, and hence easily undergo cell death by the addition of the alkylating agent. However, when a methylated DNA repair enzyme is expressed in such cells, the cell death due to the addition of the alkylating agent is avoided. Therefore, when the selection of a genetic switch and a genetic circuit is conducted by using, as a selector, an expression vector containing a gene encoding a methylated DNA repair enzyme and a gene encoding a thymidine kinase and using, as an indicator, the avoidance of cell death to be caused by the addition of dP and cell death to be cause by the addition of the alkylating agent, the alkylating agent-sensitive cells or the thymidine kinase-deficient cells are preferably used, and the alkylating agent-hypersensitive and thymidine kinase-deficient cells are more preferably used.

The term "cell death" as used in the present invention refers to a state in which cell functions such as proliferation capacity are lost. The cell death in the present invention refers to, for example, a state in which, after cells of E. coli or the like have been cultured on solid medium, an ability to proliferate from a single cell to form a colony of cells of a certain size that allows counting by visual observation or larger is lost. The term "cell death" may encompass active cell death (apoptosis) for positively removing, for example, unnecessary cells or damaged cells occurring owing to physiological or pathological factors, and passive cell death (necrosis) occurring in response to exogenous factors as well.

The term "viable cell" refers to a cell normally harboring cell functions such as proliferation capacity. The term refers to, for example, such a cell having an ability to proliferate from a single cell to form a colony of cells of a certain size that allows counting by visual observation or larger after cells of E. coli or the like have been cultured on solid medium.

The term "collecting viable cells" refers to the taking out of surviving cells from a culture obtained by culturing cells. In a simple manner, the recovery of surviving viable cells can be conducted by subjecting a culture containing surviving viable cells to centrifugation to remove a supernatant, and then washing the pellet with an appropriate isotonic buffer such as phosphate buffered saline.

In an aspect of the present invention, there is provided a selection method for a genetic switch and a genetic circuit, involving: causing alkylating agent-sensitive cells to express an expression vector containing a gene sequence encoding an alkylated DNA repair enzyme and an expression vector containing a genetic switch or a genetic circuit; and using, as an indicator, cell death or cell death avoidance due to the expression of the gene in the presence of an alkylating agent, or cell death or cell death avoidance due to the non-expression of the gene in the presence of the alkylating agent. The alkylating agent-sensitive cells undergo cell death in the presence of the alkylating agent, but survive when the expression of the gene encoding an alkylated DNA repair enzyme is induced. Through the utilization of such survival of the alkylating agent-sensitive cells through the induction of the expression of the gene encoding an alkylated DNA repair enzyme, it is possible to conduct the selection of a genetic switch or genetic circuit placed so as to control the expression of the gene encoding an alkylated DNA repair enzyme (ON selection).

The expression vector containing a gene sequence encoding an alkylated DNA repair enzyme is preferably an expression vector harboring at least: (a) a gene sequence encoding an alkylated DNA repair enzyme; and (b) a promoter sequence operably linked to the gene sequence according to the item (a) upstream of the gene sequence. Further, the expression vector containing a genetic switch or a genetic circuit is preferably an expression vector harboring at least: (c) another promoter sequence different from the promoter sequence according to the item (b), the another promoter sequence being operably linked to a genetic switch expression sequence downstream thereof; (d) the genetic switch expression sequence; (e) a target sequence of a genetic switch encoded by the genetic switch expression sequence; and (f) a gene sequence having the target sequence operably linked thereto, the gene sequence encoding a transcription regulatory factor that operates on the promoter sequence according to the item (b).

More specifically, an aspect of the present invention relates to a selection method for a genetic switch and a genetic circuit, the selection method including: using cells transfected with an expression vector harboring at least sequences according to the following items (a) and (b):
(a) a gene sequence encoding an alkylated DNA repair enzyme; and
(b) a promoter sequence operably linked to the gene sequence according to the item (a) upstream of the gene sequence, and an expression vector harboring at least sequences according to the following items (c) to (f):

(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription regulatory factor that operates on the promoter sequence according to the item (b); and
(1) when the gene sequence encoding a transcription regulatory factor according to the item (f) is a transcription repression factor, in the absence of a compound that activates the genetic switch, incubating the cells with the addition of an alkylating agent, and collecting viable cells, or
(2) when the gene sequence encoding a transcription regulatory factor according to the item (f) is a transcription activation factor, in the presence of a compound that activates the genetic switch, incubating the cells with the addition of an alkylating agent, and collecting viable cells.

A preferred aspect of the present invention relates to a selection method for a genetic switch and a genetic circuit, the selection method including: using an alkylating agent-hypersensitive E. coli strain transfected with
an expression vector harboring at least sequences according to the following items (a) and (b):
(a) a gene sequence encoding alkyladenine DNA glycosidase (AAG); and
(b) a promoter sequence operably linked to the gene sequence according to the item (a) upstream of the gene sequence, and
an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription repression factor that operates on the promoter sequence according to the item (b); and
in the absence of a compound that activates the genetic switch, incubating the E. coli strain with the addition of methanesulfonic acid (MMS), and collecting viable cells.

A more preferred aspect of the present invention relates to a selection method for a genetic switch and a genetic circuit, the selection method including: using an alkylating agent-hypersensitive E. coli strain transfected with
an expression vector harboring at least sequences according to the following items (a) and (b):
(a) a gene sequence encoding alkyladenine DNA glycosidase (AAG); and
(b) a promoter sequence operably linked to the gene sequence according to the item (a) upstream of the gene sequence, and
an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a CI protein that operates on the promoter sequence according to the item (b); and in the absence of a compound that activates the genetic switch, incubating the E. coli strain with the addition of methanesulfonic acid (MMS) for 15 minutes to 60 minutes, and collecting viable cells.

Another preferred aspect of the present invention relates to a selection method for a genetic switch and a genetic circuit, the selection method including: using an alkylating agent-hypersensitive E. coli strain transfected with
an expression vector harboring at least sequences according to the following items (a) and (b):
(a) a gene sequence encoding alkyladenine DNA glycosidase (AAG) and a gene sequence encoding AP endonuclease (APE1); and
(b) a promoter sequence operably linked to the two gene sequences according to the item (a) upstream of the two gene sequences, and
an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription regulatory factor that operates on the promoter sequence according to the item (b); and
(1) when the gene sequence encoding a transcription regulatory factor according to the item (f) is a transcription repression factor, in the absence of a compound that activates the genetic switch, incubating the E. coli strain with the addition of methanesulfonic acid (MMS), and collecting viable cells, or
(2) when the gene sequence encoding a transcription regulatory factor according to the item (f) is a transcription activation factor, in the presence of a compound that activates the genetic switch, incubating the E. coli strain with the addition of MMS, and collecting viable cells.

A preferred aspect of the present invention relates to a selection method for a genetic switch and a genetic circuit, the selection method including: using an alkylating agent-hypersensitive E. coli strain transfected with
an expression vector harboring at least sequences according to the following items (a) and (b):
(a) a gene sequence encoding alkyladenine DNA glycosidase (AAG) and a gene sequence encoding AP endonuclease (APE1); and
(b) a promoter sequence operably linked to the two gene sequences according to the item (a) upstream of the two gene sequences, and
an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and (f) a gene sequence having the target sequence operably linked thereto, the gene sequence encoding a transcription repression factor that operates on the promoter sequence according to the item (b); and in the absence of a compound that activates the genetic switch, incubating the *E. coli* strain with the addition of methanesulfonic acid (MMS), and collecting viable cells.

A more preferred aspect of the present invention relates to a selection method for a genetic switch and a genetic circuit, the selection method including: using an alkylating agent-hypersensitive *E. coli* strain transfected with an expression vector harboring at least sequences according to the following items (a) and (b):

(a) a gene sequence encoding alkyladenine DNA glycosidase (AAG) and a gene sequence encoding AP endonuclease (APE1); and (b) a promoter sequence operably linked to the two gene sequences according to the item (a) upstream of the two gene sequences, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a CI protein that operates on the promoter sequence according to the item (b); and in the absence of a compound that activates the genetic switch, incubating the *E. coli* strain with the addition of methanesulfonic acid (MMS) for 15 minutes to 60 minutes, and collecting viable cells.

In the present invention, there is also employed a selection method for a genetic switch and a genetic circuit, involving: causing thymidine kinase-deficient cells to express an expression vector containing an expression sequence for a gene encoding a thymidine kinase and an expression vector containing a genetic switch or a genetic circuit; and using, as an indicator, cell death due to the expression of the gene in the presence of a mutagenic nucleoside, or cell death avoidance due to the non-expression of the gene in the presence of the mutagenic nucleoside. In the thymidine kinase-deficient cells, when the expression of the gene encoding a thymidine kinase contained in the expression vector is induced in the presence of the mutagenic nucleoside, the cells undergo cell death. On the other hand, when the expression of the gene is not induced, the cells survive. Through the utilization of such cell death of the thymidine kinase-deficient cells due to the expression of the gene encoding a thymidine kinase, i.e., the survival of the cells due to the non-expression of the gene, it is possible to conduct the selection of a genetic switch or genetic circuit placed so as to control the expression of the gene encoding a thymidine kinase (OFF selection).

The expression vector containing an expression sequence for a gene encoding a thymidine kinase is preferably an expression vector harboring at least: (a) a gene sequence encoding a thymidine kinase; and (b) a promoter sequence operably linked to the gene sequence according to the item (a) upstream of the gene sequence. Further, the expression vector containing a genetic switch or a genetic circuit is preferably an expression vector harboring at least: (c) another promoter sequence different from the promoter sequence according to the item (b), the another promoter sequence being operably linked to a genetic switch expression sequence downstream thereof; (d) the genetic switch expression sequence; (e) a target sequence of a genetic switch encoded by the genetic switch expression sequence; and (f) a gene sequence having the target sequence operably linked thereto, the gene sequence encoding a transcription regulatory factor that operates on the promoter sequence according to the item (b).

More specifically, in the present invention, there may be employed, for the OFF selection, a selection method for a genetic switch and a genetic circuit, including: incubating thymidine kinase-deficient cells transfected with an expression vector harboring at least sequences according to the following items (a) and (b):

(a) a gene sequence encoding a thymidine kinase; and (b) a promoter sequence operably linked to the gene sequence according to the item (a) upstream of the gene sequence, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a transcription regulatory factor that operates on the promoter sequence according to the item (b), with the addition of a mutagenic nucleoside in the presence of a compound that activates the genetic switch, and collecting viable cells after the incubation, to thereby obtain cells containing a genetic switch and genetic circuit that do not express the gene sequence downstream thereof.

In the present invention, the ON selection and the OFF selection both show extremely high selection efficiency in the selection of genetic switches and genetic circuits. The ON selection and the OFF selection may each be conducted alone. Further, the ON selection and the OFF selection may be conducted in combination. That is, genetic switches and genetic circuits selected by the OFF selection may be further subjected to the ON selection. Further, in the reversed order, genetic switches and genetic circuits selected by the ON selection may be further subjected to the OFF selection. In order to obtain genetic switches with desired functions, it is preferred to conduct the two operations of the ON selection and the OFF selection successively, and it is more preferred to conduct such two successive operations a plurality of times.

In the selection method for a genetic switch and a genetic circuit according to the present invention, the ON selection and the OFF selection can be successively conducted through the use of cells transfected with an expression vector carrying both of an ON-selector and an OFF-selector.

That is, an aspect of the present invention relates to a selection method for a genetic switch and a genetic circuit, including: using cells transfected with an expression vector harboring at least sequences according to the following items (a) and (b):

(a) a gene sequence encoding an alkylated DNA repair enzyme and a gene sequence encoding a thymidine kinase; and (b) a promoter sequence operably linked to the two gene sequences according to the item (a) upstream of the two gene sequences, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a transcription regulatory factor that operates on the promoter sequence according to the item (b); and (1) when the gene sequence encoding a transcription regulatory factor according to the item (f) is a transcription repression factor, in the presence of a compound that activates the genetic switch, incubating the cells with the addition of a mutagenic nucleoside, and collecting viable cells, and in the absence of the compound, adding an alkylating agent to the recovered cells, followed by incubation, and collecting viable cells, or (2) when the gene sequence encoding a transcription regulatory factor according to the item (f) is a transcription activation factor, in the presence of a compound that activates the genetic switch, incubating the cells with the addition of an alkylating agent, and collecting viable cells, and in the absence of the compound, adding a mutagenic nucleoside to the recovered cells, followed by incubation, and collecting viable cells.

A preferred aspect of the present invention relates to a selection method for a genetic switch and a genetic circuit, including: using an alkylating agent-hypersensitive E. coli strain transfected with an expression vector harboring at least sequences according to the following items (a) and (b):

(a) a gene sequence encoding alkyladenine DNA glycosidase (AAG) and a gene sequence encoding a human herpes virus derived thymidine kinase; and (b) a promoter sequence operably linked to the two gene sequences according to the item (a) upstream of the two gene sequences, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a transcription repression factor that operates on the promoter sequence according to the item (b); and in the presence of a compound that activates the genetic switch, incubating the E. coli strain with the addition of 6-(β-D-2-deoxyribo-furanosyl)-3,4-dihydro-8H-pyrimido[4,5-c][1,2]oxazin-7-one (dP), and collecting viable cells, and in the absence of the compound, adding methanesulfonic acid (MMS) to the recovered cells, followed by incubation, and collecting viable cells.

A more preferred aspect of the present invention relates to a selection method for a genetic switch and a genetic circuit, including: using an alkylating agent-hypersensitive E. coli strain transfected with an expression vector harboring at least sequences according to the following items (a) and (b):

(a) a gene sequence encoding alkyladenine DNA glycosidase (AAG) and a gene sequence encoding a human herpes virus derived thymidine kinase; and (b) a promoter sequence operably linked to the two gene sequences according to the item (a) upstream of the two gene sequences, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a CI protein that operates on the promoter sequence according to the item (b); and in the presence of a compound that activates the genetic switch, incubating the E. coli strain for 5 minutes to 60 minutes with the addition of 6-(β-D-2-deoxyribo-furanosyl)-3,4-dihydro-8H-pyrimido[4,5-c][1,2]oxazin-7-one (dP), and collecting viable cells, and then, in the absence of the compound, incubating the cells for 15 minutes to 60 minutes with the addition of methanesulfonic acid (MMS), and collecting viable cells.

Another preferred aspect of the present invention relates to a selection method for a genetic switch and a genetic circuit, including: using an alkylating agent-hypersensitive E. coli strain transfected with an expression vector harboring at least sequences according to the following items (a) and (b):

(a) a gene sequence encoding alkyladenine DNA glycosidase (AAG), a gene sequence encoding a human herpes virus derived thymidine kinase, and a gene sequence encoding AP endonuclease (APE1); and (b) a promoter sequence operably linked to the three gene sequences according to the item (a) upstream of the three gene sequences, and an expression vector harboring at least sequences according to the following items (c) to (f):

(c) another promoter sequence different from the promoter sequence, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a transcription regulatory factor that operates on the promoter sequence according to the item (b); and (1) when the gene sequence encoding a transcription regulatory factor according to the item (f) is a transcription repression factor, in the presence of a compound that activates the genetic switch, incubating the E. coli strain with the addition of 6-(β-D-2-deoxyribo-furanosyl)-3,4-dihydro-8H-pyrimido[4,5-c][1,2]oxazin-7-one (dP), and collecting viable cells, and in the absence of the compound, adding methanesulfonic acid (MMS) to the recovered cells, followed by incubation, and collecting viable cells, or (2) when the gene sequence encoding a transcription regulatory factor according to the item (f) is a transcription activation factor, in the presence of a compound that activates the genetic switch, incubating the *E. coli* strain with the addition of MMS, and collecting viable cells, and in the absence of the compound, adding dP to the recovered cells, followed by incubation, and collecting viable cells.

A preferred aspect of the present invention relates to a selection method for a genetic switch and a genetic circuit, including: using an alkylating agent-hypersensitive *E. coli* strain transfected with an expression vector harboring at least sequences according to the following items (a) and (b):
(a) a gene sequence encoding alkyladenine DNA glycosidase (AAG), a gene sequence encoding a human herpes virus derived thymidine kinase, and a gene sequence encoding AP endonuclease (APE1); and
(b) a promoter sequence operably linked to the three gene sequences according to the item (a) upstream of the three gene sequences, and an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription repression factor that operates on the promoter sequence according to the item (b); and in the presence of a compound that activates the genetic switch, incubating the *E. coli* strain with the addition of deoxyribo-(β-3,4-dihydro-8H-pyrimido[4,5-c][1,2]oxazin-7-one (dP), and collecting viable cells, and in the absence of the compound, incubating the cells with the addition of methanesulfonic acid (MMS), and collecting viable cells.

A more preferred aspect of the present invention relates to a selection method for a genetic switch and a genetic circuit, including: using an alkylating agent-hypersensitive *E. coli* strain transfected with an expression vector harboring at least sequences according to the following items (a) and (b):
(a) a gene sequence encoding alkyladenine DNA glycosidase (AAG), a gene sequence encoding a human herpes virus derived thymidine kinase, and a gene sequence encoding AP endonuclease (APE1); and
(b) a promoter sequence operably linked to the three gene sequences according to the item (a) upstream of the three gene sequences, and an expression vector harboring at least sequences according to the following items (c) to (f):
(c) another promoter sequence different from the promoter sequence, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a CI protein that operates on the promoter sequence according to the item (b); and in the presence of a compound that activates the genetic switch, incubating the *E. coli* strain for 5 minutes to 60 minutes with the addition of 6-(β-D-2-deoxyribo-furanosyl)-3,4-dihydro-8H-pyrimido[4,5-c][1,2]oxazin-7-one (dP), and collecting viable cells, and then, in the absence of the compound, incubating the cells for 15 minutes to 30 minutes with the addition of methanesulfonic acid (MMS), and collecting viable cells.

Further, in the selection method for a genetic switch and a genetic circuit according to the present invention, the ON selection and the OFF selection can be successively conducted through the use of cells transfected with both of an expression vector carrying an ON-selector and an expression vector carrying an OFF-selector.

That is, an aspect of the present invention relates to a selection method for a genetic switch and a genetic circuit, including: using cells transfected with an expression vector harboring at least sequences according to the following items (a-1) and (b-1):
(a-1) a gene sequence encoding an alkylated DNA repair enzyme; and
(b-1) a promoter sequence operably linked to the gene sequence according to the item (a-1) upstream of the gene sequence, an expression vector harboring at least sequences according to the following items (a-2) and (b-2):
(a-2) a gene sequence encoding a thymidine kinase; and
(b-2) a promoter sequence operably linked to the gene sequence according to the item (a-2) upstream of the gene sequence, and an expression vector harboring at least sequences according to the following items (c) to (f):
(c) another promoter sequence different from the promoter sequences, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription regulatory factor that operates on the promoter sequence according to the item (b); and (1) when the gene sequence encoding a transcription regulatory factor according to the item (f) is a transcription repression factor, in the presence of a compound that activates the genetic switch, incubating the cells with the addition of a mutagenic nucleoside, and collecting viable cells, and in the absence of the compound, adding an alkylating agent to the recovered cells, followed by incubation, and collecting viable cells, or
(2) when the gene sequence encoding a transcription regulatory factor according to the item (f) is a transcription activation factor, in the presence of a compound that activates the genetic switch, incubating the cells with the addition of an alkylating agent, and collecting viable cells, and in the absence of the compound, adding a mutagenic nucleoside to the recovered cells, followed by incubation, and collecting viable cells.

A preferred aspect of the present invention relates to a selection method for a genetic switch and a genetic circuit, including: using an alkylating agent-hypersensitive *E. coli* strain transfected with an expression vector harboring at least sequences according to the following items (a-1) and (b-1):
(a-1) a gene sequence encoding alkyladenine DNA glycosidase (AAG); and
(b-1) a promoter sequence operably linked to the gene sequence according to the item (a-1) upstream of the gene sequence, an expression vector harboring at least sequences according to the following items (a-2) and(b-2):
(a-2) a gene sequence encoding a human herpes virus derived thymidine kinase; and
(b-2) a promoter sequence operably linked to the gene sequence according to the item (a-2) upstream of the gene sequence, and
an expression vector harboring at least sequences according to the following items (c) to (f):
(c) another promoter sequence different from the promoter sequences, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription repression factor that operates on the promoter sequence according to the item (b); and
in the presence of a compound that activates the genetic switch, incubating the E. coli strain with the addition of 6-(β-D-2-deoxyribo-furanosyl)-3,4-dihydro-8H-pyrimido [4,5-c][1,2]oxazin-7-one (dP), and collecting viable cells, and in the absence of the compound, adding methanesulfonic acid (MMS) to the recovered cells, followed by incubation, and collecting viable cells.

A more preferred aspect of the present invention relates to a selection method for a genetic switch and a genetic circuit, including: using an alkylating agent-hypersensitive E. coli strain transfected with
an expression vector harboring at least sequences according to the following items (a-1) and (b-1):
(a-1) a gene sequence encoding alkyladenine DNA glycosidase (AAG); and
(b-1) a promoter sequence operably linked to the gene sequence according to the item (a-1) upstream of the gene sequence,
an expression vector harboring at least sequences according to the following items (a-2) and (b-2):
(a-2) a gene sequence encoding a human herpes virus derived thymidine kinase; and
(b-2) a promoter sequence operably linked to the gene sequence according to the item (a-2) upstream of the gene sequence, and
an expression vector harboring at least sequences according to the following items (c) to (f):
(c) another promoter sequence different from the promoter sequences, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a CI protein that operates on the promoter sequence according to the item (b); and in the presence of a compound that activates the genetic switch, incubating the E. coli strain for 5 minutes to 60 minutes with the addition of 6-(β-D-2-deoxyribo-furanosyl)-3,4-dihydro-8H-pyrimido[4,5-c][1,2] oxazin-7-one (dP), and collecting viable cells, and then, in the absence of the compound, adding methanesulfonic acid (MMS) to the recovered cells, followed by incubation for 15 minutes to 60 minutes, and recovering living cells.

Another aspect of the present invention relates to a selection method for a genetic switch and a genetic circuit, including: using an alkylating agent-hypersensitive E. coli strain transfected with
an expression vector harboring at least sequences according to the following items (a-1) and (b-1):
(a-1) a gene sequence encoding alkyladenine DNA glycosidase (AAG) and a gene sequence encoding AP endonuclease (APE1); and
(b-1) a promoter sequence operably linked to the two gene sequences according to the item (a-1) upstream of the two gene sequences,
an expression vector harboring at least sequences according to the following items (a-2) and (b-2):
(a-2) a gene sequence encoding a human herpes virus derived thymidine kinase; and
(b-2) a promoter sequence operably linked to the gene sequence according to the item (a-2) upstream of the gene sequence, and
an expression vector harboring at least sequences according to the following items (c) to (f):
(c) another promoter sequence different from the promoter sequences, the another promoter sequence being operably linked to a genetic switch expression sequence downstream thereof;
(d) the genetic switch expression sequence;
(e) a target sequence of a genetic switch encoded by the genetic switch expression sequence; and
(f) a gene sequence having the target sequence operably linked thereto, the gene sequence encoding a transcription regulatory factor that operates on the promoter sequence according to the item (b); and
(1) when the gene sequence encoding a transcription regulatory factor according to the item (f) is a transcription repression factor, in the presence of a compound that activates the genetic switch, incubating the E. coli strain with the addition of 6-(β-D-2-deoxyribo-furanosyl)-3,4-dihydro-8H-pyrimido[4,5-c][1,2]oxazin-7-one (dP), and collecting viable cells, and in the absence of the compound, adding methanesulfonic acid (MMS) to the recovered cells, followed by incubation, and collecting viable cells, or
(2) when the gene sequence encoding a transcription regulatory factor according to the item (f) is a transcription activation factor, in the presence of a compound that activates the genetic switch, incubating the E. coli strain with the addition of MMS, and collecting viable cells, and in the absence of the compound, adding dP to the recovered cells, followed by incubation, and collecting viable cells.

A preferred aspect of the present invention relates to a selection method for a genetic switch and a genetic circuit, including: using an alkylating agent-hypersensitive E. coli strain transfected with
an expression vector harboring at least sequences according to the following items (a-1) and (b-1):
(a-1) a gene sequence encoding alkyladenine DNA glycosidase (AAG) and a gene sequence encoding AP endonuclease (APE1); and
(b-1) a promoter sequence operably linked to the two gene sequences according to the item (a-1) upstream of the two gene sequences,
an expression vector harboring at least sequences according to the following items (a-2) and (b-2):
(a-2) a gene sequence encoding a human herpes virus derived thymidine kinase; and (b-2) a promoter sequence operably linked to the gene sequence according to the item (a-2) upstream of the gene sequence, and an expression vector harboring at least sequences according to the following items (c) to (f):

(c) another promoter sequence different from the promoter sequences, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a transcription repression factor that operates on the promoter sequence according to the item (b); and in the presence of a compound that activates the genetic switch, incubating the *E. coli* strain with the addition of 6-(β-D-2-deoxyribo-furanosyl)-3,4-dihydro-8H-pyrimido[4,5-c][1,2]oxazin-7-one (dP), and collecting viable cells, and in the absence of the compound, adding methanesulfonic acid (MMS) to the recovered cells, followed by incubation, and collecting viable cells.

A more preferred aspect of the present invention relates to a selection method for a genetic switch and a genetic circuit, including: using an alkylating agent-hypersensitive *E. coli* strain transfected with an expression vector harboring at least sequences according to the following items (a-1) and (b-1):

(a-1) a gene sequence encoding alkyladenine DNA glycosidase (AAG) and a gene sequence encoding AP endonuclease (APE1); and (b-1) a promoter sequence operably linked to the two gene sequences according to the item (a-1) upstream of the two gene sequences, an expression vector harboring at least sequences according to the following items (a-2) and (b-2):

(a-2) a gene sequence encoding a human herpes virus derived thymidine kinase; and (b-2) a promoter sequence operably linked to the gene sequence according to the item (a-2) upstream of the gene sequence, and an expression vector harboring at least sequences according to the following items (c) to (f):

(c) another promoter sequence different from the promoter sequences, the another promoter sequence being operably linked to a genetic switch expression sequence downstream thereof;

(d) the genetic switch expression sequence;

(e) a target sequence of a genetic switch encoded by the genetic switch expression sequence; and (f) a gene sequence having the target sequence operably linked thereto, the gene sequence encoding a CI protein that operates on the promoter sequence according to the item (b); and in the presence of a compound that activates the genetic switch, incubating the *E. coli* strain for 5 minutes to 60 minutes with the addition of 6-(β-D-2-deoxyribo-furanosyl)-3,4-dihydro-8H-pyrimido[4,5-c][1,2]oxazin-7-one (dP), and collecting viable cells, and then, in the absence of the compound, adding methanesulfonic acid (MMS) to the recovered cells, followed by incubation for 15 minutes to 60 minutes, and collecting viable cells.

The present invention also relates to an expression vector to be used as a selector in the selection method for a genetic switch and a genetic circuit according to the present invention. The expression vector to be used as a selector in the present invention contains at least a gene sequence encoding an alkylated DNA repair enzyme and a promoter sequence operably linked to the gene sequence. As a preferred example thereof, there may be given an expression vector containing at least a gene sequence encoding an alkylated DNA repair enzyme and a gene sequence encoding a thymidine kinase, and a promoter sequence operably linked to these two gene sequences upstream of the two gene sequences. As a more preferred example thereof, there may be given an expression vector containing the above-mentioned sequences and further containing a gene sequence encoding AP endonuclease (APE1) placed downstream of the gene sequence encoding an alkylated DNA correction enzyme.

More specifically, the expression vector to be used as a selector in the present invention contains at least a gene sequence encoding alkyladenine DNA glycosidase (AAG) and a promoter sequence operably linked to the gene sequence. As a preferred example thereof, there may be given an expression vector containing at least a gene sequence encoding AAG and a gene sequence encoding a human herpes virus derived thymidine kinase, and a promoter sequence operably linked to these two gene sequences upstream of the two gene sequences. As a more preferred example thereof, there may be given an expression vector containing the above-mentioned sequences and further containing a gene sequence encoding AP endonuclease (APE1) placed downstream of the gene sequence encoding an alkylated DNA correction enzyme.

As a more specific example of the expression vector to be used as a selector in the present invention, there may be given expression vector DNA represented by each of base sequences set forth in SEQ ID NOS: 1 to 6 of the sequence listing. The expression vector DNA represented by the base sequence set forth in SEQ ID NO: 1 is expression vector DNA (referred to as Ver. 1) containing an alkyladenine DNA glycosidase (AAG) gene and a human herpes virus thymidine kinase (hsvTK) gene. The expression vector DNA represented by the base sequence set forth in SEQ ID NO: 2 is expression vector DNA (referred to as Ver. 2) containing an alkyladenine DNA glycosidase (AAG) gene, a human herpes virus thymidine kinase (hsvTK) gene, and AP endonuclease (APE1). The expression vector DNA represented by the base sequence set forth in SEQ ID NO: 3 is expression vector DNA (referred to as Ver. 2.1) containing an alkyladenine DNA glycosidase variant (AAG (L180F)) gene, a human herpes virus thymidine kinase (hsvTK) gene, and AP endonuclease (APE1). The expression vector DNA represented by the base sequence set forth in SEQ ID NO: 4 is expression vector DNA (referred to as Ver. 3) containing an alkyladenine DNA glycosidase (AAG) gene, a human herpes virus thymidine kinase (hsvTK) gene, and AP endonuclease (APE1). The expression vector DNA represented by the base sequence set forth in SEQ ID NO: 5 is expression vector DNA containing an alkyladenine DNA glycosidase (AAG) gene. The expression vector DNA represented by the base sequence set forth in SEQ ID NO: 6 is expression vector DNA containing an alkyladenine DNA glycosidase (AAG) gene and AP endonuclease (APE1). The expression vector DNA represented by each of the base sequences set forth in SEQ ID NOS: 1 to 4 can be used as a dual selector, and hence is preferably used in the present invention. Of those, the expression vector DNA represented by the base sequence set forth in SEQ ID NO: 3 is particularly preferably used because it contains an AAG variant gene obtained as a variant having resistance against methanesulfonic acid as an alkylating agent.

A library of genetic switches that may be subjected to the selection method for a genetic switch and a genetic circuit can be prepared by an already established known random mutagenesis method such as an error-prone polymerase chain reaction (Error-Prone PCR, Leung, D W, et al., A method for random mutagenesis of a defined DNA segment using a modified polymerase chain reaction. Techniques, 1, 11-5 (1989)), a saturation mutagenesis method (Miyazaki, K, et al., Exploring nonnatural evolutionary pathways by saturation mutagenesis: Rapid improvement of protein function. J. Mol. Evol., 49, 716-20 (1999).), or DNA shuffling (DNA shuffling, Stemmer, W P C., Rapid evolution of a protein in-vitro by DNA shuffling. Nature, 370, 389-91 (1994)).

The selection method for a genetic switch and a genetic circuit according to the present invention has a feature of the rapidity of a selection operation, which is an element required of a circuit selector. Specifically, in each of the ON selection and the OFF selection, the action time can be shortened to about 5 minutes to 60 minutes (see Example 3 and Experimental Example 3). The reason why is that the method of the present invention is not a method involving using the induction of "growth inhibition" of cells as a selection indicator like a conventional selection method, but is a method involving using irreversible cell death as a selection indicator, and does not require the time required for the proliferation of cells. In actuality, a selection method based on a difference in growth rate or a difference in Mobility between cells (Non Patent Literatures 6, 7, 10 to 12, and 13) requires an overnight period for one operation of each of ON selection and OFF selection. The shortening of the selection operation time is an extremely desirable feature for circuit selection involving repeating ON selection and OFF selection a plurality of times. Particularly when the purpose is to, for example, develop an oscillation circuit, a switch with a short switching time (short latency), or the like, a selection approach with high rapidity like the method according to the present invention is essential.

The selection method for a genetic switch and a genetic circuit according to the present invention has a feature of high selection efficiency, which is another element required of circuit selection. In actuality, when cells transfected with selector plasmid Ver. 2 (pCI-aag-hsvTK-ape1) were used, and subjected to OFF selection through treatment with dP for 1 hour, followed by ON selection through treatment with MMS for 30 minutes, the single round of dual selection was able to enrich cells having a desired genetic circuit 40-fold to 166-fold (see Example 5). Further, when cells transfected with selector plasmid Ver. 2.1 (pCI-aag (L180F)-hsvTK-ape1) were used, and subjected to OFF selection through treatment with dP for 1 hour, followed by ON selection through treatment with MMS for 30 minutes, the single round of dual selection was able to enrich cells having a desired genetic circuit 409-fold to 1,935-fold (see Example 5). As described above, through the dual selection as a combination of ON selection and OFF selection according to the present invention, it is possible to conduct the selection of a genetic switch and a genetic circuit with extremely high efficiency.

In addition, by the selection method for a genetic switch and a genetic circuit according to the present invention, it is possible to conduct the selection of a genetic switch and a genetic circuit within an extremely short time period, and hence it is possible to conduct functional selection or selection along time course with respect to expression timing. For example, selection with respect to the switching time (latency) of a genetic switch can be conducted. In actuality, when cells transfected with selector plasmid Ver. 2.1 (pCI-aag (L180F)-hsvTK-ape1) were used, precultured in medium containing AHL, then cultured in medium containing no AHL, and subsequently subjected to ON selection, it was possible to select a genetic circuit capable of expressing a C-terminal truncated variant of CI (hereinafter referred to as "CItruc") from a cell population obtained by mixing cells harboring a genetic circuit capable of expressing full-length CI and cells harboring the genetic circuit capable of expressing CItruc (see Example 6). As described above, the tuning of a genetic circuit also becomes possible by repeating ON selection and OFF selection along time course in multiple stages by the method according to the present invention.

The selection method for a genetic switch and a genetic circuit according to the present invention can be employed for, for example, the selection and development of a genetic switch for mass production of a useful protein, a genetic switch as a tool for metabolic engineering, and a genetic switch mechanism as a biosensor. Further, the method of the present invention is a selection method based on informational death (error catastrophe) of cells due to accumulation of random mutations, in which an attack is not directed at a certain biochemical action but is directed at all sites of cell functions, and hence resistance acquisition (adaptation by the cells) is extremely unlikely to occur. Therefore, a robust selection platform can be provided.

EXAMPLES

The present invention is hereinafter more specifically described by way of Examples. Before Examples are shown, a selection method for a genetic switch and a genetic circuit involving using a human herpes virus derived thymidine kinase (hsvTK) as a selector, which has already been developed by the inventors of the present invention and is utilized in the present invention, is shown in Experimental Examples 1 to 7. The present invention is by no means limited by Examples and Experimental Examples shown below.

First, materials and methods used in Examples and Experimental Examples below are briefly described.

6-($\beta$-D-2-Deoxyribo-furanosyl)-3,4-dihydro-8H-pyrimido[4,5-c][1,2]oxazin-7-one (dP) and 5-fluoro-2'-deoxyuridine (5FdU) were purchased from Berry & Associates (MI) and Sigma & Aldrich, respectively. Oligonucleotides used were synthesized by FASMAC Co., Ltd.

An *E. coli* JW1226 strain as a thymidine kinase-deficient *E. coli* strain was obtained from KEIO collection (Baba, T, et al., Construction of *Escherichia coli* K-12 in-frame, single-gene knockout mutants: the Keio collection. Mol Syst Biol, 2, 2006 0008 (2006)). Unless otherwise noted, LB medium containing 2% (w/v) LB Broth Base (manufactured by Invitrogen) was used as culture medium. Cells were proliferated in a glass test tube at 37° C.

Unless otherwise noted, an alkylating agent-sensitive *E. coli* strain MV2157 (alkyladenine repair system-deficient strain (alkA, tag-deficient strain: thr-1 leuB6 proA2 his4 thi1argE3 lacY1 galK2 rpsL supE44 ara-14 xyl-15 mtl-1 txs-33 alkA1 tag-1)) was cultured in LB medium or on LB solid medium at 37° C.

An hsvTK expression vector pPL-hsvtk and a GFPuv expression vector pPL-gfpuv were prepared by fusing the respective reading frames from pET-hsvtk (Black, M E, et al., Creation of drug-specific herpes simplex virus type 1 thymidine kinase mutants for gene therapy. Proc Natl Acad Sci USA, 93, 3525-9 (1996)) or pGFPuv (manufactured by Clontech Laboratories, Inc.) downstream of a PL promoter to transfect a pACYC 184-based plasmid.

Four model genetic circuits were prepared (FIG. 1). Circuit-A and Circuit-B are each a circuit into which N-acyl-L-homoserine lactone (AHL) is inputted and which outputs a repressor protein CI as a result. The CI protein is a transcription repression factor, and represses protein expression under a PR promoter or a PL promoter. Therefore, such circuit expresses the CI protein when its output state is ON, and strongly represses gene expression under control of a PR promoter or a PL promoter in cells. Circuit-A constitutively expresses AHL receptor protein LuxR by a Trc promoter, and expresses the CI protein placed downstream of a Lux promoter depending on the concentration of AHL. Circuit-B constitutively expresses AHL receptor protein LuxR by a Trc promoter, and expresses CItruc placed downstream of a Lux promoter depending on the concentration of AHL. The CItruc is a C-terminal truncated CI protein, and has a decreased ability to bind to a target sequence, resulting in a decreased ability to repress transcription. In those circuits, the LuxR and Lux promoter are directed in the same direction, and a strong transcription terminator is present therebetween. Circuit-C is obtained by removing the ribosome binding site (RBS) of the CI protein from Circuit-B, and the translation efficiency of the CI protein is lost. Thus, Circuit-C does not express the CI protein irrespective of the concentration of AHL. On the other hand, Circuit-D is obtained by removing the transcription terminator downstream of LuxR from Circuit-B, and constantly expresses a CI gene by read-through of the Trc promoter at the uppermost stream. Thus, Circuit-D always expresses the CI protein irrespective of the concentration of AHL.

A plasmid map of Circuit-A is illustrated in FIG. 2-A, and its nucleic acid sequence is set forth in SEQ ID NO: 9. Circuit-A is based on pLux-CI-gfp and prepared by removing the gfp gene by PCR and inserting a CI gene through utilization of a blunt end. Circuit-A always expresses LuxR owing to leaky expression of pTrc, and expresses the CI protein in response to AHL. Circuit-A represses gene expression downstream of the PR promoter, and hence works as an inverter circuit with respect to the input of AHL.

A plasmid map of Circuit-B is illustrated in FIG. 2-B, and its nucleic acid sequence is set forth in SEQ ID NO: 10. Circuit-B is based on pLux-CI-gfp and prepared by removing the gfp gene by PCR and inserting a gene for CItruc through the utilization of a HindIII site present in the CI gene and a HindIII site present downstream thereof. Circuit-B always expresses LuxR owing to leaky expression of Trc, and expresses CItruc in response to AHL. Circuit-B represses gene expression downstream of the PR promoter, and hence works as an inverter circuit with respect to the input of AHL. CItruc has its C-terminus truncated, and hence has a low repressor activity and is unstable as compared to the full-length CI protein.

A plasmid map of Circuit-C is illustrated in FIG. 2-C, and its sequence is set forth in SEQ ID NO: 11. Circuit-C is based on the DNA of Circuit-B and was prepared by conducting PCR so as to remove RBS in front of the CI gene and ligating the products through the use of an NcoI site. Circuit-C lacks RBS upstream of the CI gene, and hence the CI protein is not translated, thus being not expressed. Circuit-C is used as an ON circuit.

A plasmid map of Circuit-D is illustrated in FIG. 2-D, and its sequence is set forth in SEQ ID NO: 12. Circuit-D is based on the DNA of Circuit-B and was prepared by conducting PCR so as to remove the terminator sequence and the Lux promoter upstream of the CI gene and ligating the products through the use of an EcoRI site. Circuit-D lacks the terminator sequence and the Lux promoter sequence upstream of the CI gene, and hence always expresses CItruc owing to read-through from the trc promoter. Circuit-D is used as an OFF circuit.

Experimental Example 1

An OFF selection method for a genetic switch and a genetic circuit was established.

First, with the use of mutation frequency in a low-concentration dP medium as an indicator, TK, thymidine monophosphate kinase (Tmk), and nucleoside diphosphate kinase (Ndk) were overexpressed. As a result, it was found that, as with other nucleoside analogs, the rate-limiting step of the incorporation of dP into DNA was the first phosphorylation catalyzed by TK (unpublished data). Next, some tk genes of different origins were tested. As a result, hsvTK showed the highest dP incorporation efficiency.

Figure 3:
[FIG. 3] A schematic diagram illustrating the gene structure of pTrc-hsvtk used for constantly expressing a human herpes virus derived thymidine kinase (hsvTK) (Experimental Example 1 and Experimental Example 3).

With the TK-deficient *E. coli* strain JW1226, human herpes virus derived thymidine kinase (hsvTK) was expressed by transfecting pTrc-hsvtk (FIG. 3), and a relationship between the concentration of dP and the survival rate of cells (viable cell count) was investigated.

First, JW1226 cells transfected with pTrc-hsvtk were cultured in 2 mL of LB medium containing 100 µg/mL of ampicillin at 37° C. overnight. Next, the culture was diluted with 1 mL of fresh LB medium containing dP (at a final concentration of 0 to 100 nM) 1,000-fold ($10^6$ cells/mL), and stirred and shaken at 37° C. for 12 hours. After the culture, the cells were seeded on an LB-agar (1.5% w/v) plate containing ampicillin at 100 µg/mL. After incubation at 37° C. for 12 hours, the number of colonies grown was counted as a viable cell count.

Figure 4:
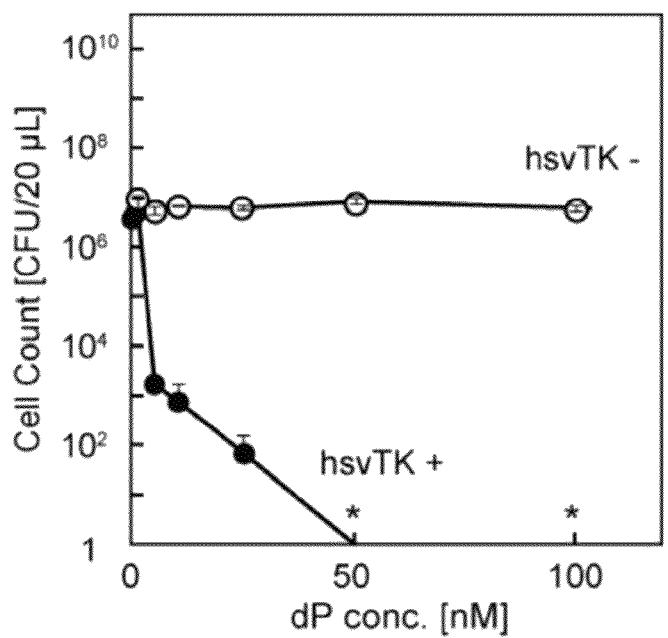
[FIG. 4] A graph showing that a thymidine kinase (TK)-deficient strain of $E.$ $coli$ grows even in the presence of dP but the expression of hsvTK remarkably decreases the survival rate of the strain. In the figure, "●" represents a TK-deficient $E.$ $coli$ strain in which hsvTK is expressed (hsvTK+), and "○" represents a TK-deficient $E.$ $coli$ strain in which hsvTK is not expressed (hsvTK−). In the figure, the vertical axis represents a viable cell count (Cell Count), and the horizontal axis represents the concentration of dP (dP conc.) (Experimental Example 1).

In the TK-deficient *E. coli* strain in which hsvTK was expressed (hsvTK+), the viable cell count of the cells significantly decreased in a dP concentration-dependent manner (FIG. 4). On the other hand, in the TK-deficient *E. coli* strain transfected with a control plasmid (pTrc99A: vector obtained by removing the structural gene of hsvTK) in place of hsvTK (hsvTK−), no reduction in survival rate was found under all the selection conditions tested.

Thus, it was revealed that the addition of dP at very low concentrations (10 to 100 nM) in the culture of hsvTK+ was able to selectively kill only cells expressing hsvTK.

Through the utilization of the change in the survival rate of a TK-deficient cell strain in the presence of dP depending on the presence or absence of the expression of hsvTK, it is possible to conduct functional selection of a genetic switch or genetic circuit set so as to control an hsvtk gene-expressing circuit. That is, when a genetic switch or a genetic circuit does not operate and the hsvtk gene downstream thereof is not expressed, the survival rate of a TK-deficient cell strain in the presence of dP increases. Therefore, through the selection of a TK-deficient cell strain having a high survival rate in the presence of dP, it is possible to select a genetic switch or genetic circuit in an OFF state, which does not express the hsvtk gene.

Thus, an excellent selection approach involving picking up only a genetic switch/circuit in an OFF state was able to be established.

Experimental Example 2

An ON selection method for a genetic switch and a genetic circuit was established.

With the TK-deficient strain of *E. coli* JW1226, a human herpes virus derived thymidine kinase (hsvTK) was expressed by transfecting pTrc-hsvtk (FIG. 3), and a relationship between the concentration of 5FdU and the survival rate of cells (viable cell count) was investigated.

First, JW1226 cells transfected with pTrc-hsvtk were diluted with 1 mL of positive selection medium so as to achieve an OD600 of 0.002 (approximately $10^6$ cells/mL), and cultured at 37° C. for 12 hours while being rotated at 200 rpm. The positive selection medium used was medium containing tryptone at 2% w/v, NaCl at 0.5% w/v, dT at 10 µg/mL, adenosine at 1 µg/mL, and 5FdU at 0 to 25 µg/mL. After the culture, a portion of the resultant culture was collected and inoculated in an LB plate containing ampicillin, and the number of colonies grown was counted as a viable cell count.

Figure 5:
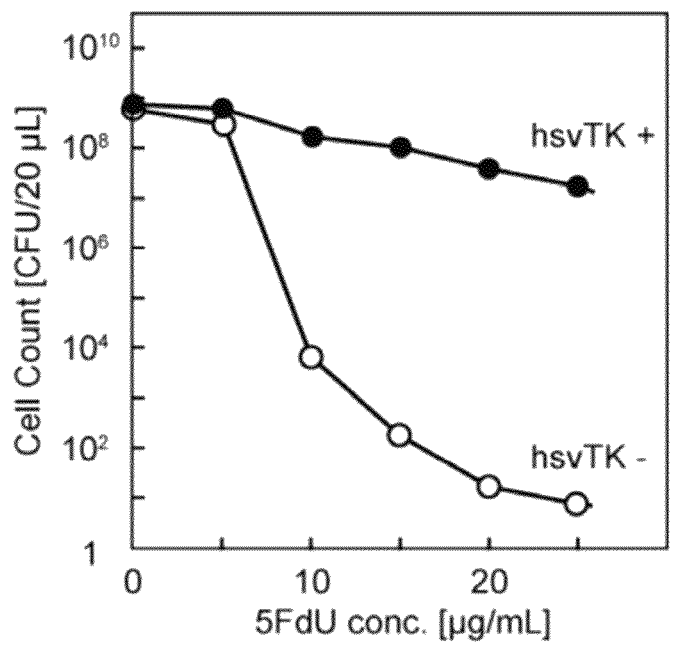
[FIG. 5] A graph showing that the survival rate of the TK-deficient $E.$ $coli$ strain decreases in a 5FdU concentration-dependent manner but the expression of hsvTK represses the decrease in the survival rate. In the figure, "●" represents a TK-deficient $E.$ $coli$ strain in which hsvTK is expressed (hsvTK+), and "○" represents a TK-deficient $E.$ $coli$ strain in which hsvTK is not expressed (hsvTK−). In the figure, the vertical axis represents a viable cell count (Cell Count), and the horizontal axis represents the concentration of 5FdU (5FdU conc.) (Experimental Example 2).

In the TK-deficient *E. coli* strain in which hsvTK was not expressed (hsvTK−), the viable cell count decreased with increasing concentrations of 5FdU (FIG. 5). On the other hand, in the TK-deficient *E. coli* strain in which hsvTK was expressed (hsvTK+), the viable cell count decreased at a slow rate as compared to hsvTK−. When the concentration of 5FdU was 25 µg/mL, hsvTK+ showed a $4.8 \times 10^7$-fold survival rate as compared to hsvTK−.

Thus, it was confirmed that the survival rate of a TK-deficient *E. coli* strain in the presence of 5FdU remarkably changed depending on the presence or absence of the expression of hsvTK.

Through the utilization of the change in the survival rate of a TK-deficient cell strain in the presence of 5FdU depending on the presence or absence of the expression of hsvTK, it is possible to conduct functional selection of a genetic switch or genetic circuit set so as to control an hsvtk gene-expressing circuit. That is, when a genetic switch or a genetic circuit operates to cause the expression of hsvTK downstream thereof, the survival rate of a TK-deficient cell strain in the presence of 5FdU increases. Therefore, through the selection of a TK-deficient cell strain having a high survival rate in the presence of 5FdU, it is possible to select a genetic switch or genetic circuit in an ON state, which can cause the expression of hsvTK.

Thus, a selection approach involving picking up only a genetic switch and genetic circuit in an ON state through the use of TK-deficient cells transfected with the hsvtk gene was able to be established.

Experimental Example 3

The rapidity of the OFF selection method established in Experimental Example 1 was studied.

First, TK-deficient cells transfected with pTrc-hsvtk (FIG. 3) so as to constantly express hsvTK were cultured under shaking at 37° C. and 200 rpm until an OD of 0.05 (approximately $3 \times 10^7$ cells/mL) was achieved. The resultant was dispensed at 1 mL each, dP was added (final concentration: 1 µM), and culture was continued at 37° C. After a lapse of 5, 30, or 60 minutes, 20 µL of the culture (approximately $10^6$ cells) were collected and inoculated in an LB plate containing ampicillin, and the number of colonies grown was counted as a viable cell count.

Figure 6:
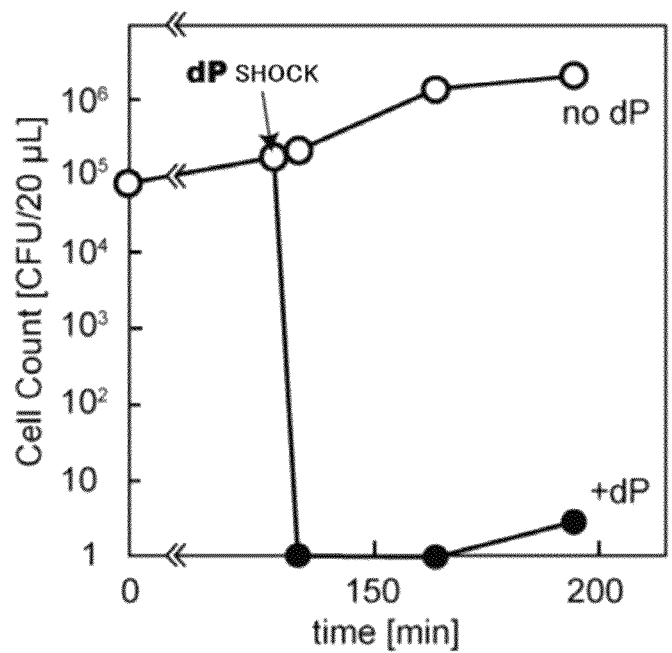
[FIG. 6] A graph showing that, in the TK-deficient $E.$ $coli$ strain in which hsvTK is expressed, the addition of dP (indicated by "dP shock" in the figure) causes cell death within 5 minutes from the addition. In the figure, "●" represents the addition of dP (indicated by "+dP" in the figure), and "○" represents the addition of no dP (indicated by "no dP" in the figure). In the figure, the vertical axis represents a viable cell count (Cell Count), and the horizontal axis represents time (min) (time [min]) (Experimental Example 3).

In the sample to which a dP shock had been applied, the viable cell count was almost zero at any action time (FIG. 6). On the other hand, when the dP shock was not applied, the viable cell count increased. From the results, it was found that the OFF selection was sufficiently completed by an operation within up to 5 minutes.

Experimental Example 4

The efficacy of each of the OFF selection method and ON selection method for a genetic switch and a genetic circuit established in Experimental Examples 1 and 2 was tested by using the model genetic circuits.

Circuits-A to D were each used by being inserted into plasmid pBR322. In order to confirm whether or not Circuits-A to D operated as designed, the plasmids having these circuits were each coexpressed with pPL-gfpuv as a screening plasmid in *E. coli* JW1226 (FIG. 1). PL is a promoter that is repressed by the CI protein, and outputs fluorescence when the expression level of the CI protein is low. That is, when coexisting with Circuit-A or Circuit-B, pPL-gfpuv inverts the AHL input to output fluorescence. Culture was conducted in LB media containing 100 µg/mL of ampicillin and having different concentrations of AHL at 37° C. for 12 hours. The cell densities (OD600=2) of the culture solutions were adjusted to the same value, and fluorescence values in the media with the respective concentrations of AHL were measured (Fluoroskan Ascent (Thermo), excitation filter: 390 nm (half width: 20 nm), fluorescence emission filter: 510 nm (half width: 10 nm)).

Figure 7:
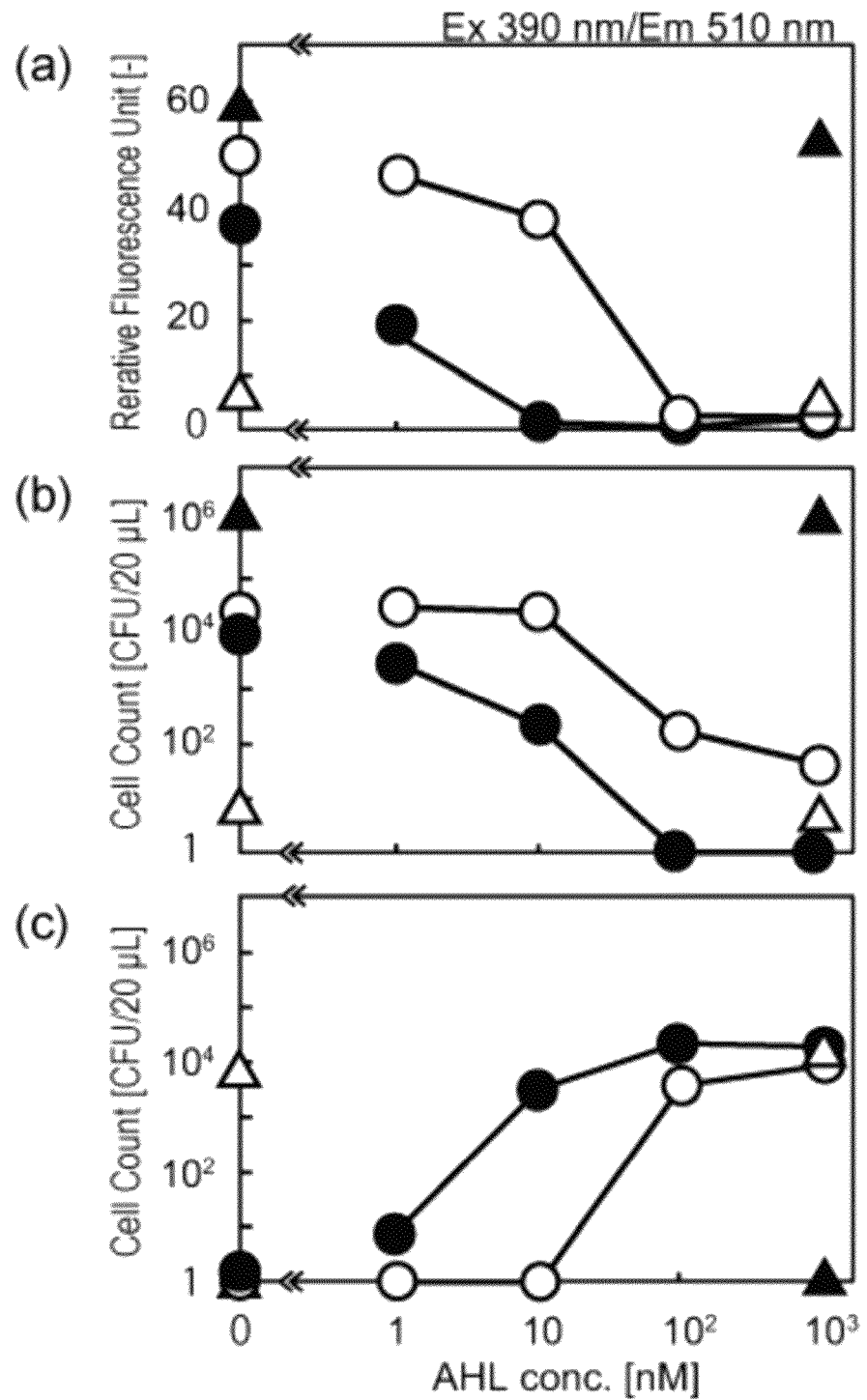
[FIG. 7] Graphs showing the results of the confirmation that the model genetic circuits illustrated in FIG. 1 operate as designed. In the figures, the respective symbols represent the model genetic circuits illustrated in FIG. 1, and "●" represents Circuit-A, "○" represents Circuit-B, "▲" represents Circuit-C, and "△" represents Circuit-D. The panel (a) shows results obtained by measuring the expression of a green fluorescent protein (GFPuv) in the presence of AHL at various concentrations in a TK-deficient $E.$ $coli$ strain in which each of the model genetic circuits and a GFPuv expression plasmid were coexpressed. In the panel (a), the vertical axis represents a relative fluorescence intensity (Relative Fluorescence), and the horizontal axis represents the concentration of AHL (AHL conc.). The panel (b) shows results obtained by conducting ON selection through the addition of 5FdU and measuring viable cell counts in the presence of AHL at various concentrations in the TK-deficient $E.$ $coli$ strain in which each of the genetic circuits and an hsvTK expression plasmid were coexpressed. The panel (c) shows results obtained by conducting OFF selection through the addition of dP and measuring viable cell counts in the presence of AHL at various concentrations in the TK-deficient $E.$ $coli$ strain in which each of the genetic circuits and an hsvTK expression plasmid were coexpressed. In each of the panel (b) and the panel (c), the vertical axis represents a viable cell count (Cell Count), and the horizontal axis represents the concentration of AHL (AHL conc.) (Experimental Example 4).

The panel (a) of FIG. 7 shows the results. The cells having Circuit-C constitutively showed a high fluorescence intensity independent of the concentration of AHL. Further, the cells having Circuit-D always showed a low (background level) fluorescence intensity independent of the concentration of AHL. On the other hand, in the cells transformed with Circuit-A and Circuit-B, the fluorescence intensity of GFPuv decreased in an AHL concentration-dependent manner. This is because, as the concentration of AHL increased, the expression level of the CI protein increased, and the action of the CI protein repressed the expression of the gfpuv gene downstream of the PL promoter. However, the response threshold of the AHL switching was higher in the cells having Circuit-B than in the cells having Circuit-A.

Through the use of those four genetic circuits, the ON selection method established in Experimental Example 2 was tested. Specifically, those four circuits were each cotransfected with hsvTK under control of the PL promoter into the same TK-deficient cells, and were subjected to ON selection in media with different concentrations of AHL.

The panel (b) of FIG. 7 shows the results. In Circuit-A, the survival rate rapidly decreased at AHL concentrations of 10 nM or more. This is due to the following: LuxR that has formed a complex with AHL enhances the expression of the CI protein, resulting in effective repression of the expression of hsvTK by the CI protein, and hence the salvage pathway is not triggered. From the fact that the panel (a) and panel (b) of FIG. 7 show similar patterns, it is found that the survival rate of cells has a 1:1 correspondence to the triggered state of the expression of hsvTK. Circuit-B showed similar results to those of Circuit-A, but the survival rate according to Circuit-B was particularly high in a high AHL concentration region. This is because the C-terminal truncated CI protein has a low ability to repress the expression of hsvTK as compared to the wild-type CI protein. Further, each of Circuit-A and Circuit-B showed an about 100-fold lower survival rate than Circuit-C. This is due to the following: the Lux promoter is leaky, i.e., even when the expression of the CI protein is in an OFF state under high AHL concentration conditions, the Lux promoter causes the CI protein to be expressed at a low level, and thereby the expression partially represses hsvTK downstream of the CI protein.

In addition, through the use of those four genetic circuits, the OFF selection method established in Experimental Example 1 was tested. Specifically, those four circuits were each cotransfected with hsvTK under control of the PL promoter into the same TK-deficient cells, and were subjected to OFF selection in media with different concentrations of AHL.

The panel (c) of FIG. 7 shows the results. For each of Circuit-A and Circuit-B, the viable cell count increased in an AHL concentration-dependent manner. This is due to the following: LuxR that had formed a complex with AHL enhanced the expression of the CI protein, resulting in effective repression of the expression of hsvTK by the CI protein, and hence the incorporation of dP was inhibited and cells were not affected by the presence of dP to survive.

The above-mentioned results revealed that the produced four genetic circuits operated as designed in the OFF selection method and ON selection method established in Experimental Examples 1 and 2.

Experimental Example 5

Figure 8:
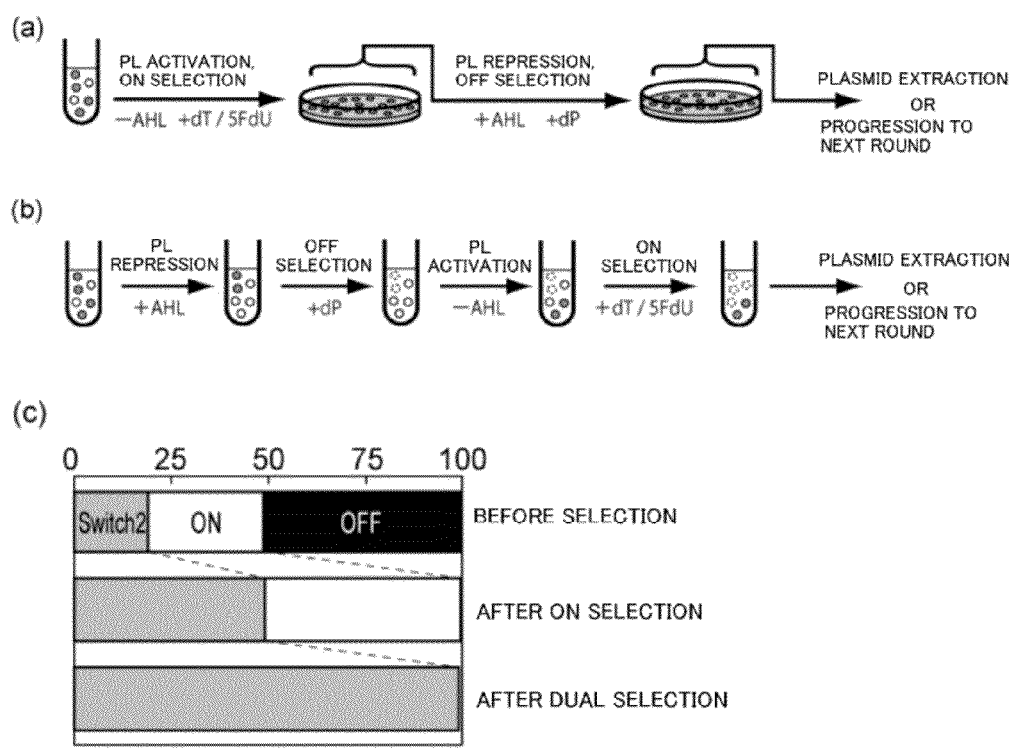
[FIG. 8] Schematic diagrams illustrating the steps of dual selection as a combination of OFF selection and ON selection and showing results thereof. The panel (a) illustrates an outline of a dual selection method involving using agar medium, and the panel (b) illustrates the steps of a dual selection method to be conducted in liquid medium. The panel (c) shows results obtained by subjecting mixed cells obtained by mixing three kinds of TK-deficient $E.$ $coli$ strains having three kinds of genetic circuits, respectively, to dual selection by the method illustrated in the panel (a). Results obtained by measuring the ratios of the respective cells before the dual selection, after the ON selection, and after the dual selection are shown (Experimental Example 5).

The OFF selection method and ON selection method for a genetic switch and a genetic circuit established in Experimental Examples 1 and 2 were employed to study the selection of a desired genetic switch and genetic circuit. ON selection and OFF selection were conducted with solid media. In this study, the OFF selection was successively conducted after the ON selection (dual selection). FIG. 8 illustrates and shows the steps of the dual selection and the results.

Specifically, the conducted study involved mixing Genetic Circuits-B, C, and D produced in Experimental Example 4, and detecting, therefrom, Circuit-B, i.e., a circuit expressing the CI protein at a sufficient level by the addition of the activating substance AHL and not expressing the CI protein at the time of the addition of AHL. First, a TK-deficient *E. coli* strain harboring Circuit-B and pPL-hsvtk (referred to as "Switch-2 cells"), a TK-deficient *E. coli* strain harboring Circuit-C and pPL-hsvtk (referred to as "ON cells"), and a TK-deficient *E. coli* strain harboring Circuit-D and pPL-hsvtk (referred to as "OFF cells") were prepared, and were mixed at about 1:1:1. This pool of cells was subjected to ON selection, followed by OFF selection ((a) of FIG. 8). The ON selection was conducted as follows: the mixed cells were inoculated in LB medium containing no AHL and cultured at 37° C. for 12 hours, then the culture was inoculated in tryptone solid medium containing 10 μg/mL of 5FdU, 10 μg/mL of dT, and 10 μg/mL of uridine and incubated at 37° C. for an additional 20 hours. Colonies formed by surviving the ON selection were recovered in LB liquid medium, inoculated in LB medium containing 1 μM AHL, and cultured at 37° C. for 3 hours. 20 μL of the culture (approximately $10^6$ cells) were collected and subjected to OFF selection. That is, the collected culture was inoculated in LB solid medium containing 100 nM dP and 1 μM AHL to form colonies. After that, a group of cells was recovered, and plasmids were extracted. The extracted plasmids were cotransformed with pPL-gfpuv into XL10-GOLD™ ultracompetent cells (Agilent Technologies) and the activities of the genetic circuits were evaluated based on the fluorescence of GFPuv. The transformants were inoculated in solid media supplemented and not supplemented with 1 μM AHL. After 12 hours, the number of cells expressing GFPuv and the number of cells not expressing GFPuv were compared on the two plates of solid media to measure selection efficiency.

Through the ON selection first conducted, the Switch-2 cells harboring Circuit-B and the ON cells having Circuit-C were selected. Through the OFF selection further conducted, the ON cells having Circuit-C almost disappeared, and only the Switch-2 cells harboring Circuit-B were recovered ((c) of FIG. 8).

Experimental Example 6

The OFF selection method and ON selection method for a genetic switch and a genetic circuit established in Experimental Examples 1 and 2 were employed to study the selection of a desired genetic switch and genetic circuit by dual selection. OFF selection and ON selection were conducted with liquid media ((b) of FIG. 8). It is an essential requirement for the shortening of the operation time and automation to conduct dual selection in liquid media.

Specifically, the conducted study involved mixing Genetic Circuits-B, C, and D produced in Experimental Example 4, and enriching/obtaining, therefrom, Circuit-B, i.e., a circuit expressing the CI protein at a sufficient level by the addition of the activating substance AHL and not expressing the CI protein at the time of the addition of AHL, from the mixture with other circuits (C and D). First, the OFF cells, ON cells, and Switch-2 cells prepared in Experimental Example 5 were mixed at a ratio of 1,000:1,000:1 or 10,000:10,000:1. The ON cells, the OFF cells, and the Switch-2 cells harbor Circuit-C, Circuit-D, and Circuit-B, respectively, and pPL-hsvtk. The mixed cells were subjected to OFF selection and ON selection. More specifically, the mixed cells were cultured overnight, and then diluted with 1 mL of LB medium containing 100 μg/mL of ampicillin and 30 μg/mL of chloramphenicol to adjust the cell density so as to achieve a final OD600 of 0.002. The resultant was incubated in the presence of AHL (1 μM) and dP (100 nM) for 1 hour to conduct OFF selection. Next, cells obtained through the OFF selection were recovered by centrifugation, washed twice with 1 mL of a solution containing 0.9% w/v NaCl, resuspended in 1 mL of LB medium, and cultured at 37° C. for 2 hours. 10 μL of the culture were collected, added to 1 mL of positive selection medium containing no AHL, and cultured for 20 hours while being rotated at 200 rpm to conduct ON selection. After that, a group of cells were recovered, and plasmids were extracted. The extracted plasmids were cotransformed with pPL-gfpuv into XL10-GOLD™ ultracompetent cells (Agilent Technologies), and the activities of the genetic circuits were evaluated based on the fluorescence of GFPuv. The transformants were inoculated in solid media supplemented and not supplemented with 1 μM AHL. After 12 hours, the number of cells expressing GFPuv and the number of cells not expressing GFPuv were compared on the two plates of solid media to measure selection efficiency.

Table 1 shows the results. When the OFF cells, the ON cells, and the Switch-2 cells were mixed at a ratio of 1,000:1,000:1, the ratio of the Switch-2 cells contained in the mixed cells before the dual selection was 0.05%, but was enriched to 83.6% after the dual selection with an enrichment factor of $1.67 \times 10^3$. Further, when the OFF cells, the ON cells, and the Switch-2 cells were mixed at a ratio of 10,000:10,000:1, the ratio of the Switch-2 cells contained in the mixed cells before the dual selection was 0.005%, but was enriched to 82.0% after the dual selection with an enrichment factor of $1.64 \times 10^4$.

TABLE 1

|  |  | Mixing ratio before selection (ON cells:OFF cells:Switch-2 cells) | |
| --- | --- | --- | --- |
|  |  | $10^3:10^3:1$ | $10^4:10^4:1$ |
| Ratio of Switch-2 (%) | Before selection | 0.05 | 0.005 |
| Ratio of Switch-2 (%) | After selection | 83.6 | 82.0 |
| Enrichment factor |  | 1,672 | 16,409 |

In the dual selection, OFF selection was first conducted and ON selection was then conducted. Even when the order of the selection methods is reversed, similar selection results are obtained (unpublished data).

Thus, it was verified that through the use of the OFF selection and ON selection according to the present invention, a functional genetic switch and genetic circuit, i.e., the Switch-2 cells very slightly contained in large amounts of non-functional genetic switches and genetic circuits, i.e., the OFF cells and the ON cells were able to be selected with high efficiency and within a short time period, and were able to be enriched.

Experimental Example 7

The OFF selection method and ON selection method for a genetic switch and a genetic circuit established in Experimental Examples 1 and 2 were employed to study the separation/selection of genetic switches and genetic circuits with different output properties (response thresholds) by dual selection.

Specifically, a TK-deficient *E. coli* strain harboring Circuit-A and pPL-hsvtk (referred to as "Switch-1 cells") and the TK-deficient *E. coli* strain harboring Circuit-B and pPL-hsvtk (Switch-2 cells) were mixed at a ratio of 1:1, and subjected to OFF selection through the use of 10 nM AHL, followed by ON selection through the use of 5FdU in the absence of AHL. PCR was conducted with the culture solution after each selection process, and a ratio between cells containing the respective circuits was measured. As illustrated in FIG. 9-A, Circuit-A and Circuit-B can be distinguished by PCR. In each of Circuit-A and Circuit-B, a certain region of the circuit containing part of the CI structural gene is amplified by PCR with the same primer set. Circuit-A contains the wild-type of the CI structural gene, while Circuit-B contains a truncated variant of the CI structural gene. Thus, a PCR product (367 bp) using Circuit-B as a template is shorter in length than a PCR product (639 bp) using Circuit-A as a template. Accordingly, PCR of a mixture of both provides two bands corresponding to the different lengths. An abundance ratio between both is determined based on an intensity ratio between the bands.

FIG. 9-B shows the results. In the mixed cells before the selection, the bands of both the Switch-1 cells and the Switch-2 cells were able to be confirmed at almost the same intensity (Lane 3 of FIG. 9-B). After the OFF selection, the band of the Switch-1 cells was found to be denser (Lane 4 of FIG. 9-B). Under the conditions of using 10 nM AHL, the Switch-1 cells more strictly repress the expression of hsvTK than the Switch-2 cells do (the panel (a) of FIG. 7). After the subsequent ON selection, the intensities of the bands of the Switch-1 cells and the Switch-2 cells were both equivalent to the intensities of the bands after the OFF selection (Lane 5 of FIG. 9-B).

The difference between the Switch-1 cells and the Switch-2 cells is the difference between the circuits harbored. The Switch-1 cells harbor Circuit-A containing a gene encoding the full-length CI protein, and the Switch-2 cells harbor Circuit-B containing a gene encoding a C-terminal truncated CI protein. Although each of both the circuits acts as a genetic circuit that causes ON/OFF of the expression of the CI protein in an AHL concentration-dependent manner, Circuit-A is higher than Circuit-B in the ability to repress the expression of the CI protein. Hence, the Switch-1 cells harboring Circuit-A were efficiently enriched through the dual selection.

Example 1

Plasmids to be used as ON-selectors (ON-selector plasmids), and plasmids usable as both of ON-selectors and OFF-selectors (dual selector plasmids) were prepared (FIG. 10).

First, plasmid pCI-gfp, which served as a basis for the preparation of the selector plasmids, was prepared. A plasmid map of this plasmid is illustrated in FIG. 11, and its sequence is set forth in SEQ ID NO: 8. pCI-gfp has a gfpuv gene inserted downstream of a lambda phage-derived PR promoter so that the CI protein represses the transcription of the gfp gene. pCI-gfp was prepared by obtaining a PR promoter-gfp gene site in Plux-cI-gfp by PCR and inserting the site through the utilization of a ClaI-HindIII site in pAC-aid. The expression of gfpuv and its repression by the CI protein were confirmed.

The ON-selector plasmids and control plasmids therefor were prepared.
1. pTrc-aag (WT)
2. pTrc-aag (E125A)
3. pTrc-aag (L180F)
4. pTrc-aag-ape1
5. pTrc-ape1 pTrc-aag (WT) is a plasmid containing a wild-type AAG gene. A plasmid map thereof is illustrated in FIG. 12-A, and its nucleic acid sequence is set forth in SEQ ID NO: 5. This plasmid is prepared by transfecting the AAG gene into a pTrc vector, and can induce IPTG. The acquisition of MMS resistance has been confirmed in a 3-methyladenine repair enzyme-deficient strain.

pTrc-aag (E125A) is a plasmid containing a gene encoding an AAG variant AAG (E125A). AAG (E125A) is a variant in which glutamic acid at position 125 in the amino acid sequence of AAG is substituted by alanine, the glycosidase activity is lost, and hence the alkylated DNA repair function of AAG is lost.

pTrc-aag (L180F) is a plasmid containing a gene encoding an AAG variant AAG (L180F). AAG (L180F) is a variant in which leucine at position 180 in the amino acid sequence of AAG is substituted by phenylalanine, and was found as an MMS-resistant variant (Chen et al., DNA Repair, 7,1731 (2008)).

pTrc-aag-ape1 is a plasmid containing a wild-type AAG gene and an Ape1 gene. A plasmid map thereof is illustrated in FIG. 12-B, and its nucleic acid sequence is set forth in SEQ ID NO: 6. APE1 was obtained by PCR, and was inserted downstream of the aag gene of pTrc-aag (WT) with EcoRI-HindIII. The AAG (wt) gene and Ape1 gene were placed downstream of the Trc promoter. The expression of both genes can be induced by IPTG. Both genes have AGGAGG introduced upstream of ATG. Cloning sites are NcoI-EcoRI and EcoRI-HindIII. The acquisition of MMS resistance has been confirmed in a 3-methyladenine repair enzyme-deficient strain. The acquisition of MMS resistance higher than that of pTrc-aag has been confirmed.

pTrc-ape1 is a plasmid containing an Ape1 gene. A plasmid map thereof is illustrated in FIG. 12-C, and its sequence is set forth in SEQ ID NO: 7.

Four kinds of dual selector plasmids were prepared.
1. pCI-aag-hsvTK (referred to as "selector plasmid Ver. 1")
2. pCI-aag-hsvTK-ape1 (referred to as "selector plasmid Ver. 2")
3. pCI-aag (L180F)-hsvTK-ape1 (referred to as "selector plasmid Ver. 2.1")
4. pCI-aag-hsvTK-ape1 (referred to as "selector plasmid Ver. 3")

A plasmid map of pCI-aag-hsvTK (selector plasmid Ver. 1) is illustrated in FIG. 13-A, and its sequence is set forth in SEQ ID NO: 1. Based on pCI-gfp, its gfp fragment was cleaved off and substituted by wild-type AAG and hsvTK obtained by PCR. The sequences of the AAG and hsvTK fragment obtained by PCR have already been confirmed. pCI-aag-hsvTK has AAG (wt) and hsvTK placed in tandem at a NcoI-HindIII site downstream of the PR promoter of pCI-gfp. Both the genes have AGGAGG-bound upstream of a start codon. AAG can be cleaved off with NcoI-XbaI, and hsvTK can be cleaved off with XbaI-HindIII. Fusion can be caused at the XbaI site in front of the stop codon of AAG and the SpeI site upstream of hsvTK. The function of the plasmid as a dP kinase (OFF-selector) has already been verified, and its ON-selector function in MMS selection has also already been verified.

A plasmid map of pCI-aag-hsvTK-ape1 (selector plasmid Ver. 2) is illustrated in FIG. 13-B, and its sequence is set forth in SEQ ID NO: 2. Vectors were prepared by PCR from downstream of hsvTK of pCI-aag-hsvTK (selector plasmid Ver. 1) and from downstream of the Cm resistance gene thereof. An ape1 gene was obtained by PCR, and inserted downstream of the Cm resistance gene with a BamHI site and a blunt. AGGAGG was added upstream of the ape1 gene so that the gene was translated. An XhoI site was added upstream of AGGAGG so as to allow a promoter sequence or the like to be inserted upstream of ape1. It is impossible to cleave out only APE1 because introduction thereof was done using blunt end. The function of the plasmid as a dP kinase (OFF-selector) has already been verified, and its ON-selector function in MMS selection has also already been verified.

A plasmid map of pCI-aag (L180F)-hsvTK-ape1 (selector plasmid Ver. 2.1) is illustrated in FIG. 13-C, and its sequence is set forth in SEQ ID NO: 3. Through the utilization of the NcoI-SpeI site of pCI-aag-hsvTK-ape1 (selector plasmid Ver. 2), AAG (L180F) obtained by PCR was transfected. The function of the plasmid as a dP kinase (OFF-selector) has already been verified, and its ON-selector function in MMS selection has also already been verified.

A plasmid map of pCI-aag-hsvTK-ape1 (selector plasmid Ver. 3) is illustrated in FIG. 13-D, and its sequence is set forth in SEQ ID NO: 4. An XhoI-BamHI site located upstream of the APE1 gene of pCI-aag-hsvTK-ape1 (selector plasmid Ver. 2) was utilized to transfect a lacIq promoter sequence obtained by PCR. The insertion of the lacIq promoter sequence upstream of APE1 increases the expression level of APE1. The function of the plasmid as a dP kinase (OFF-selector) has already been verified, and its ON-selector function in MMS selection has also already been verified. However, as compared to selector plasmid Ver. 2, no improvement in the function as an ON-selector could be found.

Example 2

The ON-selector function of the AAG gene was studied. First, alkylating agent-sensitive $E.$ $coli$ strains MV2157 were separately transfected with plasmids containing AAG and variants thereof, specifically, pTrc-aag (WT), pTrc-aag (E125A), and pTrc-aag-ape1 prepared in Example 1, and were compared for their survival rates in the presence/absence of MMS. The $E.$ $coli$ strain transfected with pTrc-aag (E125A) was used as a negative control.

Specifically, the $E.$ $coli$ strains transfected with the various plasmids were each inoculated in 2 mL of LB medium, and cultured at 37° C. for 12 hours. Next, 1 µL of culture was inoculated in LB liquid medium, and cultured at 37° C. for 3 hours. MMS was added at a final concentration of 0 to 40 mM, and culture was conducted at 37° C. for 15 to 60 minutes. The culture solution was inoculated in LB solid medium, and a viable cell count was measured from the number of colonies. A value obtained by dividing the viable cell count of the sample to which MMS had been added by the viable cell count of the sample to which MMS had not been added was defined as a survival rate.

The treatment with various concentrations of MMS (10 to 40 mM) for 30 minutes decreased the survival rate of the $E.$ $coli$ strain not expressing AAG by about 5 to 6 digits (the panel (a) of FIG. 14). On the other hand, the $E$ $coli$ strains expressing AAG had small degrees of decrease in survival rate, and showed high survival rates as compared to the $E.$ $coli$ strain not expressing AAG, specifically survival rates that reached a maximum with a $10^3$-fold value under the condition of a concentration of MMS of 10 to 20 mM. The decrease in survival rate of cells is further reduced by coexpressing AAG and Ape1. It should be noted that when the concentration of MMS was further increased (~40 mM), all the strains were mostly died off. It may be considered that MMS causes alkylation of proteins and the like in cells as well as DNA and hence causes cell death irrespective of the presence or absence of DNA repair.

Next, a time-dependent change in the survival rate after the MMS treatment was observed with a fixed concentration of MMS of 20 mM (the panel (b) of FIG. 14). At any time point, the ranking order of the survival rates was as follows: AAG-APE1 strain>AAG strain>>control strain. When the MMS treatment was conducted for 60 minutes, the survival rates of cells expressing AAG also significantly decreased.

Those results revealed that through the MMS treatment for a short time period of 15 to 60 minutes, cells expressing AAG were able to be enriched about ~1,000-fold. The conditions of conducting "treatment with MMS at a concentration of 20 mM for 30 minutes," under which such high enrichment efficiency is stably obtained, were adopted as standard selection conditions in the case of conducting ON selection in any of Examples below.

Example 3

The ON-selector function of the AAG gene was utilized to study the selection of a genetic circuit. Selector plasmid Ver. 2, which was prepared in Example 1 as a plasmid having the AAG gene, was used (FIG. 13-B). Circuit-C or Circuit-D was used as a model genetic circuit.

First, $E.$ $coli$ MV2157 transfected with selector plasmid Ver. 2 and Circuit-C (referred to as "ON strain" in Example 3), and $E.$ $coli$ MV2157 transfected with selector plasmid Ver. 2 and Circuit-C (referred to as "OFF strain" in Example 3) were prepared. Each of those $E.$ $coli$ strains was inoculated in 2 mL of LB medium, and cultured at 37° C. for 12 hours. Next, 1 µL (approximately $10^7$ cells) of each culture was inoculated in LB liquid medium and cultured at 37° C. for 3 hours, followed by medium exchange to M9 minimal medium, and MMS was added at 0.2%, 0.3%, or 0.4%, followed by incubation at 37° C. for 15 to 60 minutes. The cell density at the time of the MMS treatment is approximately $10^8$ cells/mL. The culture solution was recovered and inoculated in LB solid medium, and a viable cell count was measured from the number of colonies formed. A value obtained by dividing the viable cell count of the sample to which MMS had been added by the viable cell count of the sample to which MMS had not been added was defined as a survival rate.

Next, time-dependent changes in the survival rates of the ON strain and the OFF strain when MMS was added at 0.2% were investigated. In this case, an ON strain transfected with pTrc-ape1 was prepared and similarly studied for comparison. Culture and treatment with MMS of each strain of $E.$ $coli$ were conducted by similar methods to the methods in the foregoing.

FIG. 15-A and FIG. 15-B show the results. The group of genes contained in the selector plasmid are under control of the PR promoter, and their expression is repressed by the CI protein. Circuit-D constitutively expresses CItruc, and hence the selector gene is in an OFF (repressed) state. Accordingly, the AAG gene is not expressed in the OFF strain, and as a result, the survival rate of $E.$ $coli$ significantly decreased by the MMS treatment (FIG. 15-A). As the concentration of MMS was higher, the survival rate of the OFF strain not expressing AAG decreased more remarkably (FIG. 15-A). Further, as the time of the treatment with MMS was longer, the survival rate of the OFF strain not expressing AAG decreased more remarkably (FIG. 15-A). On the other hand, Circuit-C does not express the CI protein, and hence the selector gene is in an ON (triggered) state. Therefore, the AAG gene was expressed in the ON strain, and as a result, the survival rate only slightly reduced even after the MMS treatment (FIG. 15-A). The difference in survival rate between the OFF strain and the ON strain reached a $10^4$-fold or more difference under some conditions (when treated with MMS at 0.4% for 30 minutes). It should be noted that even when the selector gene was in a triggered state and AAG was expressed, the survival rate was found to reduce in the presence of MMS at a certain concentration or higher. It is surmised that this is because the amount of methylated DNA exceeded the methylated DNA repairing ability of the AAG/Ape1 pathway, or MMS caused methylation of proteins in the cells and cell membranes, resulting in the induction of cell death.

As shown in FIG. 15-B, when pTrc-ape1 was transfected into the ON strain to additionally increase the expression of ape1, its survival rate further increased. Ape1 has been reported to have an effect of increasing the turnover of AAG (Baldwin, et al., Biochemistry, 48, 6022 (2009)), and the results shown in FIG. 15-B can be considered to be due to such effect of Ape1.

Through the utilization of the change in the survival rate of the alkylating agent-sensitive *E. coli* strain in the presence of MMS depending on the presence or absence of the expression of AAG, it is possible to conduct functional selection of a genetic switch or genetic circuit set so as to control an AAG gene-expressing circuit. That is, when a genetic switch or genetic circuit operates and the expression of AAG downstream thereof is caused, the survival rate of the alkylating agent-sensitive *E. coli* strain in the presence of MMS increases. Therefore, through the selection of an alkylating agent-sensitive *E. coli* strain having a high survival rate in the presence of MMS, it is possible to select a genetic switch or genetic circuit in an ON state, which can cause the expression of AAG.

Thus, a selection approach involving picking up only a genetic switch and genetic circuit in an ON state through the use of the alkylating agent-sensitive *E. coli* strain transfected with the AAG gene was able to be established.

Example 4

An attempt was made to improve the ON-selector function of the AAG gene. As an MMS-resistant variant of AAG, there has been obtained a variant (AAG (L180F)) in which leucine at position 180 in the amino acid sequence of AAG is substituted by phenylalanine (Chen et al., DNA Repair, 7, 1731 (2008)). In view of this, the function of this variant (hereinafter referred to as "L180F variant") as a selector gene was tested.

First, the MMS resistance of the L180F variant was confirmed. *E. coli* MV2157 transfected with plasmid pTrc-aag (WT) containing a wild-type AAG gene or plasmid pTrc-aag (L180F) containing the L180F variant gene was inoculated in 2 mL of LB medium, and cultured at 37° C. for 12 hours. Next, 1 µL (approximately $10^6$ cells) of each culture was inoculated in LB liquid medium and cultured under shaking at 37° C. for 3 hours, and then treated in the presence or absence of 0.2% MMS at 37° C. for 30 minutes. The culture solution was inoculated in LB solid medium, and a viable cell count was measured from the number of colonies.

Figure 16:
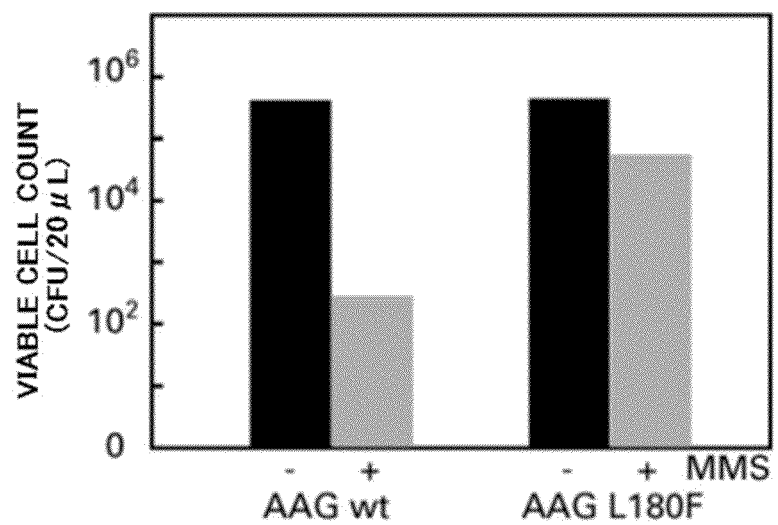
[FIG. 16] A graph showing that E. coli expressing a variant (AAG (L180F)) in which leucine at position 180 in the amino acid sequence of AAG was substituted by phenylalanine showed significantly higher MMS resistance than E. coli expressing wild-type AAG (Example 4).

As a result, *E. coli* expressing the L180F variant showed significantly higher MMS resistance than *E. coli* expressing wild-type AAG (FIG. 16). Under some conditions, the number of cells of *E. coli* surviving the MMS treatment, i.e., *E. coli* holding the ability to form a colony in the subsequent culture becomes higher than that of the wild-type by as much as 2 digits. Thus, it was able to be confirmed that the L180G variant showed MMS resistance.

Next, the function of the L180F variant as a selector gene was studied. Selector plasmid Ver 2.1 obtained by putting a site-directed mutation into the AAG gene of selector plasmid Ver. 2 (see Example 1 and FIG. 13-C) or selector plasmid Ver. 2 (see Example 1 and FIG. 13-B) was transfected into *E. coli* MV2157. Each of those *E. coli* strains was inoculated in 2 mL of LB medium, and cultured at 37° C. for 12 hours. After that, 1 µL (approximately $10^6$ cells) of each culture was inoculated in LB liquid medium, cultured at 37° C. for 2 hours under shaking, and treated in the presence or absence of 0.2% MMS at 37° C. for 30 minutes. The culture solution was inoculated in LB solid medium, and a viable cell count was measured from the number of colonies. Further, as a negative control, *E. coli* MV2157 transfected with plasmid pCI-gfp was similarly treated.

Figure 17:
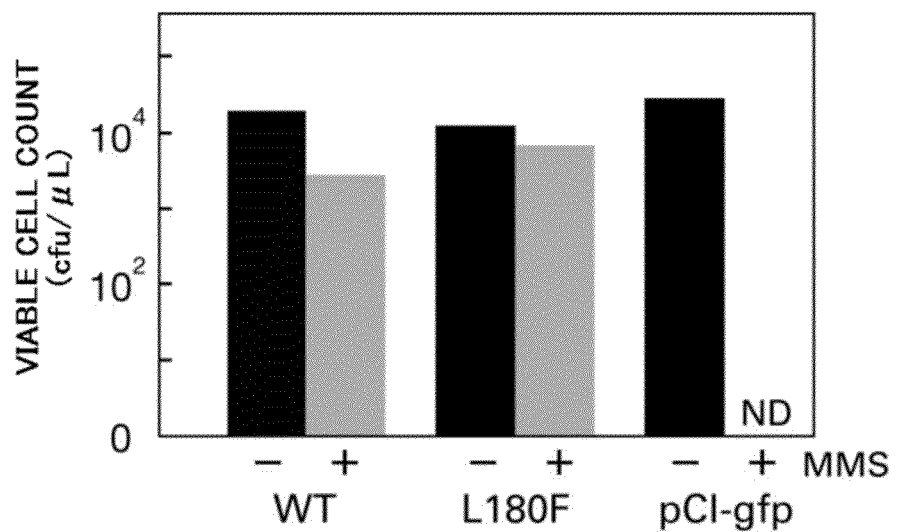
[FIG. 17] A graph showing that when the group of genes of a selector plasmid was in a triggered state, E. coli transfected with selector plasmid Ver 2.1 (pCI-aag (L180F)-hsvTK-ape1) showed a remarkably high survival rate against MMS treatment as compared to E. coli transfected with selector plasmid Ver. 2 (pCI-aag-hsvTK-ape1). In the figure, ND means "not detected" (Example 4).

As a result, as shown in FIG. 17, when the group of genes of the selector plasmid was in a triggered state, *E. coli* transfected with selector plasmid Ver 2.1 showed a remarkably high survival rate as compared to *E. coli* transfected with selector plasmid Ver. 2. Specifically, in the case of *E. coli* transfected with Ver. 2, the ratio of the viable cell count in the case of conducting the MMS treatment to the viable cell count in the case of not conducting the MMS treatment was 0.14. Meanwhile, under the same conditions, in the case of *E. coli* transfected with Ver. 2.1, the ratio of the viable cell count in the case of conducting the MMS treatment to the viable cell count in the case of not conducting the MMS treatment was 0.53.

Since L180G variant shows high MMS resistance as described above, efficiency of the ON selection becomes extremely high when using the L180G variant gene. It is considered that, in the dP selection using hsvTK shown in Experimental Examples 1 to 7, the AAG wild-type has an activity to reduce its toxicity (dP glycosylase activity). Accordingly, when the AAG wild-type is used for ON selection, in the case of conducting OFF selection following the ON selection, the OFF selection using hsvTK as a selector is conducted in the presence of dP, and hence the efficiency of the OFF selection may be decreased. It is considered that the L180F variant has a low dP glycosylase activity and hence does not inhibit the selector function of hsvTK. Therefore, when the L180F variant is used as an ON-selector, the overall efficiency and usefulness of the selection system in which ON selection and OFF selection are alternately conducted become extremely high.

Example 5

ON selection using AAG as a selector and OFF selection using hsvTK as a selector were employed to conduct the dual selection of a desired genetic switch and genetic circuit.

First, dual selection was conducted on a trial basis. Selector plasmid Ver. 2 (FIG. 13-B) was used as a selector plasmid, and the following three kinds of model genetic circuits were used: Circuit-B expressing CItruc by AHL; Circuit-C not expressing CItruc irrespective of the presence or absence of AHL; and Circuit-D always expressing CItruc irrespective of the presence or absence of AHL (see FIGS. 2-B, 2-C, and 2-D). The selector plasmid and one kind of model genetic circuit were transfected into E. coli MV2157. An E. coli strain transfected with a circuit and a selector plasmid as described above is called a switch strain. The switch strains having Circuit-B, Circuit-C, or Circuit-D were mixed at an abundance ratio of 1:1:1 in terms of optical density (OD). The mixed cell population was inoculated in 1 mL of liquid dP selection medium containing AHL at 1 µM (LB, 1 µM dP) at approximately $10^7$ cells, and cultured under shaking at 37° C. for 1 hour. The cells were harvested by centrifugation, washed with an aqueous solution containing 0.9% NaCl, and then resuspended in LB liquid medium (OFF selection). After that, culture was conducted at 37° C. for 2 hours, and the cells were harvested by centrifugation. Then, the medium was exchanged for M9 minimal medium, MMS was added, and the whole was left to stand still at 37° C. for 30 minutes (ON selection). Subsequently, the medium was exchanged for LB medium, culture was conducted for 12 hours, and plasmids were extracted from the culture solution. The plasmids were transformed together with pλ-gfp into XL10-GOLD™ ultracompetent cells (Agilent Technologies). After that, the transformed cells were inoculated in solid media supplemented and not supplemented with AHL, and the numbers of cells expressing green fluorescent protein (GFP) were compared.

FIG. 18-A illustrates a schematic diagram of the steps conducted. Further, FIG. 18-B shows GFP expression patterns of the cell population before the start of selection, after OFF selection, and after ON selection under the respective conditions of the addition of AHL and the addition of no AHL. Outputs, i.e., CItruc expression, of Circuit-B, Circuit-C, and Circuit-D under the conditions of the addition of AHL and the addition of no AHL are +/−, −/−, and +/+, respectively. That is, the expression of the gene located downstream thereof and under control of the PR promoter that is repressed by CItruc is the reverse of the foregoing, i.e., −/+, +/+, and −/−. Therefore, it is only Circuit-C that shows fluorescence due to GFP in the plate supplemented with AHL, and it is Circuit-B and Circuit-C that show fluorescence due to GFP in the plate supplemented with no AHL. As illustrated in FIG. 18-B, after the OFF selection had been conducted, the switch strain having Circuit-C, i.e., colonies showing fluorescence with the addition of AHL were substantially absent, while in contrast, the switch strain having Circuit-D, i.e., colonies showing no fluorescence with the addition of no AHL were present in a large number. The results revealed that the OFF selection allowed the cells not expressing hsvTK, i.e., the switch strain having Circuit-D to survive, while induced cell death of the cells expressing hsvTK, i.e., the switch strain having Circuit-C. Further, the switch strain having Circuit-B, which did not express hsvTK in the presence of AHL, survived. After the ON selection had been conducted following the OFF selection, in the switch strain having Circuit-D, which did not express AAG irrespective of the presence or absence of the addition of AHL, cell death was induced, and the switch strain having Circuit-B, which expressed AAG in the absence of AHL, evaded cell death due to MMS and survived.

Next, enrichment efficiency by dual selection was evaluated. Selector plasmid Ver. 2 (FIG. 13-B) was used as a selector plasmid, and the following three kinds of model genetic circuits were used: Circuit-B; Circuit-C; and Circuit-D (see FIGS. 2-B, 2-C, and 2-D). The selector plasmid and one kind of model genetic circuit were transfected into E. coli MV2157. Each switch strain was inoculated in 2 mL of LB medium containing AHL, and cultured at 37° C. for 12 hours. Next, the switch strains having Circuit-B, Circuit-C, or Circuit-D were mixed at an abundance ratio of 1:100:100 in terms of OD. The mixed cell population was subjected to OFF selection by the same method as above, and then cultured at 37° C. for 2 hours. The cells were harvested by centrifugation, the medium was exchanged for M9 minimal medium, MMS was added at a concentration of 0.2%, 0.3%, or 0.4%, and the whole was left to stand still at 37° C. for 30 minutes (ON selection). After that, the medium was exchanged for LB medium, culture was conducted for 12 hours, and plasmids were extracted from the culture solution. The plasmids were transformed together with pλ-gfp into XL10-GOLD™ ultracompetent cells (Agilent Technologies). After that, the transformed cells were inoculated in solid media supplemented and not supplemented with AHL, and the numbers of cells expressing GFP were compared. A value obtained by dividing the ratio of the switch strain after the selection by the ratio of the switch strain before the selection was defined as an enrichment factor.

Table 2 shows the enrichment factor of the circuit by the dual selection. Table 2 shows the enrichment factor of Circuit-B after conducting OFF selection (1 µM AHL), followed by ON selection (addition of no AHL) for the cell population obtained by mixing the switch strains at Circuit-B:Circuit-C:Circuit-D=1:100:100.

TABLE 2

| Concentration of MMS in ON selection | 0.2% | 0.3% | 0.4% |
|---|---|---|---|
| Before selection [%] | 0.5 | 0.5 | 0.5 |
| After dual selection [%] | 20 | 83 | No surviving cells |
| Enrichment factor | 40 | 166 | — |

As shown in Table 2, when the concentration of MMS in the ON selection (for 30 minutes) was 0.2% or 0.3%, Circuit-B was found to be significantly enriched. On the other hand, all the cells were killed in the case of the treatment with 0.4% MMS. This reflects the cell density at the time of the selection experiment. The cell density in the MMS treatment in Example 2 was approximately $10^8$ cells/mL, whereas the cell density in the conditions of Example 5 was lower by as much as 2 digits, i.e., approximately $10^6$ cells/mL. Thus, it is considered that the effective concentration of MMS was higher.

In addition, enrichment efficiency by dual selection was evaluated with various mixing ratios of switch strains. In this case, selector plasmid Ver. 2 (FIG. 13-B) and selector plasmid Ver. 2 (FIG. 13-C) were used, and selection efficiencies obtained with the plasmids were compared. The following three kinds of model genetic circuits were used: Circuit-B; Circuit-C; and Circuit-D (see FIGS. 2-B, 2-C, and 2-D). Any one of the selector plasmids and one kind of model genetic circuit were transfected into E. coli MV2157. Each switch strain was inoculated in 2 mL of LB medium containing AHL, and cultured at 37° C. for 12 hours. Next, the switch strains having Circuit-B, Circuit-C, or Circuit-D were mixed at an abundance ratio of 1:1,000:1,000 in terms of OD. The mixed cell population was subjected to OFF selection by the same method as above and then cultured at 37° C. for 2 hours. The cells were harvested by centrifugation, the medium was exchanged for M9 minimal medium, MMS was added at a concentration of 0.2%, and the whole was left to stand still at 37° C. for 30 minutes (ON selection). After that, the medium was exchanged for LB medium, culture was conducted for 12 hours, and plasmids were extracted from the culture solution. After that, the transformed cells were inoculated in solid media supplemented and not supplemented with AHL, and the numbers of cells expressing GFP were compared. A value obtained by dividing the ratio of the switch strain after the selection by the ratio of the switch strain before the selection was defined as an enrichment factor.

Table 3 shows the enrichment factor of the circuit by the dual selection. Table 3 shows the enrichment factor of Circuit-B after conducting OFF selection (1 μM AHL), followed by ON selection (addition of no AHL) for the cell population obtained by mixing the switch strains at Circuit-B:Circuit-C: Circuit-D=1:1,000:1,000.

TABLE 3

| Ver. 2 | | Ver. 2.1 | |
|---|---|---|---|
| Circuit-B | 20.4% (409 times) | Circuit-B | 96.8% (1.935 times) |
| Circuit-C | 4.3% | Circuit-C | 1.1% |
| Circuit-D | 75.3% | Circuit-D | 2.2% |

As shown in Table 3, when selector plasmid Ver. 2 was used, about 400-fold enrichment of Circuit-B was observed. Circuit-C was efficiently removed, and hence the efficiency of the ON selection was sufficiently high. In contrast, a considerable amount of Circuit-D survived. On the other hand, when selector plasmid Ver. 2.1 was used, Circuit-B accounted for almost the entirety and showed an enrichment factor of 1,935, a score very close to the theoretical maximum enrichment factor (2,000). The survival rate of Circuit-C, as compared to the case of using selector plasmid Ver. 2, significantly decreased as well. This is probably because the transfection with AAG improved the viable cell ratio of the L180F variant. Further, the survival rate of Circuit-D, which was the problem in selector plasmid Ver. 2, ameliorated more remarkably. It is surmised that this is due to the following: the dP glycosylase activity of AAG is reduced in the L180F variant.

Thus, it has become possible to conduct the selection of a genetic switch and a genetic circuit within extremely short time periods, i.e., 30 minutes for ON selection and 60 minutes for OFF selection.

Example 6

One of the advantages of the approach established in Example 4 resides in that selection along time course can be conducted; for example, selection with respect to the switching time (latency) of a genetic switch can be conducted. In view of this, "selection based on a switching time" was conducted using Circuit-A and Circuit-B.

First, selector plasmid Ver. 2.1 (FIG. 13-C) and Circuit-A were transformed into *E. coli* MV2157 (hereinafter referred to as "Cells-A"). Further, selector plasmid Ver. 2.1 (FIG. 13-C) and Circuit-B were transformed into *E. coli* MV2157 (hereinafter referred to as "Cells-B"). Circuit-A and Circuit-B express the full-length CI protein and CItruc, respectively, placed downstream of the Lux promoter, depending on the concentration of AHL. CItruc is a C-terminal truncated CI protein, and has a decreased ability to bind to a target sequence, resulting in a decreased ability to repress the PL promoter. Therefore, when Circuit-A and Circuit-B operate in the presence of AHL, the expression of the groups of genes contained in the selector plasmids and placed downstream of these circuits is repressed. However, the degree of the repression is larger for Circuit-A as compared to Circuit-B.

Next, Cells-A and Cells-B were each precultured in LB medium containing AHL at 1 μM. Next, the cells were inoculated in fresh LB medium containing no AHL while the number of cells was adjusted to approximately $10^6$ cells through optical density (OD) measurement. The culture solution was cultured under shaking at 37° C. To the culture solution 1, 3, or 6 hours after the start of the culture was added MMS at a final concentration of 0.2%, and the resultant was cultured under shaking at 37° C. The cells were harvested by centrifugation from the culture solution cultured for 30 minutes after the addition of MMS, were diluted to 1/100, and were then inoculated in fresh LB medium. After medium exchange, culture was conducted for 12 hours, and *E. coli* contained in the culture solution was directly subjected to PCR reaction. The reaction solution after the PCR reaction was subjected to gel electrophoresis to analyze an abundance ratio thereof.

When the switching time of the group of genes contained in the selector plasmid from a non-expression state (OFF) to an expression state (ON) is short, i.e., when culture in medium containing no AHL was for 1 hour, Cells-A containing Circuit-A were mostly eliminated by selection, and only Cells-B containing Circuit-B were picked out. This "picking" was not observed when a time interval between selection operations was sufficiently long, i.e., when culture in medium containing no AHL was for 6 hours (FIG. 19).

The results can be discussed as follows. When the intracellular half-life of CItruc to be expressed by the operation of Circuit-B is considered to be shorter than that of the full-length CI protein to be expressed by the operation of Circuit-A, the time required until its repressive effect disappears to express the gene contained in the selector plasmid is shortened. When AHL is removed to stop resynthesis of CItruc, the repression in cells by CI is eliminated early. After a time period of as much as 6 hours, the difference between the survival rate of cells expressing the full-length CI protein and the survival rate of cells expressing CItruc disappears. This may be because the time period after the removal of AHL elongated and hence the repression by the full-length CI protein was also eliminated. Alternatively, that may be because, for CItruc, the cell concentration required to completely repress the promoter on which the CI protein acts was higher, and hence the time required to eliminate the repressive effect was shorter.

As described above, through the use of the ON-selector function of the dual selector plasmid, a "circuit with a short OFF→ON switching time" was able to be easily enriched. Through the use of the dual selector plasmid, it is also possible to select genetic switches and genetic circuits with various functions such as an "effector to be quickly decomposed," an "effector that starts to take effect quickly," a "circuit that is durable (has high memory retention)," and "regulation of a pulse time."

INDUSTRIAL APPLICABILITY

According to the present invention, it is possible to provide the method by which genetic switches and genetic circuits with desired properties and/or functions can be selected and obtained rapidly and with high efficiency.

The present invention is an extremely useful invention that contributes to a wide range of fields such as protein production, metabolic engineering, and synthetic biology.

Sequence Listing Free Text

SEQ ID NO: 1: Designed expression vector DNA called pCI-aag-hsvTK (Ver. 1), which contains an alkyladenine DNA glycosidase (AAG) gene and a human herpes virus thymidine kinase (hsvTK) gene.

SEQ ID NO: 2: Designed expression vector DNA called pCI-aag-hsvTK-ape1 (Ver. 2), which contains an alkyladenine DNA glycosidase (AAG) gene, a human herpes virus thymidine kinase (hsvTK) gene, and an AP endonuclease (APE1) gene.

SEQ ID NO: 3: Designed expression vector DNA called pCI-aagL180E-hsvTK-ape1 (Ver. 2.1), which contains an alkyladenine DNA glycosidase variant ((AAG (L180F))) gene, a human herpes virus thymidine kinase (hsvTK) gene, and an AP endonuclease (APE1) gene.

SEQ ID NO: 4: Designed expression vector DNA called pCI-aag-hsvTK-ape1 (Ver. 3), which contains an alkyladenine DNA glycosidase (AAG) gene, a human herpes virus thymidine kinase (hsvTK) gene, and an AP endonuclease (APE 1) gene.

SEQ ID NO: 5: Designed expression vector DNA called pTrc-aag (wt), which contains an alkyladenine DNA glycosidase (AAG) gene.

SEQ ID NO: 6: Designed expression vector DNA called pTrc-aag (wt)-ape1, which contains an alkyladenine DNA glycosidase (AAG) gene and an AP endonuclease (APE1) gene.

SEQ ID NO: 7: Designed expression vector DNA called pTrc-ape1, which contains an AP endonuclease (APE1) gene.

SEQ ID NO: 8: Designed expression vector DNA called pCI-gfp, which contains a green fluorescent protein (GFP) gene.

SEQ ID NO: 9: Designed expression vector DNA harboring Genetic Circuit-A.

SEQ ID NO: 10: Designed expression vector DNA harboring Genetic Circuit-B.

SEQ ID NO: 11: Designed expression vector DNA harboring Genetic Circuit-C.

SEQ ID NO: 12: Designed expression vector DNA harboring Genetic Circuit-D.

The invention claimed is:

1. A selection method for a genetic switch and a genetic circuit, the selection method comprising:
    incubating cells transfected with
        a genetic circuit expression vector comprising a genetic circuit having a genetic switch expression sequence, and
        a transcription regulatory factor gene sequence encoding a transcription regulatory factor whose expression is induced by a genetic switch encoded by the genetic switch expression sequence, and
        a controllable expression vector having a controlled gene sequence whose expression is controlled by the transcription regulatory factor, the incubation being performed
    in a presence or absence of an activating compound that activates the genetic switch, with addition of a first death-determining compound that induces cell death under expression of the controlled gene sequence, and collecting viable cells, and/or
    in a presence or absence of the activating compound with addition of a second death-determining compound that induces cell death under non-expression of the controlled gene sequence; and
    collecting viable cells that survive the incubation,
    wherein the controllable expression vector comprises a first promoter sequence operably linked to and upstream of the controlled gene sequence, and
    the controlled gene sequence encodes an alkylated DNA repair enzyme; and
    the genetic circuit expression vector comprises a target sequence of the genetic switch operably linked to the transcription regulatory factor gene sequence and a second promoter sequence different from the first promoter sequence, the transcription regulatory factor gene sequence encoding a transcription factor being operable on the first promoter sequence, and the second promoter sequence being operably linked to the genetic switch expression sequence, incubation being performed
    (1) when the transcription regulatory factor is a transcription repression factor, in the absence of the activating compound with addition of an alkylating agent, or
    (2) when the transcription regulatory factor is a transcription activation factor, in the presence of the activating compound with addition of the alkylating agent.

2. The selection method for a genetic switch and a genetic circuit according to claim 1, wherein the controlled gene sequence comprises a first gene sequence and a second gene sequence, expression of each of which is controlled by the transcription regulatory factor, the first gene sequence encoding a protein different from that encoded by the second gene sequence.

3. The selection method for a genetic switch and a genetic circuit according to claim 1, wherein the controllable expression vector comprises: a first expression vector having a first gene sequence whose expression is controlled by the transcription regulatory factor; and a second expression vector having a second gene sequence whose expression is controlled by the transcription regulatory factor, the first gene sequence encoding a protein different from that encoded by the second gene sequence.

4. The selection method for a genetic switch and a genetic circuit according to claim 1, wherein the alkylated DNA repair enzyme comprises alkyladenine DNA glycosidase (AAG).

5. The selection method for a genetic switch and a genetic circuit according to claim 1, wherein the cells comprise an alkylating agent-hypersensitive Escherichia coli strain.

6. The selection method for a genetic switch and a genetic circuit according to claim 1, wherein the compound that causes alkylation of a gene comprises methanesulfonic acid (MMS).

7. A selection method for a genetic switch and a genetic circuit, the selection method comprising:
    incubating an alkylating agent-hypersensitive Escherichia coli strain transfected with
        a controllable expression vector comprising at least sequences according to the following items (a) and (b):
            (a) an enzyme gene sequence encoding alkyladenine DNA glycosidase (AAG); and
            (b) a first promoter sequence operably linked to the enzyme gene sequence according to the item (a) upstream of the enzyme gene sequence, and
        a genetic circuit expression vector comprising at least sequences according to the following items (c) to (f):
            (c) a second promoter sequence different from the first promoter sequence, the second promoter sequence being operably linked to a genetic switch expression sequence downstream thereof;
            (d) the genetic switch expression sequence;
            (e) a target sequence of a genetic switch encoded by the genetic switch expression sequence; and
            (f) a transcription regulatory factor gene sequence having the target sequence operably linked thereto, the transcription regulatory factor gene sequence encoding a CI protein that operates on the first promoter sequence according to the item (b), the incubation being performed
    in an absence of a compound that activates the genetic switch, with addition of methanesulfonic acid (MMS) for 15 minutes to 60 minutes; and
    collecting viable cells that survive the incubation.

8. A selection method for a genetic switch and a genetic circuit, the selection method comprising:
    incubating an alkylating agent-hypersensitive Escherichia coli strain transfected with
        a controllable expression vector comprising at least sequences according to the following items (a) and (b):
            (a) a first enzyme gene sequence encoding alkyladenine DNA glycosidase (AAG) and a second enzyme gene sequence encoding AP endonuclease (APE1); and
            (b) a first promoter sequence operably linked to the two enzyme gene sequences according to the item (a) upstream of the first and second enzyme gene sequences, and
        a genetic circuit expression vector comprising at least sequences according to the following items (c) to (f):
            (c) a second promoter sequence different from the first promoter sequence, the second promoter sequence being operably linked to a genetic switch expression sequence downstream thereof;
            (d) the genetic switch expression sequence;
            (e) a target sequence of a genetic switch encoded by the genetic switch expression sequence; and
            (f) a CI protein gene sequence having the target sequence operably linked thereto, the CI protein gene sequence encoding a CI protein that operates on the first promoter sequence according to the item (b), the incubation being performed in an absence of a compound that activates the genetic switch with addition of methanesulfonic acid (MMS) for 15 minutes to 60 minutes; and
collecting viable cells that survive the incubation.

9. The selection method for a genetic switch and a genetic circuit according to claim 1, wherein
the controllable expression vector comprises a first promoter sequence operably linked to and upstream of the controlled gene sequence, and
the controlled gene sequence comprises a first gene sequence encoding an alkylated DNA repair enzyme and a second gene sequence encoding a thymidine kinase, and
the genetic circuit expression vector comprises a target sequence of the genetic switch operably linked to the transcription regulatory factor gene sequence and a second promoter sequence different from the first promoter sequence, the transcription regulatory factor gene sequence encoding a transcription factor being operable on the first promoter sequence, and the second promoter sequence being operably linked to the genetic switch expression sequence,
the incubation being performed in two stages, in a first stage
(1) when the transcription regulatory factor gene sequence encoding a transcription regulatory factor is a transcription repression factor, in the presence of the activating compound, incubating the cells with addition of a mutagenic nucleoside, and collecting viable cells that survive the first stage, or
(2) when the transcription regulatory factor gene sequence encoding a transcription regulatory factor is a transcription activation factor, in the presence of the activating compound that activates the genetic switch, incubating the cells with addition of an alkylating agent and collecting viable cells that survive the first stage, and
in a second stage
(1) when the transcription regulatory factor gene sequence encoding a transcription regulatory factor is a transcription repression factor, incubating the collected cells that survived the first stage with the alkylating agent in the absence of the activating compound, and collecting viable cells that survive the second stage, or
(2) when the transcription regulatory factor gene sequence encoding a transcription regulatory factor is a transcription activation factor, incubating the collected cells that survived the first stage with the alkylating agent in the absence of the activating compound, and collecting viable cells that survive the second stage.

10. The selection method for a genetic switch and a genetic circuit according to claim 1, wherein
the controllable expression vector comprises
a primary controlled expression vector comprising a first enzyme gene sequence encoding an alkylated DNA repair enzyme and a first promoter sequence operably linked to the first enzyme gene sequence upstream of the first enzyme gene sequence, and
a secondary controlled expression vector comprising a second enzyme gene sequence encoding a thymidine kinase and a second promoter sequence operably linked to the second enzyme gene sequence upstream of the second enzyme gene sequence, and
the genetic circuit expression vector comprises a target sequence of the genetic switch operably linked to the transcription regulatory factor gene sequence, and a third promoter sequence different from the first and second promoter sequences, the third promoter sequence being operably linked to the genetic switch expression sequence
the incubation being performed in two stages, in a first stage
(1) when the transcription regulatory factor gene sequence encoding a transcription regulatory factor according is a transcription repression factor, in the presence of the activating compound, incubating the cells with addition of a mutagenic nucleoside and collecting viable cells that survive the first stage, or
(2) when the transcription regulatory factor gene sequence encoding a transcription regulatory factor is a transcription activation factor, in the presence of the activating compound, incubating the cells with addition of an alkylating agent, and collecting viable cells that survive the first stage, and
in a second stage
(1) when the transcription regulatory factor gene sequence encoding a transcription regulatory factor is a transcription repression factor, incubating the collected cells that survived the first stage with the alkylating agent in the absence of the activating compound, and collecting viable cells that survive the second stage, or
(2) when the transcription regulatory factor gene sequence encoding a transcription regulatory factor is a transcription activation factor, incubating the collected cells that survived the first stage with the alkylating agent in the absence of the activating compound, and collecting viable cells that survive the second stage.

11. The selection method for a genetic switch and a genetic circuit according to claim 9, wherein the alkylated DNA repair enzyme comprises alkyladenine DNA glycosidase (AAG), and the thymidine kinase comprises a human herpes virus derived thymidine kinase.

12. The selection method for a genetic switch and a genetic circuit according to claim 9, wherein the cells comprise an alkylating agent-hypersensitive *Escherichia coli* strain.

13. The selection method for a genetic switch and a genetic circuit according to claim 9, wherein the compound that causes alkylation of a gene comprises methanesulfonic acid (MMS), and the mutagenic nucleoside comprises 6-($\beta$-D-2-deoxyribo-furanosyl)-3,4-dihydro-8H-pyrimido[4,5-c][1,2]oxazin-7-one (dP).

14. A selection method for a genetic switch and a genetic circuit, the selection method comprising:
incubating an alkylating agent-hypersensitive *Escherichia coli* strain transfected with
a controllable expression vector comprising at least sequences according to the following items (a) and (b):
(a) a first enzyme gene sequence encoding alkyladenine DNA glycosidase (AAG) and a second enzyme gene sequence encoding a human herpes virus derived thymidine kinase; and
(b) a first promoter sequence operably linked to the first and second enzyme gene sequences according to the item (a) upstream of the first and second enzyme gene sequences, and
a genetic circuit expression vector comprising at least sequences according to the following items (c) to (f):
(c) a second promoter sequence different from the first promoter sequence, the second promoter sequence being operably linked to a genetic switch expression sequence downstream thereof;
(d) the genetic switch expression sequence;
(e) a target sequence of a genetic switch encoded by the genetic switch expression sequence; and
(f) a CI protein gene sequence having the target sequence operably linked thereto, the CI protein gene sequence encoding a CI protein that operates on the first promoter sequence according to the item (b)

in a presence of an activating compound that activates the genetic switch for 5 minutes to 60 minutes with addition of 6-(β-D-2-deoxyribo-furanosyl)-3,4-dihydro-8H-pyrimido[4,5-c][1,2]oxazin-7-one (dP) in a first incubation stage;

collecting viable cells that survive the first incubation stage;

incubating the collected cells for 15 minutes to 60 minutes with addition of methanesulfonic acid (MMS) in the absence of the activating compound in a second incubation stage; and collecting viable cells that survive the second incubation stage.

15. A selection method for a genetic switch and a genetic circuit, the selection method comprising:

incubating an alkylating agent-hypersensitive *Escherichia coli* strain transfected with a controllable expression vector comprising at least sequences according to the following items (a) and (b):
(a) a first enzyme gene sequence encoding alkyladenine DNA glycosidase (AAG), a second enzyme gene sequence encoding a human herpes virus derived thymidine kinase, and a third enzyme gene sequence encoding AP endonuclease (APE1); and
(b) a first promoter sequence operably linked to the first, second, and third enzyme gene sequences according to the item (a) upstream of the first, second, and third enzyme gene sequences, and a genetic circuit expression vector comprising at least sequences according to the following items (c) to (f):
(c) a second promoter sequence different from the first promoter sequence, the second promoter sequence being operably linked to a genetic switch expression sequence downstream thereof;
(d) the genetic switch expression sequence;
(e) a target sequence of a genetic switch encoded by the genetic switch expression sequence; and
(f) a CI protein gene sequence having the target sequence operably linked thereto, the CI protein gene sequence encoding a CI protein that operates on the first promoter sequence according to the item (b)

in a presence of an activating compound that activates the genetic switch for 5 minutes to 60 minutes with addition of 6-(β-D-2-deoxyribo-furanosyl)-3,4-dihydro-8H-pyrimido[4,5-c][1,2]oxazin-7-one (dP) in a first incubation stage;

collecting viable cells that survive the first incubation stage;

incubating the collected cells for 15 minutes to 60 minutes with addition of methanesulfonic acid (MMS) in the absence of the activating compound in a second incubation stage; and collecting viable cells that survive the second incubation stage.

16. The selection method for a genetic switch and a genetic circuit according to claim 1, wherein the genetic circuit expression vector has a base sequence set forth in any one of SEQ ID NOS: 1 to 6 of the sequence listing.

17. The selection method for a genetic switch and a genetic circuit according to claim 7, wherein the controllable expression vector has a base sequence set forth in any one of SEQ ID NOS: 1 to 6 of the sequence listing.

18. The selection method for a genetic switch and a genetic circuit according to claim 8, wherein the controllable expression vector has a base sequence set forth in any one of SEQ ID NOS: 2, 3, 4, and 6 of the sequence listing.

19. The selection method for a genetic switch and a genetic circuit according to claim 14, wherein the controllable expression vector has a base sequence set forth in any one of SEQ ID NOS: 1 to 4 of the sequence listing.

20. The selection method for a genetic switch and a genetic circuit according to claim 15, wherein the controllable expression vector has a base sequence set forth in any one of SEQ ID NOS: 2 to 4 of the sequence listing.

* * * * *